(12) United States Patent
Bittner Ortega et al.

(10) Patent No.: US 11,331,355 B2
(45) Date of Patent: May 17, 2022

(54) **PHARMACEUTICAL COMPOSITION BASED ON BACTERIOPHAGES AGAINST *F. NUCLEATUM*; USE IN THE TREATMENT OF DISEASES ASSOCIATED WITH THIS PATHOGEN**

(71) Applicant: UNIVERSIDAD ANDRÉS BELLO, Santiago (CL)

(72) Inventors: Waldemar Mauricio Bittner Ortega, Colina (CL); Pamela Isabel Machuca Valenzuela, Santiago (CL); Valeska Susana Herrera Sanhueza, Santiago (CL); Ignacio Andrés Fuentevilla Morgado, Santiago (CL)

(73) Assignee: UNIVERSIDAD ANDRÉS BELLO

( * ) Notice: Subject to any disclaimer, the term of this patent is extended or adjusted under 35 U.S.C. 154(b) by 181 days.

(21) Appl. No.: 16/348,655

(22) PCT Filed: Nov. 9, 2016

(86) PCT No.: PCT/IB2016/056107
§ 371 (c)(1),
(2) Date: May 9, 2019

(87) PCT Pub. No.: WO2018/087579
PCT Pub. Date: May 17, 2018

(65) Prior Publication Data
US 2020/0054699 A1     Feb. 20, 2020

(51) Int. Cl.
*A61K 35/76*     (2015.01)
*A61P 31/04*     (2006.01)
*A61K 9/00*     (2006.01)

(52) U.S. Cl.
CPC ............ *A61K 35/76* (2013.01); *A61K 9/0053* (2013.01); *A61P 31/04* (2018.01)

(58) Field of Classification Search
None
See application file for complete search history.

(56) References Cited

FOREIGN PATENT DOCUMENTS

EP     0414304 B1     11/1994

OTHER PUBLICATIONS

Machuca et al., Appl. Environ. Microbiol. 76(21): 7243-250 (2010).*
Cochrane et al: "Complete genome sequences and analysis of the Fusobacterium nucleatum subspecies animalis 7-1 bacteriophage [phi]Funu1 and [phi]Funu2", Anaerobe, London, GB, vol. 38, Nov. 3, 2015 (Nov. 3, 2015), pp. 125-129.
Machuca et al: "Isolation of a Novel 11,30, Bacteriophage Specific for the Periodontal 32,33 Pathogen Fusobacterium nucleatum", Applied and Environmental Microbiology, vol. 76, No. 21, Nov. 1, 2010 (Nov. 1, 2010), pp. 7243-7250.

* cited by examiner

*Primary Examiner* — Erin M. Bowers
(74) *Attorney, Agent, or Firm* — Fox Rothschild LLP

(57) ABSTRACT

A pharmaceutical composition comprising: a) an effective amount of one or more lytic bacteriophages specific against *Fusobacterium nucleatum* selected from FnpΦ02-14, FnpΦ11 and FnnΦ107 or mixtures of them; and b) one or more pharmaceutically acceptable carrier and/or excipients. Method for preventing and/or treating diseases associated with *Fusobacterium nucleatum* and the use of the pharmaceutical composition for treating a disease associated with *Fusobacterium nucleatum* of the oral cavity such as V periodontal disease, among others.

37 Claims, 23 Drawing Sheets
Specification includes a Sequence Listing.

```
PA6      AAGCTTGTTGGTGCCGGTATTTTGCCTGCTGATTCTCGTACGGTGTTGGAGATGTTGGGG 3106
FnpΦ02   AAGCTTGTTGGTGCCGGTATTTTGCCTGCTGATTCTCGTACGGTGTTGGAGATGTTGGGG 60
         ************************************************************

PA6      CTTGATGATGTGCAGGTTGAGGCTGTGATGCGTCATCGTGCTGAGTCGTCTGACCCGTTG 3166
FnpΦ02   CTTGATGATGTGCAGGTTGAGGCTGTGATGCGTCATCGTGCTGAGTCGTCTGACCCGTTG 20
         ************************************************************

PA6      GCGGTGCTTGCTGGGGCTATATCGCGTCAAACTAACGAGGTATGATAGGCGATGGCTTCG 3226
FnpΦ02   GCGGCACTGGCTGGGGCTATATCGCGTCAAACTAACGAGGTTTGATAGGCGATGGCTTCG 180
         ****  ** ******************************* ******************

PA6      GGGGTTGAGGCGAGGCTTGCGGCGACTGAGTATCAGCGTGAGGCGGTCAGGTTTGCTGGG 3298
FnpΦ02   GGTGCTATGTCGAGGCTTGCGGTGACTGAGTATCAGCGGCAGGCGGATTCGTTTTGCCGGG 240
         ** * * *  ************ *************** ***** * * ***** ***

PA6      AAGTATGCGGGCTATTATTCTGAGCTTGGTCGTTTGTGGCGTGCCGGCAGGATGAGTGAC 3346
FnpΦ02   AAATACGCTGGGTATTATTCTGAGCTTGGTCGTTTGTGGCGTGCCGGGAAGATGAGTGAC 300
         ** ** ** ** ******************************** *  **********

PA6      ACGCAGTATGTGCGTTTGTGTGTGGAGTTGGAGCGTGCCGGCCATGATGGTTCGGCATCG 3406
FnpΦ02   ACGCAGTATGTGCGTTTGTGTGTGGAGTTGGAGCGTGCCGGCCATGATGGTTCCGCGACT 360
         ***************************************************** ** *

PA6      TTGGCTGCCAGGTTTGTGTCGGATTTTCG 3435
FnpΦ02   ATGGCGGCCAAATTCGTTTCAAAATTTCG 389
         ****  ****  ** ** **  * *****
```

B

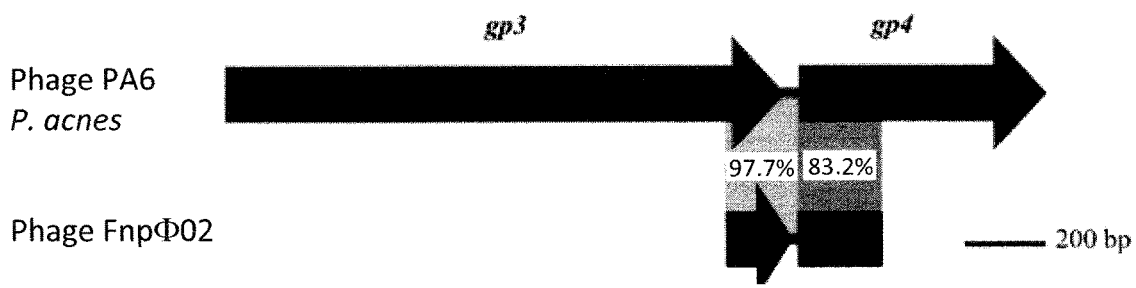

Phage PA6 *P. acnes*

Phage FnpΦ02

200 bp

C gp3
```
PA6      KLVGAGILPADSRTVLEMLGLDDVQVEAVMRHRAESSDPLAVLAGAISRQTNEV 441
         KLVGAGILPADSRTVLEMLGLDDVQVEAVMRHRAESSDPLA LAGAISRQTNEV
FnpΦ02   KLVGAGILPADSRTVLEMLGLDDVQVEAVMRHRAESSDPLAALAGAISRQTNEV 54
``` gp4
```
PA6      MASGVEARLAATEYQREAVRFAGKYAGYYSELGRLWRAGRMSDTQYVRLCVELERAGHDG 60
         MASG  +RLA TEYQR+A+RFAGKYAGYYSELGRLWRAG+MSDTQYVRLCVELERAGHDG
FnpΦ02   MASGAMSRLAVTEYQRQAIRFAGKYAGYYSELGRLWRAGKMSDTQYVRLCVELERAGHDG 60

PA6      SASLAARFVSDF 72
         SA++AA+FVS F
FnpΦ02   SATMAAKFVSKF 72
```

Fig. 9
A
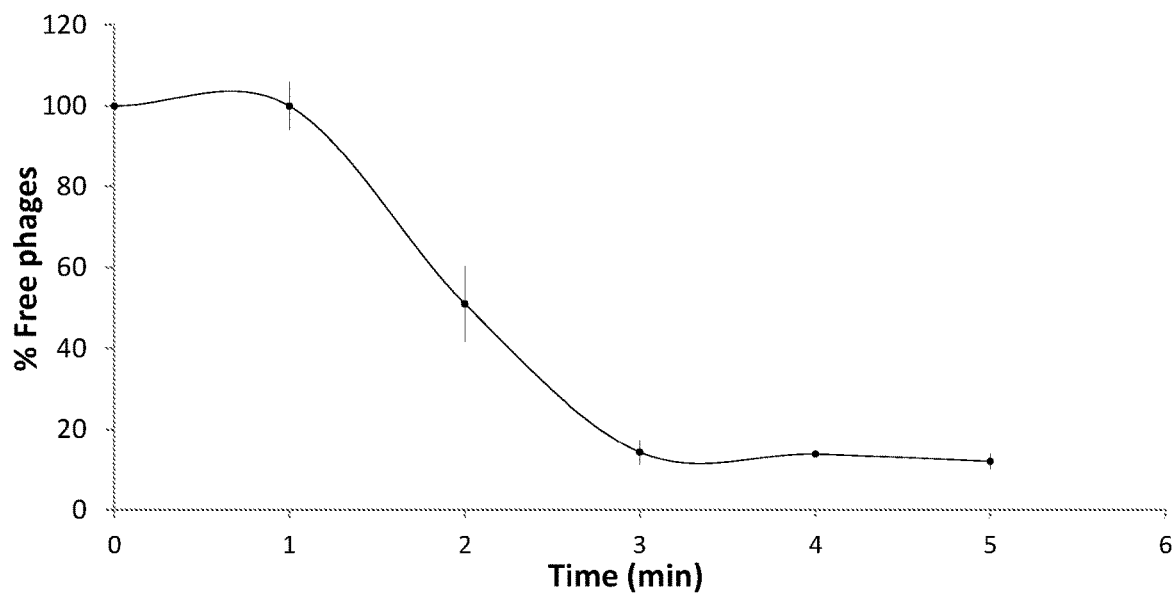
B
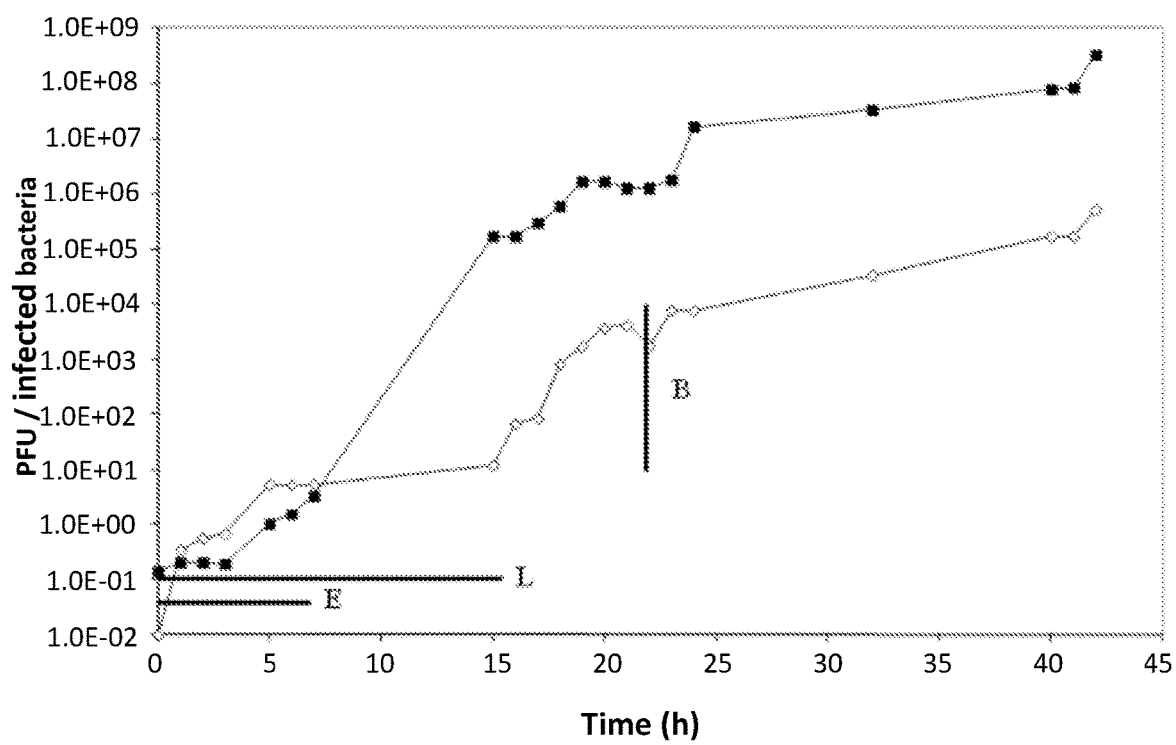

Fig. 10
A
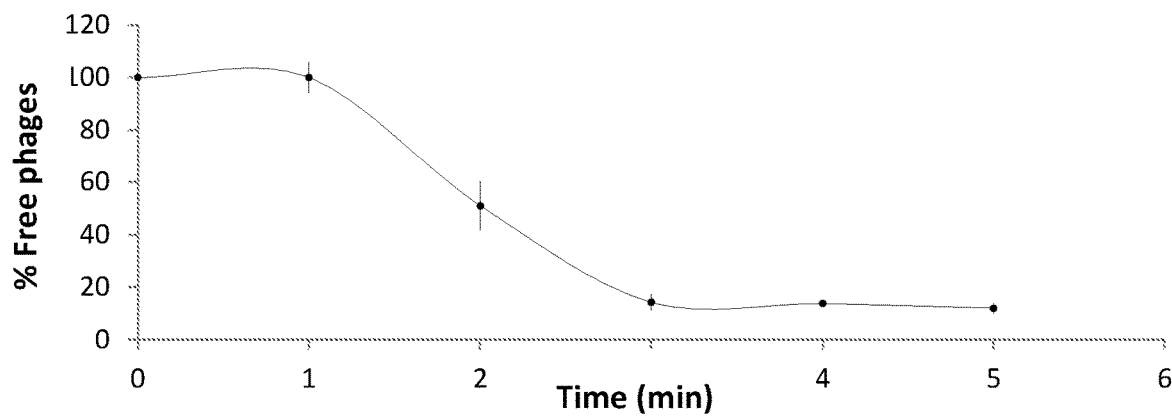
B
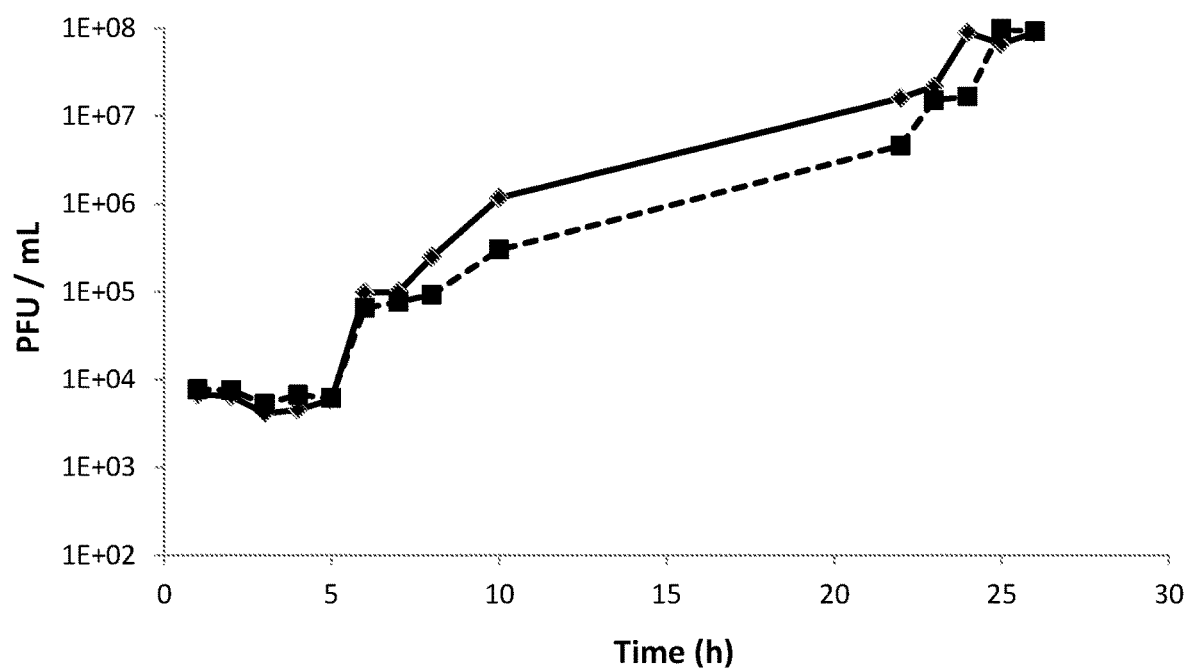

Fig. 11
A
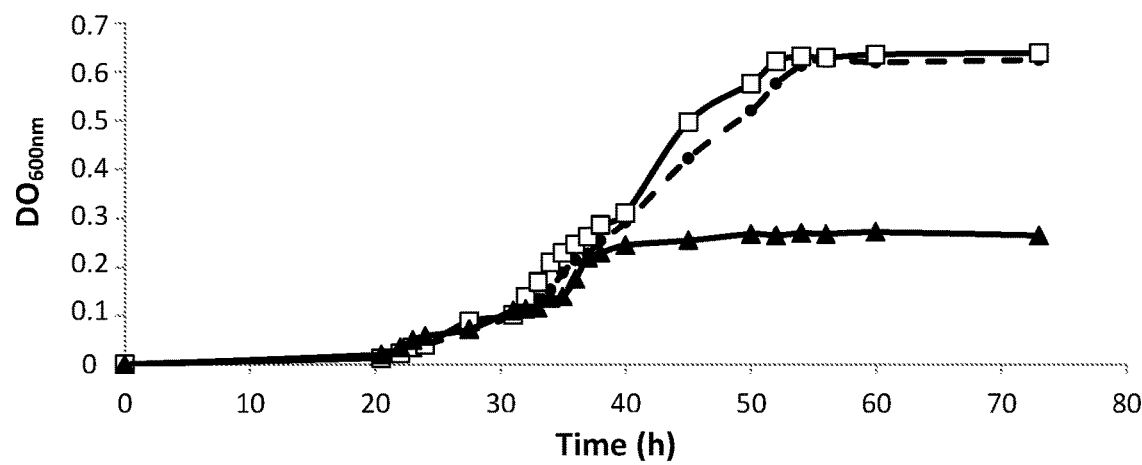
B
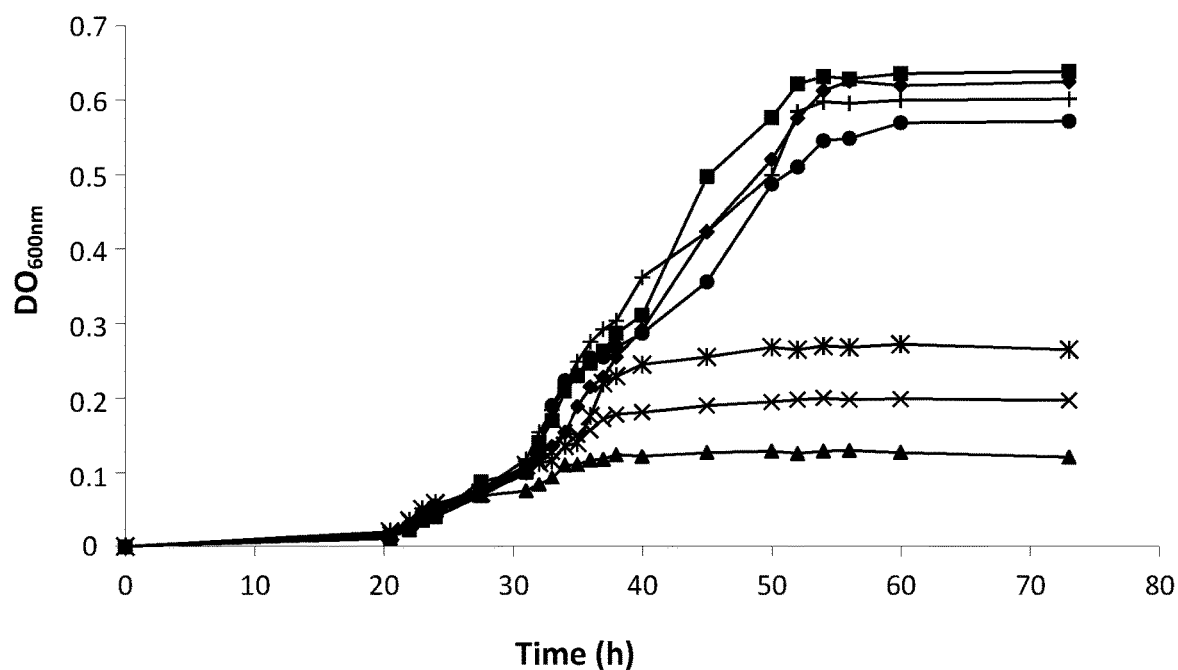

Fig. 14
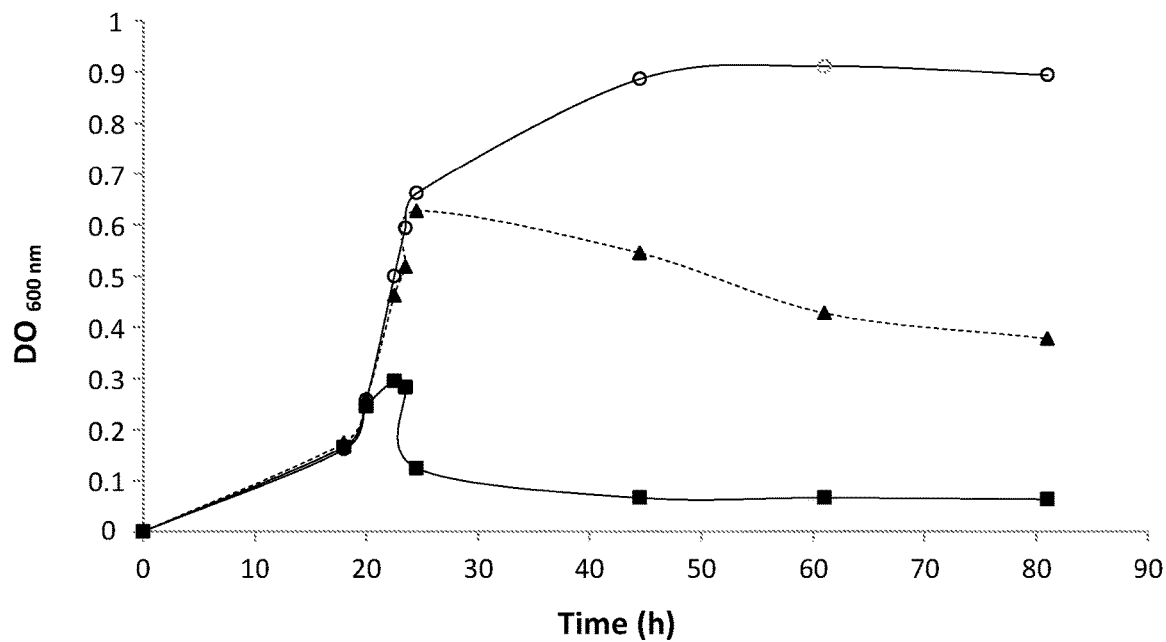
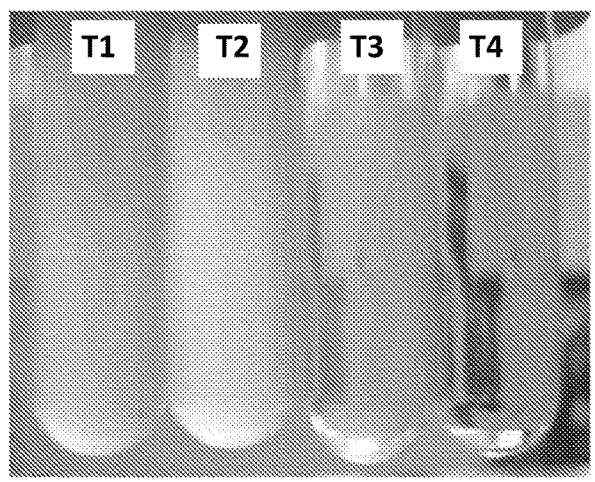

Fig. 15 (A, B, C)
A
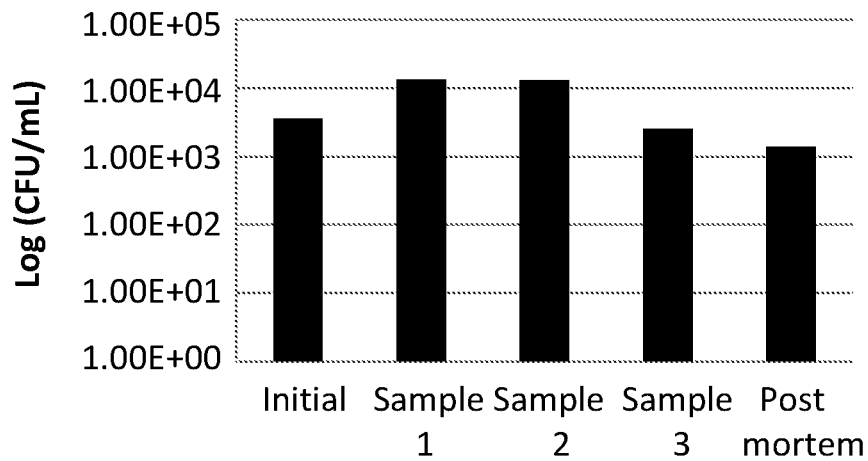
B
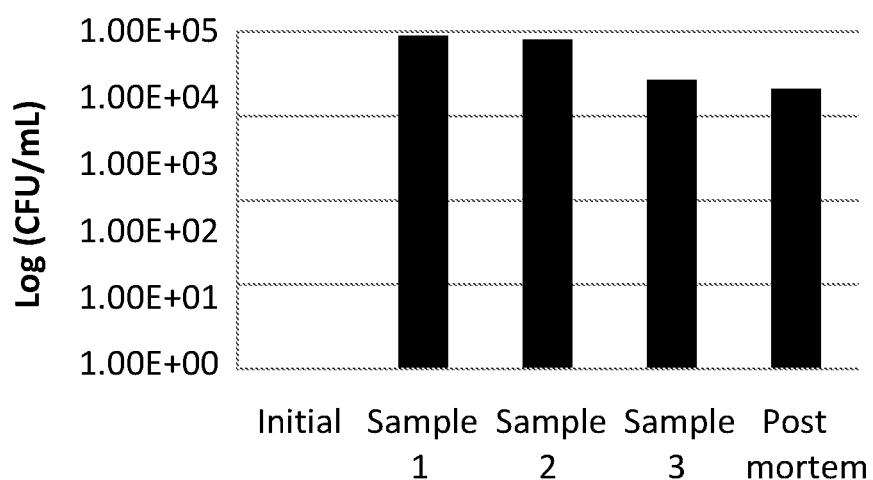
C
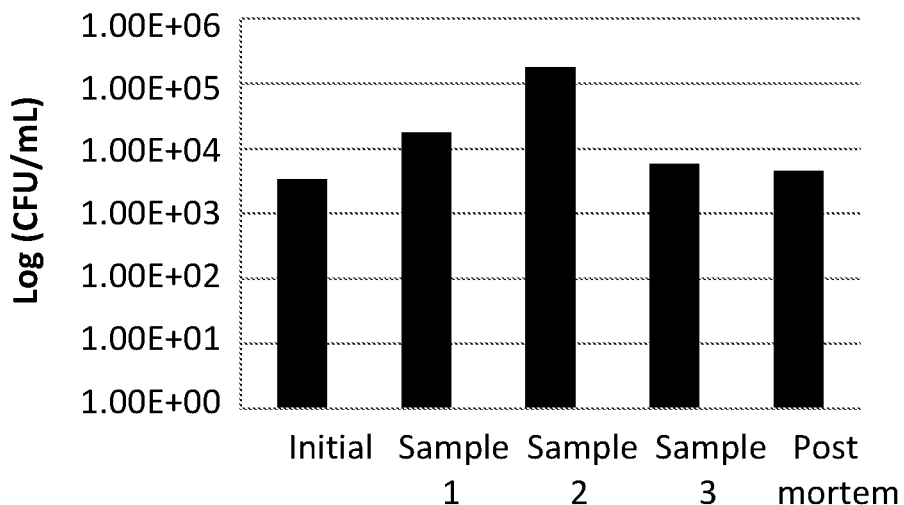

Fig. 15 (D, E, F])
D
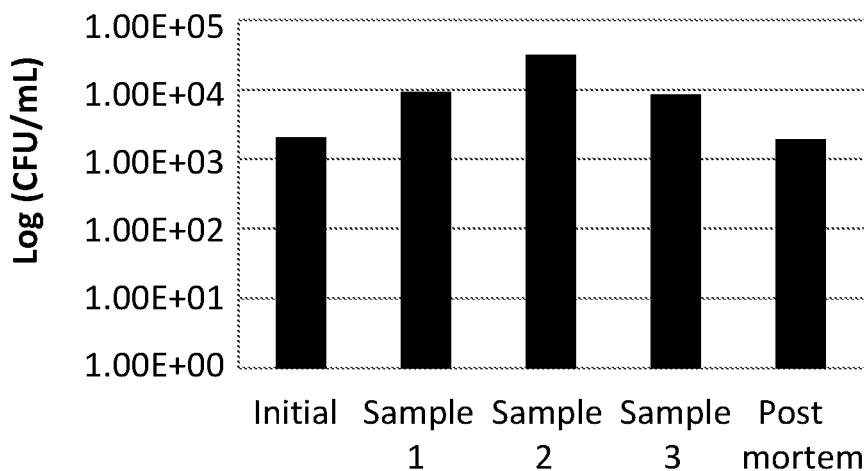
E
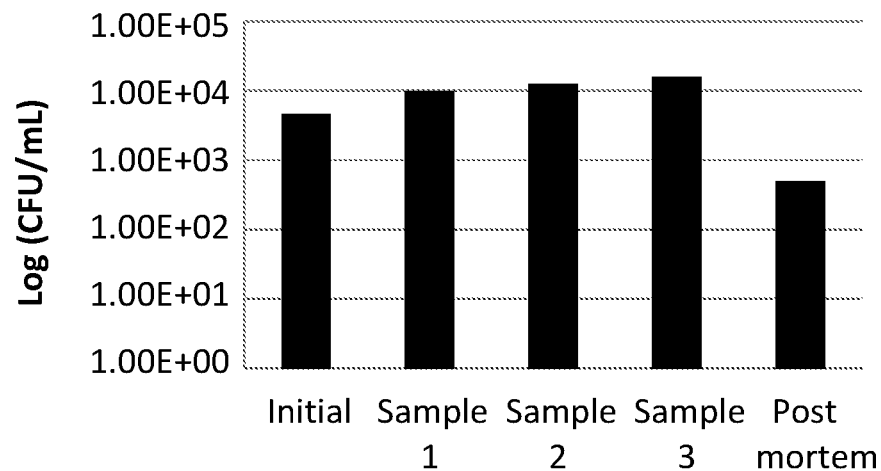
F
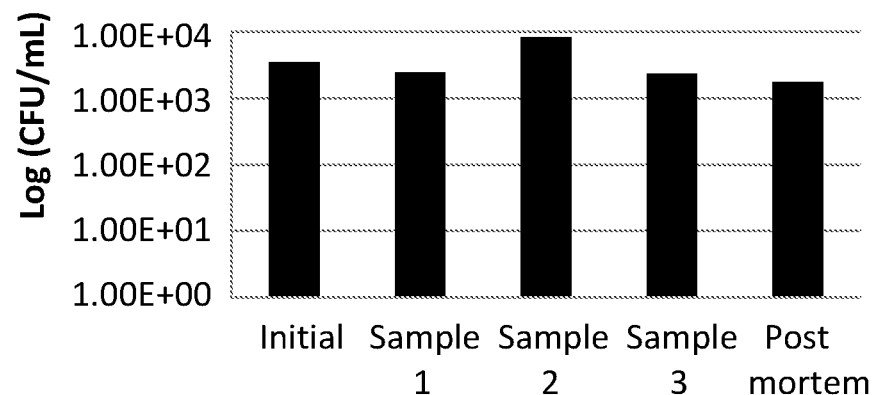

Fig. 16 (A, B, C)
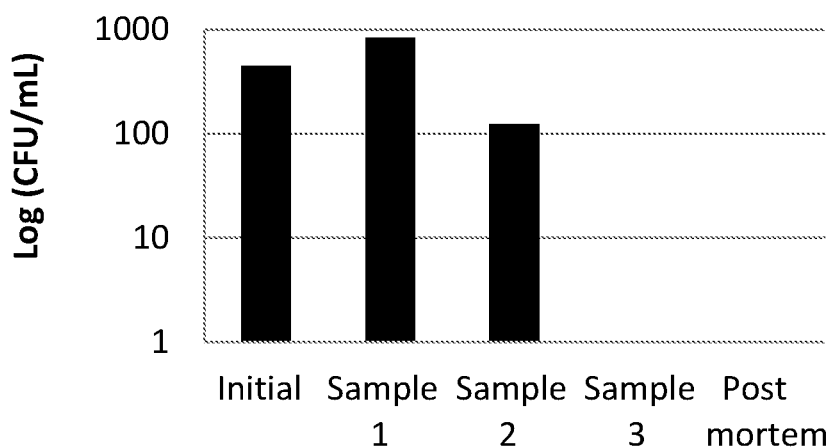
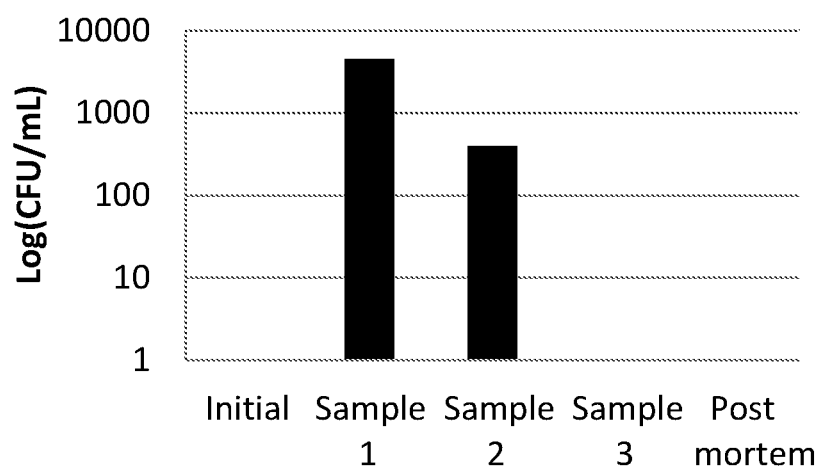
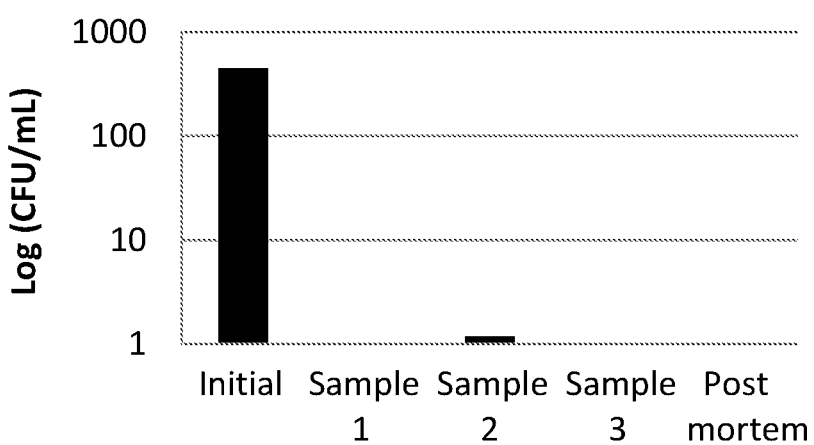

Fig. 16 (D, E, F)
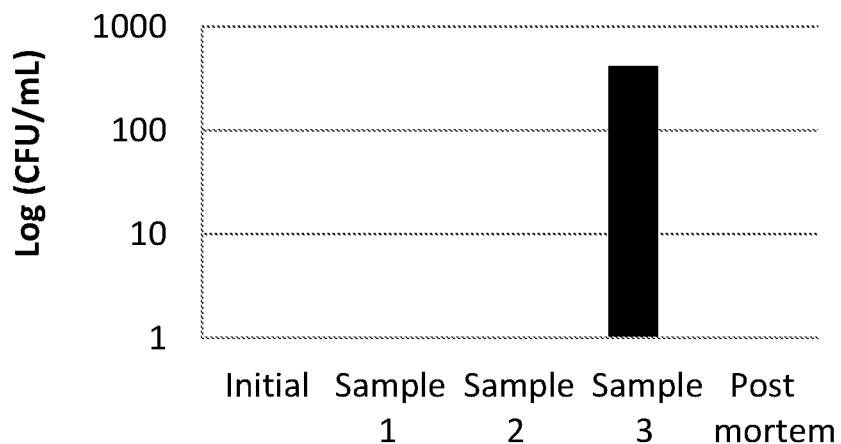
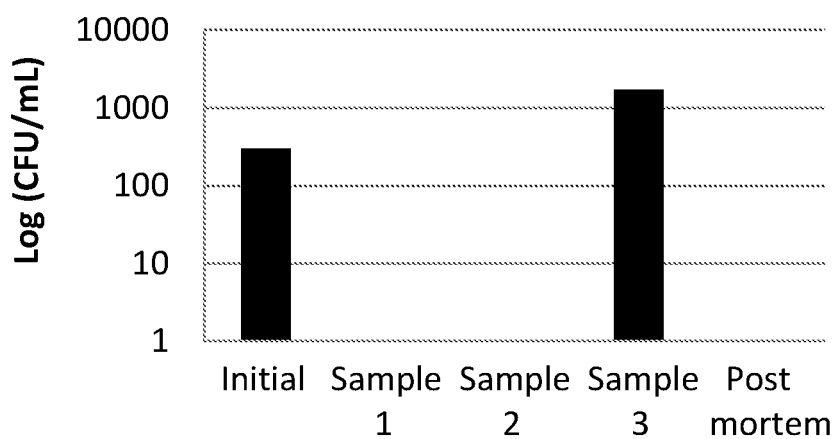
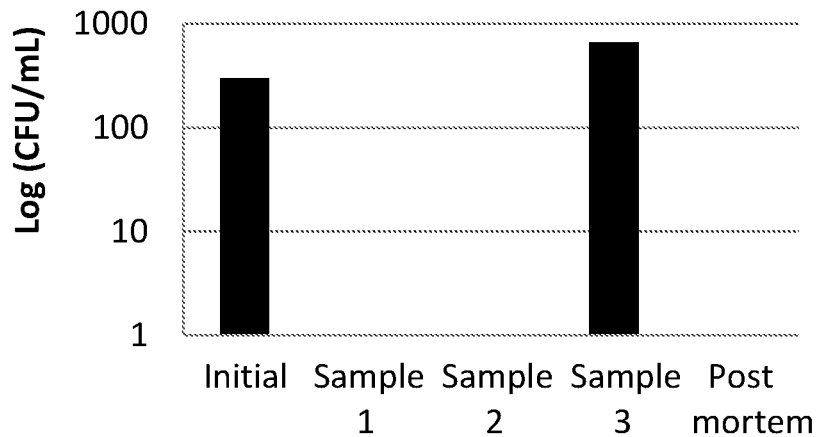

Fig. 17 (A, B, C)
A
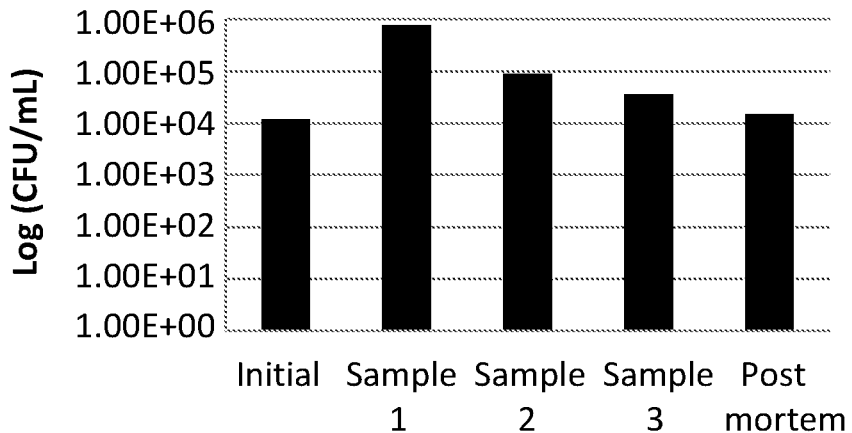
B
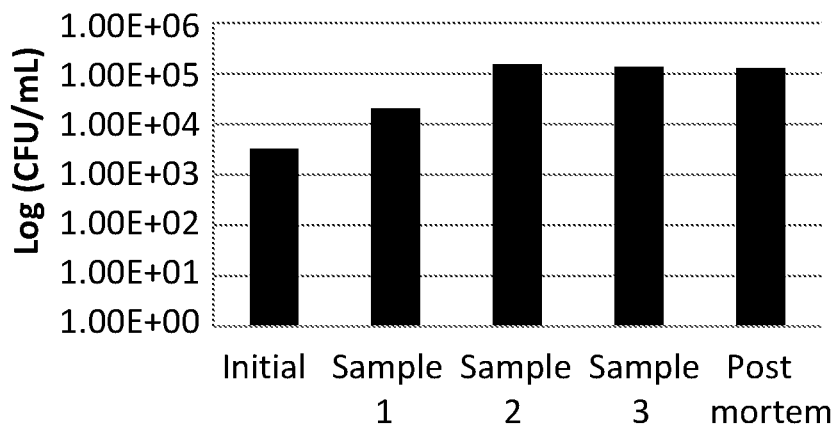
C
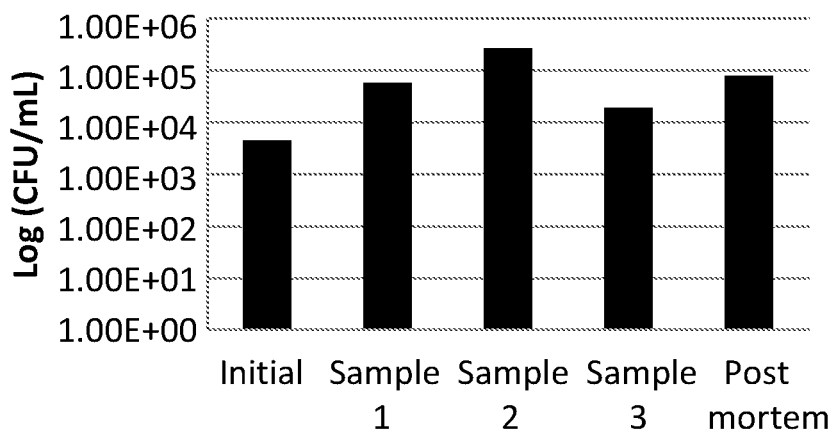

Fig. 17 (D, E, F)
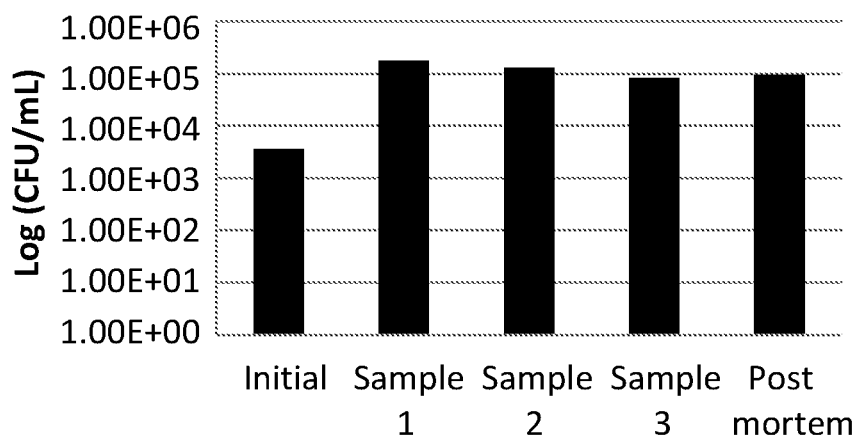
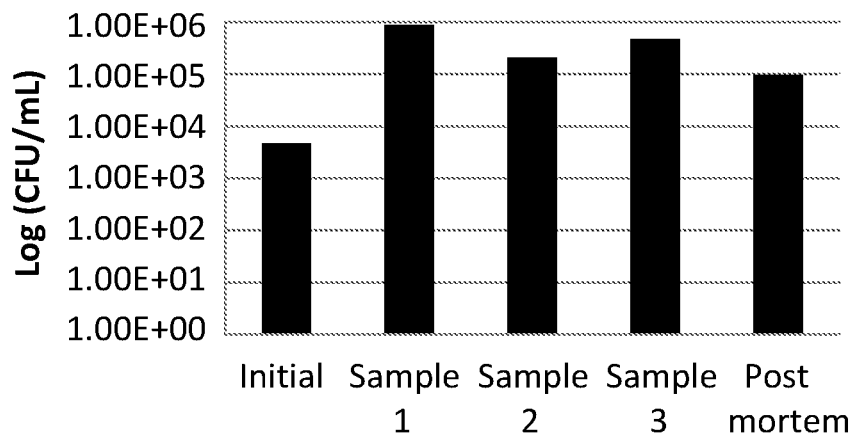
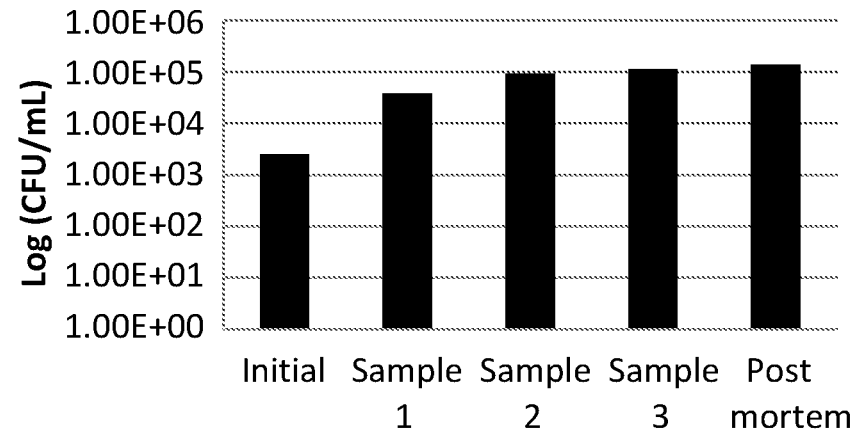

Fig. 27 (A, B)
A
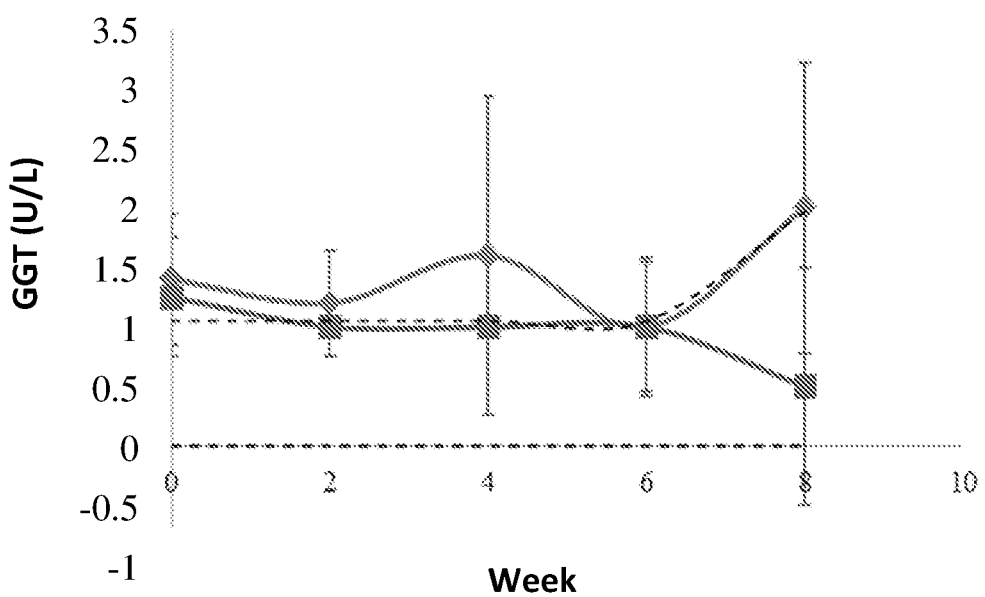
B
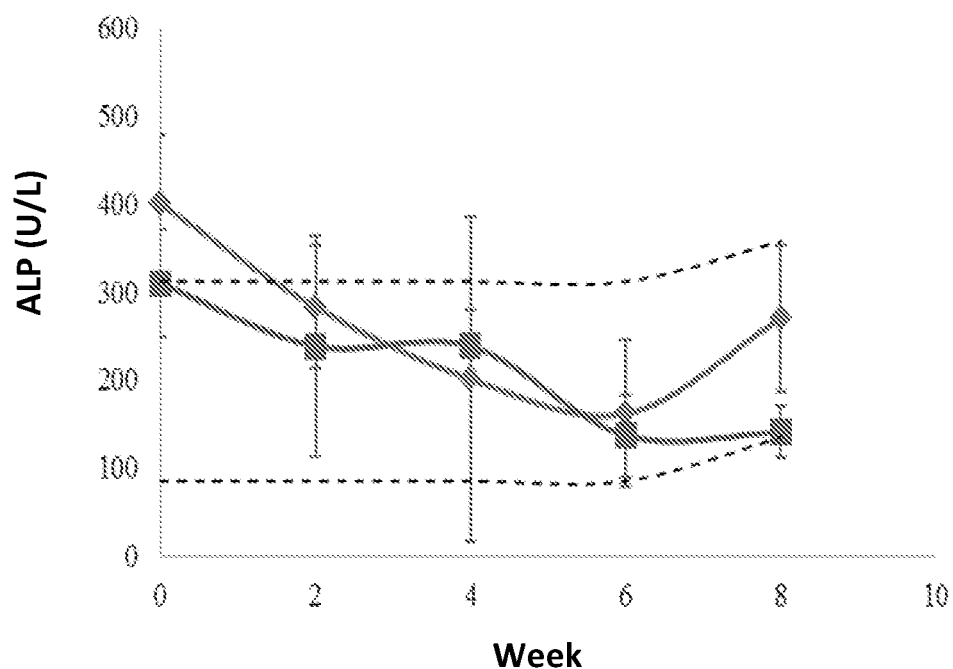

Fig. 27 (C, D, E)
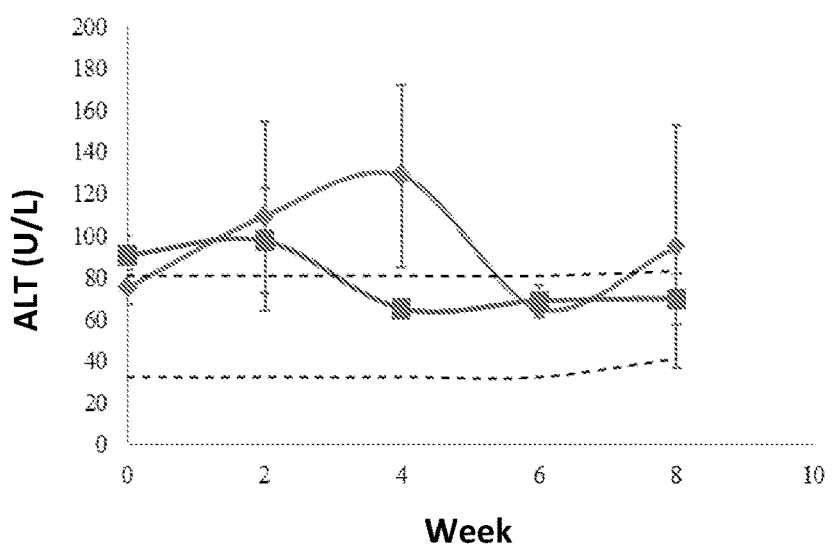
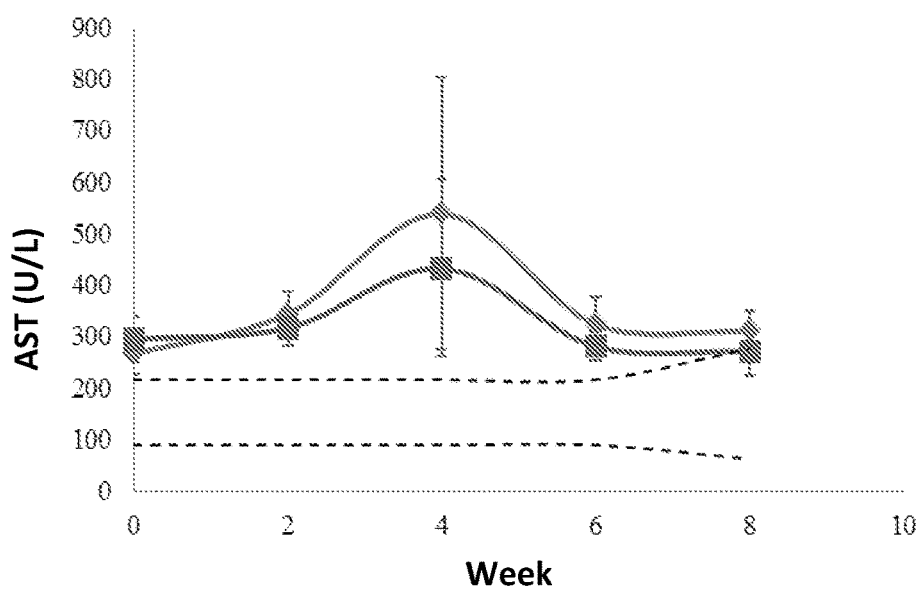
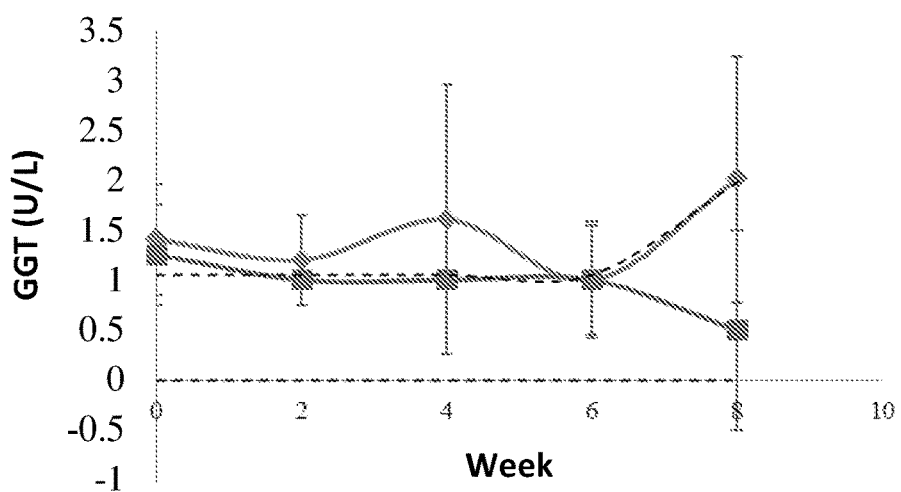

Fig. 28
A
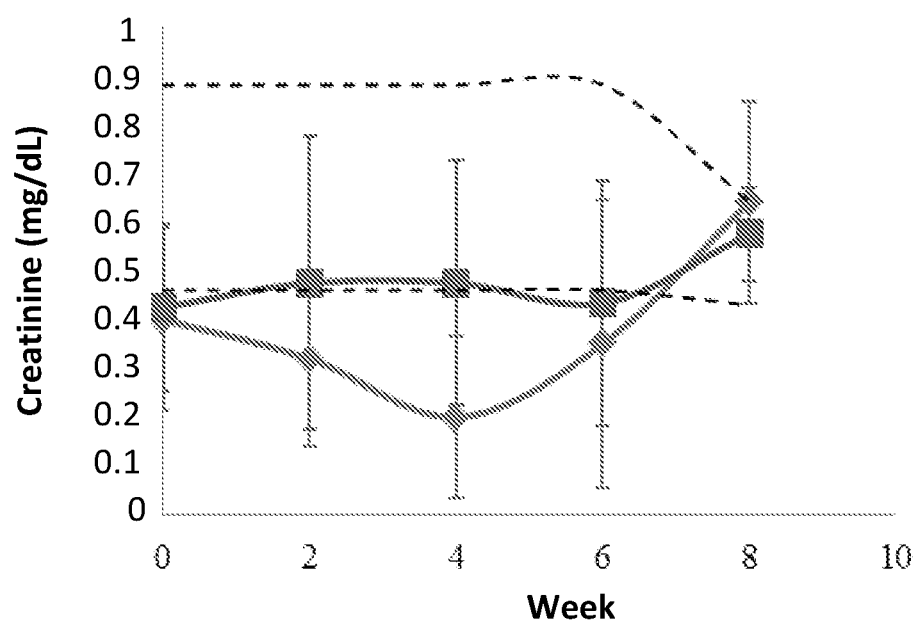
B
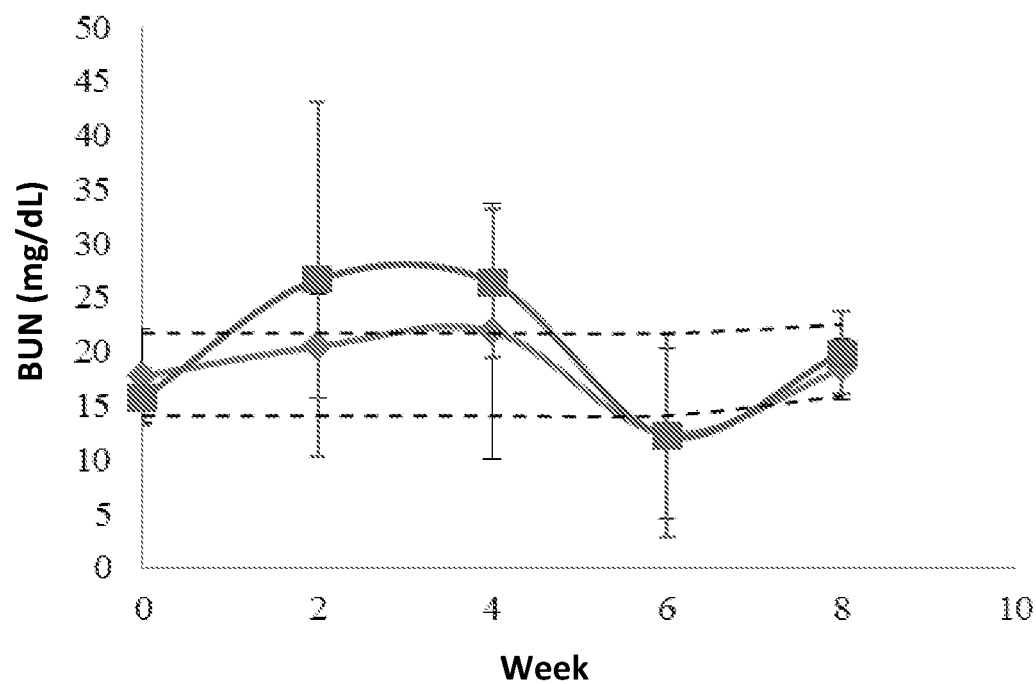

PHARMACEUTICAL COMPOSITION BASED ON BACTERIOPHAGES AGAINST *F. NUCLEATUM*; USE IN THE TREATMENT OF DISEASES ASSOCIATED WITH THIS PATHOGEN

DISCLOSURE

The invention hereby refers to a composition containing a bacteriophage specific against *Fusobacterium nucleatum*, useful in treating diverse diseases associated to this bacteria wherein the bacteriophage is a lytic bacteriophage specific for *Fusobacterium nucleatum*.

The invention refers, more specifically, to the compositions for a dentist purpose containing one or more lytic bacteriophages for *F. nucleatum*, useful in treating periodontal disease (PD from now on).

In a particular way, the invention hereby refers to a composition containing one or more bacteriophages specific against *Fusobacterium nucleatum*, useful in preventing extra oral diseases produced by systemic dissemination of *Fusobacterium nucleatum*. In this way the compositions of the invention comprising a lytic bacteriophage specific for *Fusobacterium nucleatum* serve in preventing diverse diseases associated to this bacteria such as Abnormal Pregnancy Outcomes and colorectal cancer.

The invention hereby refers to pharmaceutically acceptable compositions, composed by one or more lytic bacteriophages selected from the group consisting of FnpΦ02-14, FnpΦ11 and FnnΦ107, which are bacteriophages specific against *Fusobacterium nucleatum*.

Bacteriophages FnnΦ107, FnpΦ11 and FnpΦ02-14, which are a part of the invention hereby, have been deposited under the Budapest Treaty in the International Depositary Authority of Canada (IDAC) under the deposit numbers of IDAC 300115-01, IDAC 300115-02 and IDAC 300115-03, respectively.

Antecedents of the Prior Art

PD corresponds to a group of alterations affecting supporting tissues of teeth (periodontium), such as gum, periodontal ligament and alveolar bone.

Statistically, according to the World Health Organization, this disease constitutes an important health problem in the world, affecting around 35 to 50% of the adult population (Petersen et al., Bull World Health Organ., Vol. 83(9), pages 661-669, 2005). Even more, prevalence researches have been done in different countries, such as a research carried out in the United States between 2009 and 2010, which showed that 47% of adults from age 30 and above present periodontitis (8.7% mild periodontitis, 30% moderate y 8.5% severe), and given that periodontitis increases with aging, it was observed that 70% of adults from age 65 and above present periodontitis (Thornton-Evans G. et al, Public Health Rep., Vol. 125(6): pages 817-830, 2010).

The etiology of the periodontal disease has been widely described, with different hypothesis about it. One of the most accepted hypothesis is the proposal of the concept of "ecological plaque hypothesis". This hypothesis suggests that periodontal disease is an endogenous, opportunistic infection, caused by an imbalance in the composition of resident microflora (normal flora) in periodontal pocket. This disturbance in the habitat establishes a favorable environment for propagation of emerging pathogenic species. Ecological studies of (Socransky and Haffajee, Periodontology 2000, Vol. 38, pages 135-187, 2005) have defined six bacterial "complexes", all of them denominated by a color and composed by bacterial species interacting with one another, which present an analogue function inside the dental plaque. From them, blue, yellow, green and purple complexes contain species considered nonpathogenic and predominant in dental plaque of healthy individuals; and orange complexes, composed by *Prevotella intermedia, P. nigrescens, Parvimonas micra*, three subspecies of *Fusobacterium nucleatum, F. periodonticum, Streptococcus constellatus, Eubacterium nodatum, Campylobacter rectus* and *C. Showae*; and red complex, composed by *Porphyromonas gingivalis, Treponema denticola* y *Tannerella forsythia*, would be involved in the start and progression of the disease (Socransky S. et al., Oral Microbiology and Immunology, Vol. 3, pages 1-7, 1988; Socranscky S. et al, J Clin Periodontol., Vol. 25(2), pages 134-144, 1998; Socransky and Haffajee, Periodontology 2000, Vol. 38, pages 135-187, 2005). Even though it is a disease which depends of the synergy of microbiological and environmental elements, certain bacteria stand out as a key in the development of the disease. Therefore, red complex *Porphyromonas gingivalis* has been associated with the progression of periodontal destruction by placing itself in the bottom of the periodontal pocket and applying a direct effect on the periodontal soft tissues. On the other hand, orange complex places itself in the middle area of the plaque and is related both to initiation and progression of the disease, as it works as a bridge for the colonization of the red complex species (Kolenbrander et al., Periodontology 2000, Vol. 42, pages 47-79, 2006). Among the species of the orange complex, Gram-negative bacteria *Fusobacterium nucleatum* has been proposed as a key in the dental plaque maturation, because it is capable of coaggregating with almost all of the known oral bacteria, including both early and late settlers (Bradshaw et al., Infect Immun, Vol. 66: pages 4729-4732, 1998). Therefore, *F. nucleatum* allows the interaction of oral bacteria which do not have this adhesion capacity in a natural way, being the presence of a multitude of adhesins its main virulence factor (Kolenbrander et al., Periodontology 2000, Vol. 42, pages 47-79, 2006).

Clinical appearance of periodontal disease can be divided in gingivitis and periodontitis. Gingivitis is the mildest and most common form of this disease, corresponding a reversible inflammation of the soft tissues surrounding the tooth (mainly gum), and that can be quickly controlled with effective dental hygiene. On the other hand, periodontitis is a chronic, irreversible inflammation extending from soft tissues to alveolar bone, characterized by the progressive destruction of the periodontal ligament, generating the loss of adhesion of the gum to the tooth. This loss of adhesion causes the formation of a periodontal pocket, which increases its depth as the disease progresses, even endangering the alveolar bone, which can finally cause the loss of the tooth (Armitage, Periodontol 2000, Vol 34, pages 9-21, 2004). Periodontitis may appear also in two different forms: chronic periodontitis and aggressive periodontitis. The chronic form appears usually in seniors, presents a slow progression and has been related to a partial loss of the immune system; on the other hand, aggressive periodontitis shows up in earlier ages, its progression is fast and a family likelihood pattern has been observed; therefore, a related genetic factor has been suggested (Kinane y Bouchard, J Clin Periodontol, 35(8 Suppl), pages 333-337, 2008).

Periodontitis may not only cause tooth loss, but may also be associated with increasing the risk of adverse pregnancy outcomes. The mechanism of systemic dissemination proposed is that the periodontal pathogens may cross the placenta into the fetal circulation and amniotic fluid, or the inflammatory mediators produced locally in the periodontium may enter the systemic circulation (Hajishengallis G, Nat Rev Immunol., Vol. 15(1), pages 30-44, 2015).

Periodontitis may also be associated with increasing the risk of colorectal cancer by a mechanism of dissemination via ulcerated gingival pockets that allow the bacteria to access the bloodstream, or *F. nucleatum* may facilitates colon tissue infection by acting as a vector for other oral microbes (Flynn, K., et al, mSphere. Vol. 1(3): e00102-16, 2016). There are a potential mechanism about the association between *F. nucleatum* and immune response in colorectal cancer (Nosho, K. et al., World J Gastroenterol., Vol. 22(2), pages 557-66, 2016).

Treatments and prevention methods against periodontal disease include treatments with mouthwash and antibiotics inhibiting colonization, growth or spreading of bacterial etiologic agents related to this disease.

Among the most common treatments of periodontal disease, chlorhexidine gluconate based (a local antimicrobial agent) mouthwash stands out. Use of chlorhexidine has important limitations when it comes to adding it to toothpaste, especially because its effect is suppressed when combining it with foaming agents, and because if it is used for a long time, it might cause dental stains, changes in gustatory perception and alterations of the oral mucosa (Baehni et al., Oral Disease, Vol. 9, pages 23-29, 2003). Additionally, standard treatment against periodontal disease is based in antibiotics, such as amoxicillin or metronidazole. However, the use of antibiotics in treating PD is not problem-free, given that its frequent and prolonged use might increase the possibility of experiencing side effects as a result of this consumption (Dar-Odeh N S. et al., Ther Clin Risk Man., Vol. 6, pages 301-306, 2010). On the other hand, its use might generate tolerance of the microorganisms towards these antimicrobial agents (Ardila C M et al., Journal of Periodontal Research, Vol. 45, pages 557-563, 2010).

Another new way of treating periodontal disease is the use of biological agents, in order to eliminate the colonizing bacteria causing PD. Document US 2004/0234461 A1 establishes a method for treating and preventing dental caries and periodontal disease by using antibacterial enzymes codified by bacteriophages, capable of inhibiting the colonization of bacteria in the oral cavity. Specific bacteriophages for *S. mutans* are disclosed, named as phages M102, phage e10 and phage f1. In a similar way, document EP0414304 B1 discloses oral bacteriophages for *Streptococcus mutans*, *Actinomyces viscosus* and *Streptococcus sanguis*.

In other ways methods of treatment and compositions for treating bacterial infections with proteins, enzymes, peptides or bacteriophages derived fragments have been described in document WO 2004/064732 A2. This document refers specifically to a lytic enzymes coded by a specific bacteriophage and/or holin proteins, or peptides and fragments thereof together with a pharmaceutically acceptable carrier in treating bacterial infections and prophylaxis. It indicates the adding of lytic enzymes derived from the bacteriophage in a toothpaste or mouthwash with the aim of treating bacterial dental infections of different types and respiratory system diseases.

In the scientific dissemination article "Isolation of a Novel Bacteriophage Specific for the Periodontal Pathogen *Fusobacterium nucleatum*" (Machuca et al., Appl. Environ. Microbiol., Vol. 76(21), pages 7243-7250, 2010), the discovering and characterization of a new bacteriophage is presented, which is capable of infecting specifically the periodontal pathogen *Fusobacterium nucleatum*. In this work, the new phage FnpΦ02 is a lysogenic phage characterized by using transmission electron microscopy, and it establishes the size of this phage's genome. Additionally, its phylogenetic characterization and absorption rate of the bacteriophage is performed.

Although the bacteriophages has been described as related in preventing and/or treating periodontal disease and related diseases such as caries, a specific treatment against one of the most important bacteria in the etiology of periodontal disease, as *Fusobacterium nucleatum* is, has not been established. In the same way, a dental composition comprising bacteriophages specific for this pathogen has not been described.

In this sense, there is a necessity of finding a specific treatment for the most important bacteria in the etiology of periodontal disease, as *Fusobacterium nucleatum*. The present invention disclosed an odontological formula comprising bacteriophages against *Fusobacterium nucleatum* wherein the bacteriophage is a lytic bacteriophage specific for *Fusobacterium nucleatum*. The composition of the invention comprising a lytic bacteriophage specific for *Fusobacterium nucleatum* which presents unique properties regarding what has been previously described, being a specific product for eliminating one of the etiologic agents of periodontal disease, standing out as an effective product for preventing and treating the clinical signs associated with this disease, and even more important, avoiding the risk of problems associated with the treatment of pathogens, such as antibiotic tolerance or side effects, due to the fact that it behaves in a specific way against said microorganisms, therefore resulting in an innocuous product for human beings.

Additionally the composition of the invention comprising a lytic bacteriophage specific for *Fusobacterium nucleatum* serves in preventing extra oral diseases produced or facilitated by systemic dissemination of *Fusobacterium nucleatum* such as Abnormal Pregnancy Outcomes and colorectal cancer.

DESCRIPTION OF THE FIGURES

FIG. 6. Genetic and amino acid characterization of the DNA sequence of FnpΦ02. In a), the result of the ClustalW Analysis is presented, indicating a nucleotide identity of the fragment with phage PA6. The asterisks show the nucleotide identity. Codon STOP from gen gp3 is in bold letters, start codon from gen gp4 is underlined. In b), schematic disposition of the nucleotide identity of PA6 and FnpΦ02 is presented, as well as identity percentages of nucleotide alignment. In c), BlastX Analysis is presented comparing amino acid identities from Gp3 and Gp4 from PA6 with protein sequence of FnpΦ02. Numbers indicate the positions of the amino acid sequence in the protein (first line) and DNA fragment (third line). Second line of the sequence is the consensus sequence, where + corresponds to amino acids from the same family and empty spaces show absence of identity.

FIG. 9. Adsorption test and One Step Growth (OSG) for FnpΦ02. a) Adsorption tests in BHI medium. Adsorption was measured in relation to the percentage of free phages in the supernatant versus time in minutes. b) OSG test, phage's growth curve was measured based in Plaque Forming Units (PFU) for mL obtained in the course of the curve. Black curve is the measure of lysis plaques when adding chloroform. White curve is the measure of lysis plaques without chloroform. Horizontal bar (L) shows the latency period, horizontal bar (E) shows the eclipse period and vertical bar (B), the peak period.

FIG. 10. Adsorption test and One Step Growth (OSG) for FnpΦ11. a) Adsorption tests in BHI medium. Adsorption was measured in relation to the percentage of free phages in the supernatant versus time in minutes. b) OSG test, phage's growth curve was measured based in Plaque Forming Units (PFU) for mL obtained in the course of the curve. In the graph, the curve represented as  corresponds to treatment with chloroform, and  corresponds to the curve resulted from the test without the addition of chloroform.

FIG. 11. Infection curves of FnpΦ02. The axes of the graph correspond to DO regarding incubation time. a) Infection test of F. nucleatum with FnpΦ02, where  corresponds to the infection curve of the phage,  indicates the infection curve of the temperate phage, and  is the infection curve of the phage at a Multiplicity of Infection (MOI from now on) of 0.1. b) Infection curve of F. nucleatum with different MOI of FnpΦ02, where  corresponds to the infection curve of the phage,  to the curve of the temperate phage,  infection curve of the phage at a MOI of 2,  infection curve of the phage at a MOI of 1,  infection curve of the phage at a MOI of 0.1,  infection curve of the phage at a MOI of 0.01,  infection curve of the phage at a MOI of 0.001.

FIG. 14. Comparison of infection curves of FnpΦ02 and FnpΦ02-14. a) Infection curves of FnpΦ02-14 (), FnpΦ02 ( - - ★ - ) and Fusobacterium nucleatum (—→—). The moment of the infection with phages FnpΦ02 and FnpΦ02-14, respectively, is indicated. b) Image of the observation of cultures of F. nucleatum recovered at the end of the curve. Where T1 corresponds to F. nucleatum, T2 to F. nucleatum/FnpΦ02, T3 to F. nucleatum/FnpΦ02-14 and T4 to a culture medium control.

FIG. 15.—Effects of the different treatments on the count of F. nucleatum in different samples. The bar chart presents the count of bacteria F. nucleatum (log (CFU/mL)) from samples 1, 2, 3 and post mortem (axis X) according to the different treatments that have been applied. Where: samples 1 and 2 correspond to samples taken after the bacteria inoculation, samples 3 and post mortem are samples taken after the corresponding treatment. a) Preventive phage treatment. b) MOI 1 phage treatment. c) Phage treatment MOI 0.1. d) Chlorhexidine treatment 0.12%. e) Amoxicillin antibiotic treatment (50 mg/Kg). f) Chlorhexidine treatment 0.12% and amoxicillin.

FIG. 16.—Effects of the different treatments on the count of P. gingivalis in different samples. The bar chart presents the count of bacteria P. gingivalis (log (CFU/mL)) from samples 1, 2, 3 and post mortem (axis X) according to the different treatments that have been applied. Where: samples 1 and 2 correspond to samples taken after the bacteria inoculation, samples 3 and post mortem are samples taken after the corresponding treatment. a) Preventive phage treatment. b) MOI 1 phage treatment. c) Phage treatment MOI 0.1. d) Chlorhexidine treatment 0.12%. e) Amoxicillin antibiotic treatment (50 mg/Kg). f) Chlorhexidine treatment 0.12% and amoxicillin.

FIG. 17.—Effects of the different treatments on the count of total anaerobic bacteria in different samples. The bar chart presents the count of total anaerobic bacteria (log (CFU/mL)) from samples 1, 2, 3 and post mortem (axis X) according to the different treatments that have been applied.

Where: samples 1 and 2 correspond to samples taken after the bacteria inoculation, samples 3 and post mortem are samples taken after the corresponding treatment. a) Preventive phage treatment. b) MOI 1 phage treatment. c) Phage treatment MOI 0.1. d) Chlorhexidine treatment 0.12%. e) Amoxicillin antibiotic treatment (50 mg/Kg). f) Chlorhexidine treatment 0.12% and amoxicillin.

Figure 18:
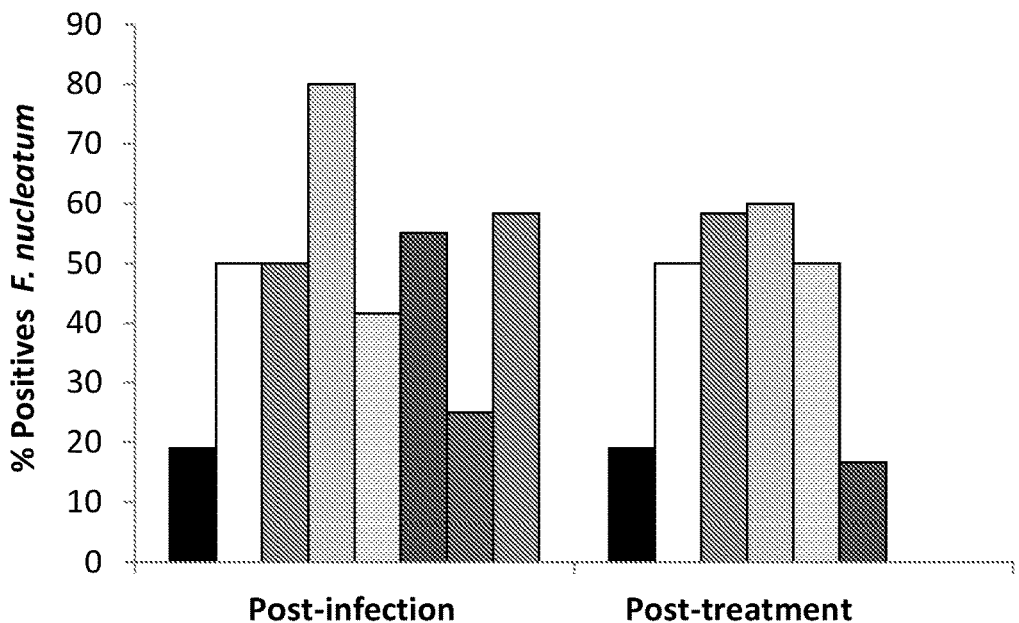

FIG. 18.—Detection by PCR of *F. nucleatum*. The bar chart represents the percentage of *F. nucleatum* detected by PCR in post-infection samples (corresponding to samples 1 and 2), and post-treatment samples (corresponding to samples 3 and post mortem). Detection of *F. nucleatum* was determined according to the different treatments administered: Where ■ corresponds to negative control, □ positive control, ▦ preventive phage, ▦ MOI 1 phage, ▦ MOI 0.1 phage, ▦ chlorhexidine, ▦ antibiotic, ▦ chlorhexidine plus antibiotic.

Figure 19:
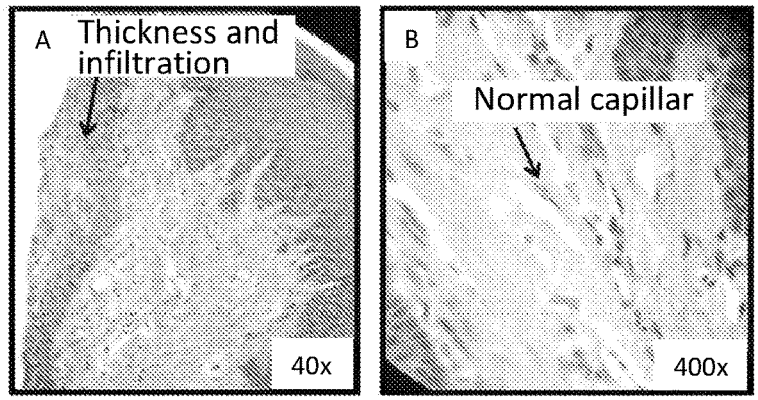

FIG. 19.—Histological sections with hematoxylin-eosin staining of the research group with preventive phage treatment. A) Free keratinized tissue and gingival tissue, magnified 40×. B) Gingival tissue, magnified 400×.

Figure 20:
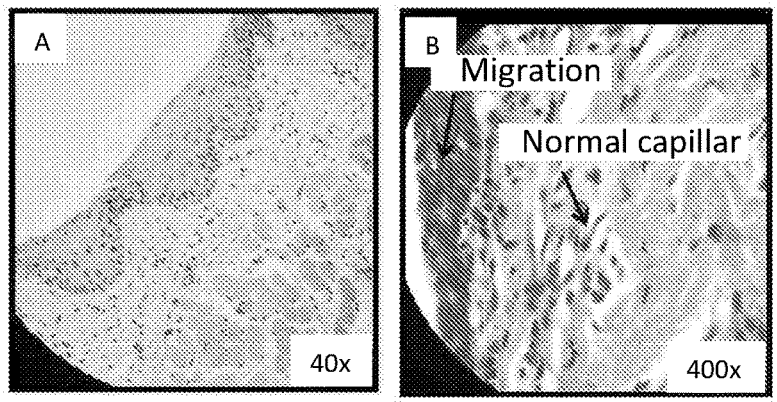

FIG. 20.—Histological sections with hematoxylin-eosin staining of the research group with MOI 0.1 phage treatment. A) Free keratinized tissue and gingival tissue, magnified 40×. B) Gingival tissue, magnified 400×.

Figure 21:
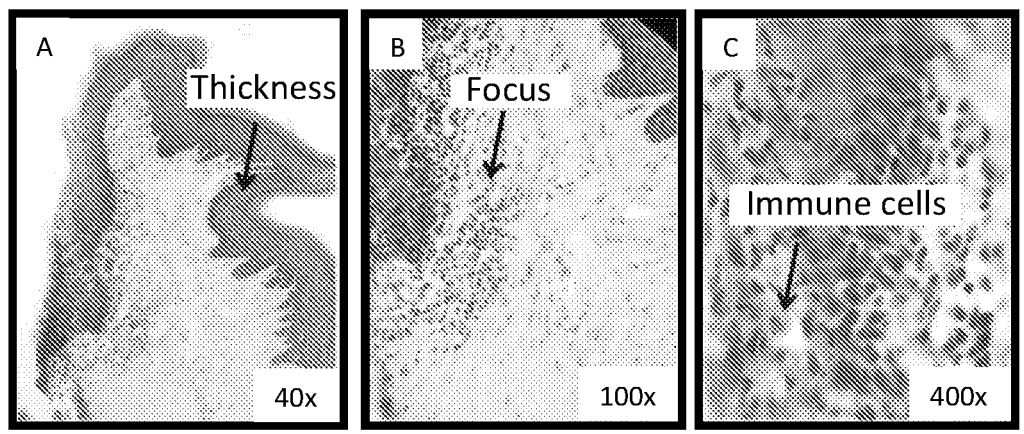

FIG. 21.—Histological sections with hematoxylin-eosin staining of the research group with Chlorhexidine 0.12% treatment. A) Free keratinized tissue and gingival tissue, magnified 40×. B) Gingival tissue associated to keratinized tissue, magnified 100×. C) Gingival tissue, magnified 400×.

Figure 22:
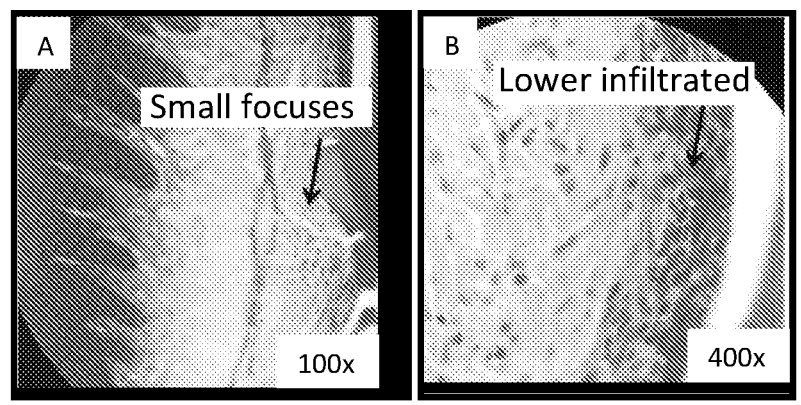

FIG. 22.—Histological sections with hematoxylin-eosin staining of the research group with Amoxicillin (50 mg/Kg) treatment. A) Free keratinized tissue and gingival tissue, magnified 100×. B) Gingival tissue, keratinized epithelium and sulcular epithelium, magnified 400×.

Figure 23:
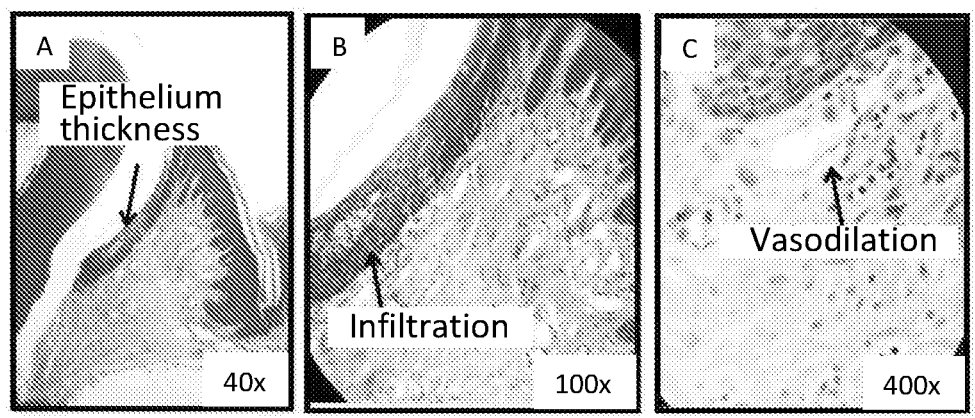

FIG. 23.—Histological sections with hematoxylin-eosin staining of the research group with Chlorhexidine 0.12% and Amoxicillin (50 mg/Kg). A) Complete gum tissue, magnified 40×. B) Free keratinized tissue and gingival tissue, magnified 100×. C) Gingival tissue, magnified 400×.

Figure 24:
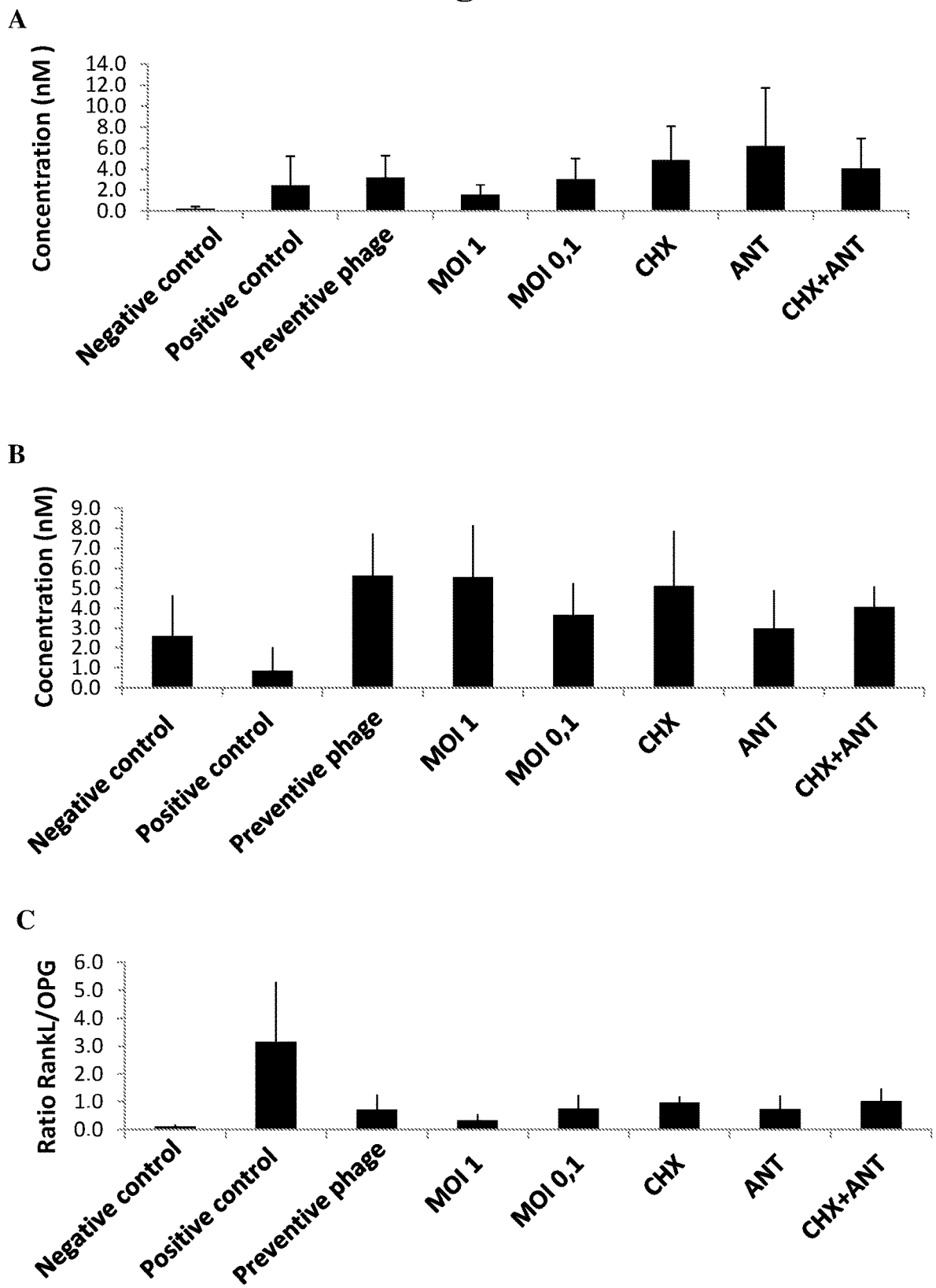

FIG. 24. Quantifying of inflammation mediators of the different research groups by ELISA test. The bar chart represents the concentration of inflammatory mediators in nM (axis y) in the different treatments: negative control, positive control, preventive phage, MOI 1, MOI 0.1, chlorhexidine, antibiotic and chlorhexidine plus antibiotic (axis x). In a), the results of measuring the RANKL inflammatory mediator are presented. In b), the result of measuring the OPG inflammatory mediator is presented. In c), the chart for RANKL/OPG reason is presented.

Figure 25:
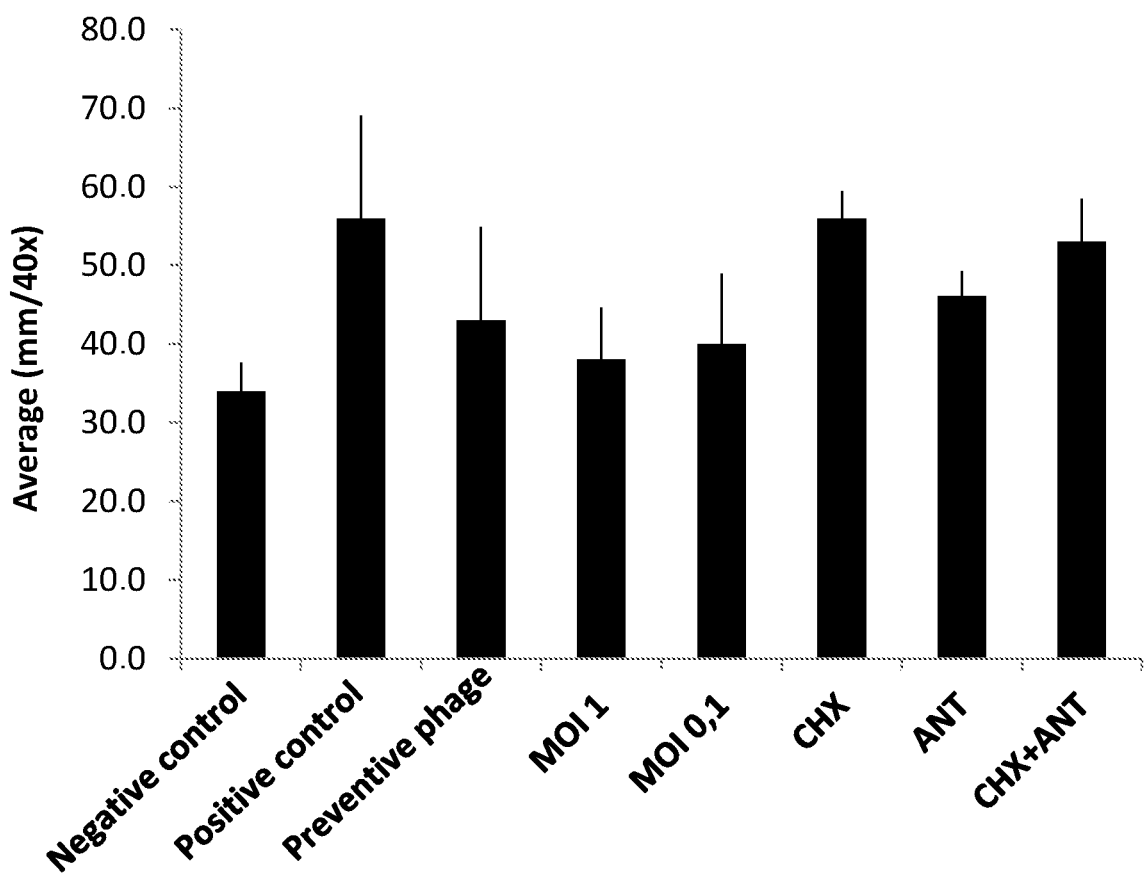

FIG. 25.—Bone loss of rat first molar in the research groups. The chart represents average of bone loss (mm/40×) observed in rat first molars, according to the treatment with: negative control, positive control, preventive phage, MOI 1, MOI 0.1, chlorhexidine, antibiotic y chlorhexidine plus antibiotic (axis x).

Figure 26:
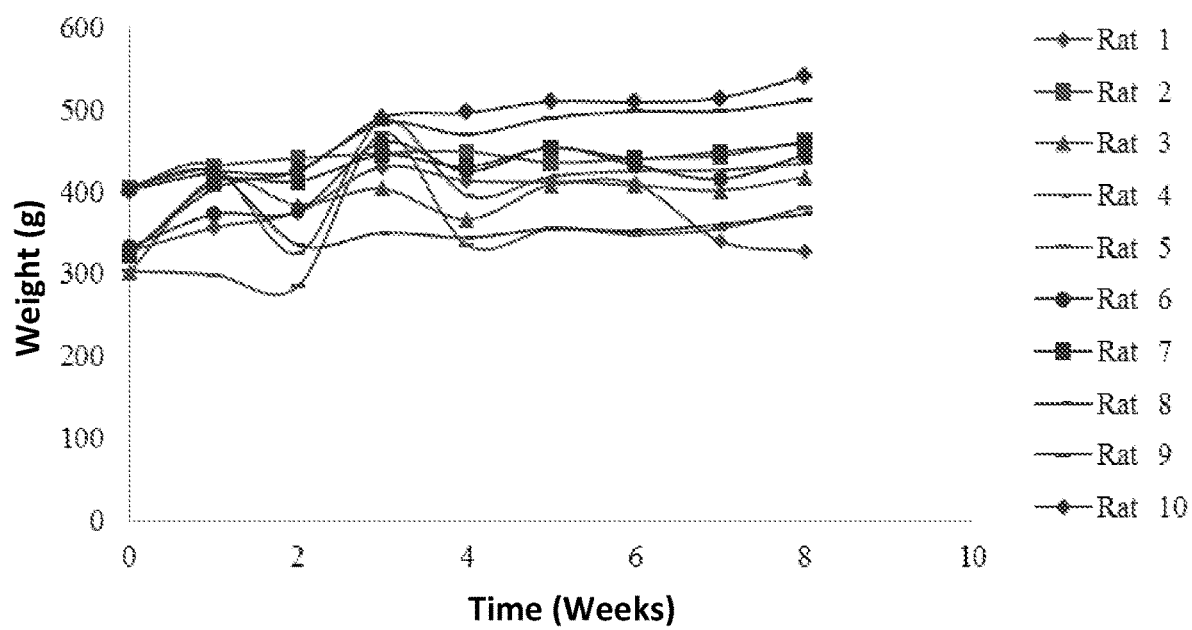

FIG. 26. Weekly weight variation of each subject of the research during treatment period. Subjects assigned with a blue line correspond to the control group, while those in red correspond to the experimental group.

FIG. 27.—Values of markers of liver damage during treatment period. (◆) Control group, (▧) Experimental group. Dotted lines represent the minimum and maximum values described for Sprague-Dawley rats (male) from 9 to 15 weeks, according to Leon and coll.

FIG. 28.—Values of markers of renal damage during treatment period. (◆) Control group, (▧) Experimental group. Dotted lines represent the minimum and maximum values described for Sprague-Dawley rats (male) from 9 to 15 weeks, according to Leon and coll.

DESCRIPTION OF INVENTION

In an embodiment of the invention hereby, it refers to a pharmaceutical composition comprising:
a) a therapeutically effective amount of bacteriophage FnpΦ02-14;
b) one or more pharmaceutically acceptable carrier and/or excipients;
wherein the bacteriophage FnpΦ02-14 is a lytic bacteriophage specific for *Fusobacterium nucleatum*.

In certain embodiments, the pharmaceutical composition further comprises one or more additional lytic bacteriophages specific for *Fusobacterium nucleatum*.

In certain embodiments, the pharmaceutical composition comprises one or more additional lytic bacteriophages specific for *Fusobacterium nucleatum* comprise bacteriophage FnpΦ11 and/or bacteriophage FnnΦ107.

In an embodiment of the invention hereby, it refers to a pharmaceutical composition comprising:
a) a therapeutically effective amount of bacteriophage FnpΦ11;
b) one or more pharmaceutically acceptable carrier and/or excipients;
wherein the bacteriophage FnpΦ11 is a lytic bacteriophage specific for *Fusobacterium nucleatum*

In certain embodiments, the pharmaceutical composition further comprises one or more additional lytic bacteriophages specific for *Fusobacterium nucleatum*.

In certain embodiments, the one or more additional lytic bacteriophages specific for *Fusobacterium nucleatum* comprise bacteriophage FnpΦ02-14 and/or bacteriophage FnnΦ107.

In an embodiment of the invention hereby, it refers to a pharmaceutical composition comprising:
a) a therapeutically effective amount of bacteriophage FnnΦ107;
b) one or more pharmaceutically acceptable carrier and/or excipients;
wherein the bacteriophage FnnΦ107 is a lytic bacteriophage specific for *Fusobacterium nucleatum*

In an embodiment, the pharmaceutical composition further comprises one or more additional lytic bacteriophages specific for *Fusobacterium nucleatum*.

In an embodiment, the one or more additional lytic bacteriophages specific for *Fusobacterium nucleatum* comprise bacteriophage FnpΦ02-14 and/or bacteriophage FnpΦ11.

In an embodiment of the invention hereby, it refers to a pharmaceutical composition comprising:
a) a therapeutically effective amount of three bacteriophages;
b) one or more pharmaceutically acceptable carrier and/or excipients;
wherein the three bacteriophage are lytic bacteriophage specific for *Fusobacterium nucleatum*.

In an embodiment, the pharmaceutical composition comprises three lytic bacteriophages which are FnpΦ02-14, FnpΦ11, and FnnΦ107.

The invention hereby further relates to a pharmaceutical composition as described herein for use as a medicament.

In certain embodiments the pharmaceutical composition as described herein are for use as a medicament for preventing and/or treating diseases associated with *Fusobacterium nucleatum* in a subject.

In certain embodiments the diseases associated with *Fusobacterium nucleatum* in a subject corresponds to diseases of the oral cavity.

In an embodiment, the disease associated with *Fusobacterium nucleatum* is an extra oral diseases produced by systemic dissemination of *Fusobacterium nucleatum*.

In an embodiment of the invention hereby, it refers to a the pharmaceutical composition as described herein are for use as a medicament for preventing and/or treating diseases associated with *Fusobacterium nucleatum* in a subject wherein the diseases associated with *Fusobacterium nucleatum* are periodontal disease, intestinal diseases, colorectal cancer or premature labor or complications during pregnancy.

The invention hereby further relates to the use of a pharmaceutical composition as described herein for the manufacture of a medicament.

In certain embodiments the use of a pharmaceutical composition as described herein are for the manufacture of a medicament for preventing and/or treating diseases and/or condition associated with *Fusobacterium nucleatum* in a subject.

In an embodiment, the disease associated with *Fusobacterium nucleatum* is an extra oral diseases produced by systemic dissemination of *Fusobacterium nucleatum*.

In certain embodiments the diseases and/or condition associated with *Fusobacterium nucleatum* in a subject corresponds to diseases of the oral cavity.

In an embodiment of the invention hereby, it refers to the use of a pharmaceutical composition as described herein are for the manufacture of a medicament for preventing and/or treating diseases associated with *Fusobacterium nucleatum* in a subject wherein the diseases associated with *Fusobacterium nucleatum* are periodontal diseases, intestinal diseases, colorectal cancer or premature labor or complications during pregnancy.

The invention hereby further relates methods for preventing and/or treating diseases associated with *Fusobacterium nucleatum* in a subject in need thereof, comprising administering to a subject a pharmaceutical composition as described herein.

In an embodiment of the invention hereby, it refers to a method for preventing and/or treating diseases associated with *Fusobacterium nucleatum* in a subject in need thereof, comprising administering to the subject a therapeutically effective amount of a pharmaceutical composition comprising bacteriophage FnpΦ02-14 and one or more pharmaceutically acceptable carriers and/or excipients, wherein the bacteriophage FnpΦ02-14 is a lytic bacteriophage specific for *Fusobacterium nucleatum*.

In an embodiment, the method of the invention comprises administering to the individual a therapeutically effective amount of the composition, wherein the composition comprises one or more additional lytic bacteriophages specific for *Fusobacterium nucleatum*.

In an embodiment, the method of the invention comprises administering to the individual a therapeutically effective amount of one or more additional lytic bacteriophages specific for *Fusobacterium nucleatum*, wherein the bacteriophages comprising bacteriophage FnpΦ11 and/or bacteriophage FnnΦ107.

In an embodiment of the invention hereby, it refers to a method for preventing and/or treating diseases associated with *Fusobacterium nucleatum* in a subject in need thereof, comprising administering to the subject a therapeutically effective amount of a pharmaceutical composition comprising bacteriophage FnpΦ11 and one or more pharmaceutically acceptable carriers and/or excipients, wherein the bacteriophage FnpΦ11 is a lytic bacteriophage specific for *Fusobacterium nucleatum*.

In an embodiment, the method of the invention comprises administering to the individual a therapeutically effective amount of a composition, wherein the composition comprises one or more additional lytic bacteriophages specific for *Fusobacterium nucleatum*.

In an embodiment, the method of the invention comprises administering to the individual a therapeutically effective amount of one or more additional lytic bacteriophages specific for *Fusobacterium nucleatum*, wherein the bacteriophages comprise bacteriophage FnpΦ02-14 and/or bacteriophage FnnΦ107.

In an embodiment of the invention hereby, it refers to a method for preventing and/or treating diseases associated with *Fusobacterium nucleatum* in a subject in need thereof, comprising administering to the subject a therapeutically effective amount of a pharmaceutical composition comprising bacteriophage FnnΦ107 and one or more pharmaceutically acceptable carriers and/or excipients, wherein the bacteriophage FnnΦ107 is a lytic bacteriophage specific for *Fusobacterium nucleatum*.

In an embodiment, the method of the invention comprises administering to the individual a therapeutically effective amount of the composition, wherein the composition comprises one or more additional lytic bacteriophages specific for *Fusobacterium nucleatum*.

In an embodiment, the method of the invention comprises administering to the individual a therapeutically effective amount of the one or more additional lytic bacteriophages specific for *Fusobacterium nucleatum*, wherein the bacteriophages comprise bacteriophage FnpΦ11 and/or bacteriophage FnpΦ02-14.

In an embodiment of the invention hereby, it refers to a method for preventing and/or treating diseases associated with *Fusobacterium nucleatum* in an individual in need thereof, comprising administering to the individual a therapeutically effective amount of a pharmaceutical composition comprising three lytic bacteriophages specific for *Fusobacterium nucleatum* and one or more pharmaceutically acceptable carriers and/or excipients.

In an embodiment, the method of the invention comprises administering to the individual a therapeutically effective amount of the three lytic bacteriophages, wherein the bacteriophages are FnpΦ02-14, FnpΦ11, and FnnΦ107.

In an embodiment, the method of the invention comprises administering to the individual a therapeutically effective amount of lytic bacteriophages specific against *Fusobacterium nucleatum*, wherein the bacteriophages are present in equal or different concentrations, in the range from $10^4$ to $10^{12}$ CFU/mL.

In an embodiment, the method of the invention comprises administering to the individual a therapeutically effective amount of the lytic bacteriophages specific against *Fusobacterium nucleatum*, FnpΦ02-14, FnpΦ11 and FnnΦ107, which are present in concentrations of $10^8$, $10^{10}$ and $10^8$ CFU/mL, respectively.

In an embodiment, the method of the invention comprises administering to the individual a therapeutically effective amount of the three lytic bacteriophages specific against *Fusobacterium nucleatum*, comprising FnpΦ02-14, FnpΦ11 and FnnΦ107, wherein the bacteriophages have been deposited at the International Depositary Authority of Canada (IDAC) under the deposit numbers IDAC 300115-01, IDAC 300115-02 and IDAC 300115-03, respectively.

In an embodiment of the invention hereby, it refers to a method for preventing and/or treating diseases associated with *Fusobacterium nucleatum*, wherein the disease associated with *Fusobacterium nucleatum* corresponds to diseases of the oral cavity.

In an embodiment of the invention hereby, it refers to a method for preventing and/or treating diseases associated with *Fusobacterium nucleatum* wherein the disease associated with *Fusobacterium nucleatum* is periodontal disease.

In an embodiment, the disease associated with *Fusobacterium nucleatum* is an extra oral diseases produced by systemic dissemination of *Fusobacterium nucleatum*.

In an embodiment of the invention hereby, it refers to a method for preventing and/or treating diseases associated with *Fusobacterium nucleatum* wherein the disease associated with *Fusobacterium nucleatum* correspond to intestinal diseases.

In an embodiment of the invention hereby, it refers to a method for preventing and/or treating diseases associated with *Fusobacterium nucleatum*, wherein the disease associated with *Fusobacterium nucleatum* is colorectal cancer.

In an embodiment of the invention hereby, it refers to a method for preventing and/or treating diseases associated with *Fusobacterium nucleatum*, wherein the disease associated with *Fusobacterium nucleatum* is premature labor or complications during pregnancy.

The invention hereby refers to a pharmaceutical composition comprising one or more lytic bacteriophages specific against *Fusobacterium nucleatum* corresponding to bacteriophages selected from the group consisting of FnpΦ02-14, FnpΦ11 and FnnΦ107, wherein said specific bacteriophages are present in equal or different concentrations, in a range from $10^4$ to $10^{12}$ UFP/mL, more specifically equal or different concentrations, in a range from $10^6$ to $10^{10}$ UFP/mL.

In an embodiment of the invention hereby, it refers to a pharmaceutical composition comprising a mixture of three lytic bacteriophages specific against *Fusobacterium nucleatum* FnpΦ02-14, FnpΦ11 and FnnΦ107, wherein bacteriophages FnpΦ02-14, FnpΦ11 and FnnΦ107 are preferably in a concentration of $10^8$, $10^{10}$ and $10^8$ UFP/mL, respectively. Specific bacteriophages against *Fusobacterium nucleatum* of the invention hereby correspond to those that have been deposited in the International Depositary Authority of Canada (IDAC) under deposit numbers IDAC 300115-01, IDAC 300115-02 and IDAC 300115-03, respectively.

In an embodiment of the invention hereby, the specific lytic bacteriophages have Multiplicity of Infection (MOI from now on) of 0.1, preferably a MOI of 1.

In the invention hereby, it is to be understood as a pharmaceutically acceptable carrier those carriers which are usually used in the pharmaceutical industry or oral hygiene industry in order to generate presentations of oral, inhalation or topic dosage as those described right below. Pharmaceutically acceptable carriers are, among others, and not limited to, purified water, ethyl alcohol, isopropyl alcohol, among others, and are useful to release bacteriophages in the place of infection.

In the invention hereby, it is to be understood as a pharmaceutically acceptable excipient those excipients which are usually used in the pharmaceutical industry or oral hygiene industry in order to obtain dosage formulas as those described right below. Pharmaceutically acceptable excipients are, among others, and not limited to, sweeteners, artificial flavoring, and coloring.

The invention hereby may also comprise preservatives, antioxidants and/or antimicrobial agents.

Pharmaceutical composition of the invention hereby is formulated as an oral dosage form, such as liquid solution, mouthwash, pastes, toothpaste, dissolving films, spray, dental floss, gels, varnish, crystals, micro and nanoparticles, pills, tablets, capsules, syrups, suspensions, liquid suspension, composites, resins, capping, meshes, freeze-dried, powder, coated metal implants, coated porcelain crowns, silicone, sealants, cementation elements, adhesion elements or any carrier that will allow releasing bacteriophages inside the mouth. The pharmaceutical composition is preferably formulated as a mouthwash.

Pharmaceutical composition of the invention hereby is formulated as an inhalational dosage form, such as aerosol, inhaler, nebulizer, vaporizer.

Pharmaceutical composition of the invention hereby is formulated as a topic dosage form, such as cream, liniment, balm, lotion or ointment.

Pharmaceutical composition of the invention is useful in preventing and treating periodontal disease, and it is useful for preparing a useful medicament for preventing and treating diseases associated with *Fusobacterium nucleatum*, specifically for preventing and treating oral cavity diseases.

An embodiment of the invention hereby refers to the use of a pharmaceutical composition for preparing a useful medicament for preventing and treating periodontal disease.

Lytic bacteriophages FnpΦ02-14, FnpΦ11 and FnnΦ107 were isolated from saliva samples extracted from healthy and sick individuals (Dental Clinic in Andrés Bello University and Barros Luco Hospital). After processing them, the bacteriophage was isolated from its corresponding lysis plaque.

Isolated lytic bacteriophages present an activity which is specific for *F. nucleatum*. In a particular way, phage FnpΦ11 is effective for all of the *F. nucleatum* species that have been examined, while phage FnnΦ107 is only effective for *nucleatum* subspecies.

Structurally, bacteriophage FnpΦ02-14 presents a binary symmetry composed by a head and a filamentous tail, phage FnpΦ11 presents binary symmetry composed by an icosahedral head and non-contractile tail, and FnnΦ107 presents an icosahedral head and non-contractile tail.

Bacteriophages FnpΦ02-14, FnpΦ11 and FnnΦ107 were evaluated by applying a concentration of $10^6$, $10^8$ and $10^{10}$ UFP/mL, respectively, on Sprague Dawley rat models. The mixture of all of the three bacteriophages affects the microbiological count of bacteria associated with periodontal disease, such as *Fusobacterium nucleatum* and *Porphyromonas gingivalis*. Additionally, the mixture of the three bacteriophages improves and keeps the periodontal integrity parameters: adhesion level, depth of periodontal pocket (mm), observation of the alveolar crest and gum/tooth index. On the other hand, the composition of the invention hereby, composed by the three bacteriophages, minimizes the inflammatory response of infected rats and diminishes reabsorption and bone loss of alveolar bone.

A particular embodiment of the invention comprises a composition comprising a mixture of isolated lytic bacteriophages formulated as a dental use formula. Specifically, the composition comprises an adequate quantity of bacteriophages for *F. nucleatum* FnpΦ02-14, FnpΦ11 and FnnΦ107, together with the base or carrier of dental composition.

When a dental use composition is mentioned in the invention hereby, it refers to, and not limited to, the following kinds of composition: mouthwash, toothpaste, dissolving films, spray, dental floss, gels, varnish, micro and nanoparticles, pills, capsules, suspensions, composites, resins, capping, meshes, freeze-dried, powder, coated metal implants, coated porcelain crowns, silicone, sealants, cementation elements, adhesion elements or any carrier that will allow releasing bacteriophages inside the mouth.

When the invention hereby refers to the capacity of infection of the bacteriophages on the host cell, it is written in a numeric form and based in the multiplicity of infection concept (MOI from now on). Multiplicity of infection is defined as the quantity of bacteria or infection agents infecting a target or host cell.

On the other hand, *Fusobacterium* genus has been described not only as an important precursor of oral cavity diseases, but also as a main factor in the development of other kind of extra oral diseases. Thus, *Fusobacterium* is the most isolated oral bacteria from extra oral infections, including infections in blood, brain, respiratory system, lung, liver, articulations, abdominal tract, urogenital tract and abscesses. Even more, *F. nucleatum* is the anaerobic bacteria which is more commonly isolated in the intrauterine infections, and has been associated with complications during pregnancy, including premature labor and low weight in newborns (Benoit S. et al., Curr. Issues Mol. Biol., Vol. 13, pages 25-36, 2011).

In scientific articles, the existence of high levels of *F. nucleatum* in colorectal carcinoma biopsy samples has been described, being even higher in biopsies related to metastasis in lymphatic nodules (Castellarin M. et al, Genome Res., Vol. 22(2), pages 299-306, 2012). Based on this, *F. nucleatum* is starting to be considered a risk factor for the progression of adenoma to cancer, possibly by using mechanisms of immune cell recruitment which will infiltrate the tumor, generating an inflammatory-favorable micro environment, which can lead to progression of colorectal neoplasm, causing colorectal carcinogenesis and showing a new infectious etiology for this kind of cancer (Flanagan L. et al, Eur J Clin Microbiol Infect Dis. Vol. 33 (8), pages 1381-1390, 2014; Kostic A D. et al, Cell Host Microbe., Vol. 14(2), pages 207-215, 2013). In the same way, the infection of *F. nucleatum* in the gastrointestinal tract has been pointed out as a factor for the development of intestinal inflammatory disease, as well as responsible for acute appendicitis cases (Allen-Vercoe E. et al, Gut Microbes, Vol. 2(5), 2011; Swidsinski A., et al., Genome Res., Vol. 22(2), pages 292-298.2011).

The important presence of periodontal disease in pregnant women has been described over the years as a factor for pregnancy complications, such as premature birth and low weight in newborns (Ercan E. et al, Acta Odontol Scand. Vol. 71, 2013). Specifically, some researches indicate that *F. nucleatum* is related to intra-amniotic infections and premature births, presenting an oral origin. Even more, a report was presented about complications during pregnancy with the result of fetal death, caused by an intrauterine infection of *F. nucleatum*. (Han Y W. et al, Obstet Gynecol., Vol. 115, pages 442-445., 2010).

Clinic reports of complications of diseases due to infections of *F. nucleatum* confirm the need of an effective treatment against this pathogen.

An embodiment of the invention comprises the mixture of bacteriophages Fnp$\Phi$02-14, Fnp$\Phi$11 and Fnn$\Phi$107 to prepare pharmaceutically acceptable compositions, which are useful in the prevention and/or treatment of diseases related to *Fusobacterium* infection, such as colorectal cancer, intestinal infections, complications during pregnancy, such as premature birth and low weight in newborns, intrauterine infection, vertebral osteomyelitis and discitis, among others.

An embodiment of the invention comprises a method for preventing and/or treating diseases associated with *Fusobacterium nucleatum* in a subject in need thereof, comprising administering to the subject a therapeutically effective amount of a pharmaceutical composition comprising one or more lytic bacteriophage specific against *Fusobacterium nucleatum* and one or more pharmaceutically acceptable carriers and/or excipients.

An embodiment of the invention comprises a method for preventing and/or treating diseases associated with *Fusobacterium nucleatum* in a subject in need thereof, wherein the method comprises administering a composition comprising one or more lytic bacteriophage specific against *Fusobacterium nucleatum* selected from Fnp$\Phi$02-14, Fnp$\Phi$11 and Fnn$\Phi$107 bacteriophages.

An embodiment of the invention comprises a method for preventing and/or treating diseases associated with *Fusobacterium nucleatum* in a subject in need thereof, wherein the method comprises administering a composition comprising two lytic bacteriophage specific against *Fusobacterium nucleatum* comprising the Fnp$\Phi$02-14 and Fnp$\Phi$11 bacteriophages, or the Fnp$\Phi$02-14 and Fnn$\Phi$107 bacteriophages, or more preferably the method comprises administering a composition comprising three lytic bacteriophage specific against *Fusobacterium nucleatum* wherein said lytic bacteriophage specific against *Fusobacterium nucleatum* comprising the Fnp$\Phi$11, Fnp$\Phi$02-14 and Fnn$\Phi$107 bacteriophages.

Wherein the method of the invention comprises administering a composition comprising, one, two or three lytic bacteriophage specific against *Fusobacterium nucleatum* comprising Fnp$\Phi$02-14, Fnp$\Phi$11 and Fnn$\Phi$107 bacteriophages, and they correspond to which have been deposited at the International Depositary Authority of Canada (IDAC) under the deposit numbers IDAC 300115-01, IDAC 300115-02 and IDAC. 300115.-03, respectively.

An embodiment of the invention comprises a method for preventing and/or treating diseases associated with *Fusobacterium nucleatum* in a subject in need thereof, wherein the method comprises administering to the subject a therapeutically effective amount of a pharmaceutical composition comprising one or more lytic bacteriophage specific against *Fusobacterium nucleatum* and one or more pharmaceutically acceptable carriers and/or excipients, wherein the disease associated with *Fusobacterium nucleatum* is selected from periodontal disease, colorectal cancer, abnormal pregnancy outcomes or wherein the disease associated with *Fusobacterium nucleatum* is premature labor and complications during pregnancy.

Periodontal diseases as defined here corresponds to periodontitis and/or and gingivitis.

EXAMPLES

Example 1: Isolation of Bacteriophages Specific Against *Fusobacterium nucleatum*

In this example, methodology and results associated with extraction and isolation of bacteriophages specific against *Fusobacterium nucleatum* are presented, which are obtained from saliva samples extracted from healthy and sick individuals and waste water from dental chairs spittoons from Dental Clinic at the Andrés Bello University and Barros Luco Hospital.

Collected samples are centrifuged for 5 min. at 10,000 g, and after that, they are filtered by a filtration unit using a 0.45 μm syringe (Advantec, Japan). Later, 500 of the filtered samples are added to 5 mL of a Brain Heart Infusion (BHI, 37 g/L) culture medium of the host cell *F. nucleatum* to an optical density ($OD_{600}$) of 0.15-0.2. After 24 hours of the culture incubation, this is centrifuged at 10,000 g for 3 min. and the supernatant is filtered again with a 0.45 filter. The suspension obtained as a result is called "enriched".

In the next phase, it is necessary to determine if there resultant suspension ("enriched") contains viral particles. In order to do this, a spot test is done in a lawn of the indicated strain, according to what has been previously described by Chang and coll. (2005). Briefly, *F. nucleatum* is cultivated in the conditions previously described during all night (O/N), where 1 mL of this culture is mixed with 7 mL of semisolid agar (0.8% agar) and is poured on a plate of BHI in order to make a lawn in soft agar. One drop of 5 μL of the "enriched" is put on the plate and incubated for 24 to 48 hours. Sensibility of the bacteria in this possible lysate is determined by the appearance of growth free zone.

Figure 1:
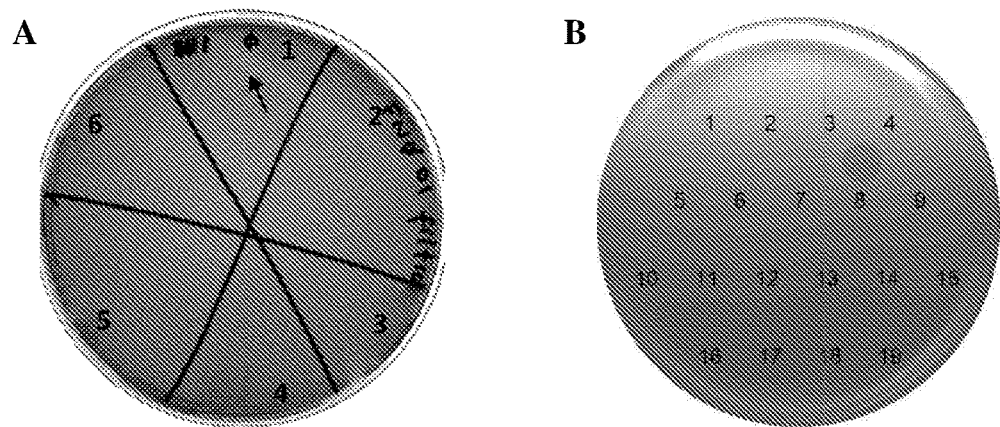
FIG. 1. Search of bacteriophages for *F. nucleatum*. a) Spot-test with samples obtained from people without periodontal disease (1-6) in a semi-solid agar (0.8%) of the host cell. The arrow points at the growth inhibition in sample 1, named FnpΦ02. b) Spot-test with samples obtained from waste water of dental chairs (1-9) or saliva samples (10-19) in a semi-solid agar (0.8%) of E *nucleatum*. Numbers identify the different samples.
Figure 2:
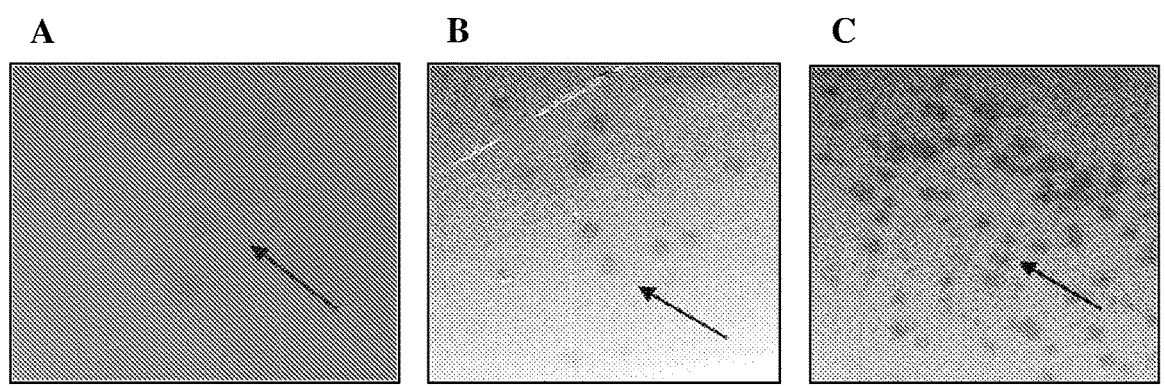
FIG. 2. Observation of lysis plaques of isolated bacteriophages for *F. nucleatum*. A) Lysis plaque of phage FnpΦ02. B) Lysis plaque of phage FnpΦ11. C) Lysis plaque of phage FnpΦ107. The dates show an example of one of the lysis plaques corresponding to each phage.

The first detected bacteriophage was isolated from a saliva sample of a 24-year-old, periodontally healthy patient. Detection of bacteriophage revealed as a halo of inhibition of bacterial growth (FIG. 1a). This phage was named FnpΦ02, which presented heterogeneous lysis plaques (clean and turbid), diameter sized 0.5-1 mm (FIG. 2a). The second isolated bacteriophage, named FnpΦ11, was isolated from a waste water sample from a dental chair in Barros Luco Hospital (FIG. 1b), and presented clean lysis plaques, diameter sized 0.5-1 mm (FIG. 2b). Finally, the third bacteriophage was isolated from a 54-year-old patient, diagnosed with chronic periodontitis, and was named FnnΦ107. This phage presented clean lysis plaques, diameter sized 1-1.5 mm (FIG. 2c). The first macroscopic analysis of lysis plaques suggested that FnpΦ02 is a temperate phage, while FnpΦ11 and FnnΦ107 are lytic phages.

In case of a zone with bacterial growth inhibition, titration of this possible lysate is performed, in order to obtain lysis plaques. For bacteriophages titration, the previously obtained lysate is taken, diluted in a tenfold dilution in a breeding ground BHI and 5 μL of each dilution were plated on a soft agar lawn of the sensible bacteria. The number of lysis plates (UFP) was counted after incubation in classified according to clarity in turbid or clean. Lysis plaques were extracted from the lawn and spread.

$$UFP/mL = \frac{UFP \times \text{Dilution factor} \times 1000 \text{ μL}}{\text{Plated volume (μL)}}$$

Example 2: Determining the Specificity of the Host of the Isolated Bacteriophages FnpΦ02, FnpΦ1 and FnnΦ07

In this example, the specificity of the isolated bacteriophages is presented, in order to find out if they have one only host or correspond to phages with a wide spectrum of infection. In order to find it out, different bacteria from oral flora, normal extra-oral flora and pathogen strains are infected by making a lawn in soft agar of the different bacteria used in this research (Table 1). On the set up lawn, one drop of 5 μL of the lysates is put, and incubated for 24 to 48 hours in anaerobiosis, aerobiosis or capnophilia, as appropriate. The result is considered to be positive when a growth inhibition zone is generated.

In table 1, the results of determining the specificity of the isolated phages against different bacteria species and subspecies are presented, showing growth inhibition (+), absence of growth inhibition (−) and the number of tested strains (n).

The results showed that phages are specific for *F. nucleatum*. Phage FnpΦ11 is effective for all of the *F. nucleatum* species that have been examined, while phage FnnΦ107 is only effective for *nucleatum* subspecies (Table 5), something that will allow us to use it in the phage typification of new strains.

TABLE 1

Results of specificity of the host of phages Fnpφ02, Fnpφ11 and Fnnφ107.

| Strains | Fnpφ02 | Fnpφ11 | Fnnφ107 |
|---|---|---|---|
| Gram-negative of the oral cavity | | | |
| *Fusobacterium nucleatum* ATCC25586 | + | + | + |
| *F. nucleatum* subsp. *nucleatum* (3) | + | + | + |
| *F. nucleatum* subsp. *polymorphum* | + | + | − |
| *Fusobacterium necrophorum* ATCC25286 | − | − | − |
| *A. actinomycetemcomitans* serotype b (3) | − | − | − |
| *A. actinomycetemcomitans* serotype c (3) | − | − | − |
| *Bacteroides vulgatus* ATCC8482 | − | − | − |
| *Bacteroides ureolyticus* | − | − | − |
| *Porphyromonas gingivalis* ATCC33277 | − | − | − |
| *Porphyromonas gingivalis* (3) | − | − | − |
| *Porphyromonas endodontalis* | − | − | − |
| *Prevotella intermedia* (3) | − | − | − |
| *Prevotella nigrescens* (2) | − | − | − |
| Gram-positive of the oral cavity | | | |
| *Streptococcus mutans* ATCC25175 | − | − | − |
| *Streptococcus sanguinis* | − | − | − |
| *Propionibacterium acnes* (4) | − | − | − |
| *Actinomyces naeslundii* | − | − | − |
| *Eubacterium limosun* | − | − | − |
| *Eubacterium lentum* | − | − | − |
| Other Gram-positive | | | |
| *Streptococcus pyogenes* (2) | − | − | − |
| *Streptococcus agalactiae* (2) | − | − | − |
| *Staphylococcus aureus* ATCC43330 | − | − | − |
| *Staphylococcus aureus* (2) | − | − | − |
| *Staphylococcus epidermidis* (3) | − | − | − |
| *Staphylococcus epidermidis* ATCC14990 | − | − | − |
| Other Gram-negative | | | |
| *Escherichia coli* (2) | − | − | − |
| *Salmonella Typhimurium* | − | − | − |
| *Proteus vulgaris* (2) | − | − | − |
| *Proteus mirabilis* (2) | − | − | − |
| *Klebsiella pneumoniae* (2) | − | − | − |
| *Klebsiella oxytoca* (2) | − | − | − |

+, indicates growth inhibition
−, indicates without growth inhibition
(n), number of tested strains

Example 3: Structural and Genetic Characterization of the Bacteriophages

Structural Characterization

Phages are characterized according to their structure by using electronic microscopy. In order to do this, 50 mL of the lysate are deposited in a Sorvall RC 90 ultracentrifuge, using the AH-629/17 rotor at 30,000×g for 3 h. The supernatant is eliminated and the sediment is resuspended in 5 μL of bidistilled water. One drop of the suspension of bacteriophages is attached to 2.5% glutaraldehyde at room temperature for 20 min. This suspension is set in a grid covered with parlodion/coal and left for 60 sec. Then, one drop of aqueous uranyl acetate at 2% and we let it work for 60 sec. Once the grid is dry, it is observed in a Philips Tecnai 12 BioTwin transmission electron microscopy at 80 kV.

Figure 3:
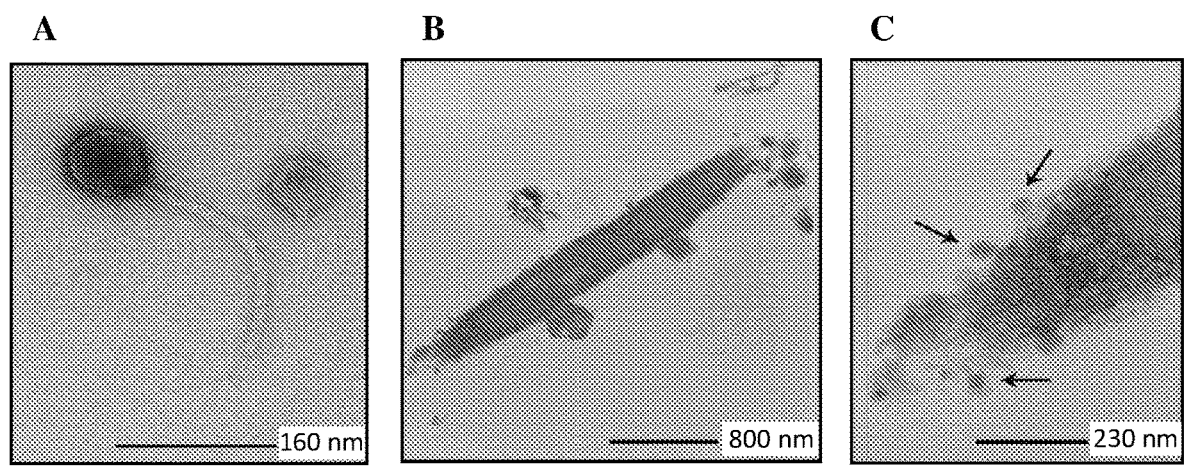
FIG. 3. Transmission electron microscopy (TEM) of phage FnpΦ02. In a), an image of transmission electron microscopy of the main structure of phage FnpΦ02 is presented, showing its icosahedral head and its filamentous tail. In b), an image of TEM is presented, where the lysis process of *F. nucleatum* appears. In c), the appearance of new viral particles coming from the ends of the bacteria (black arrows) is indicated. Horizontal bar indicates the scale in nanometers.
Figure 4:
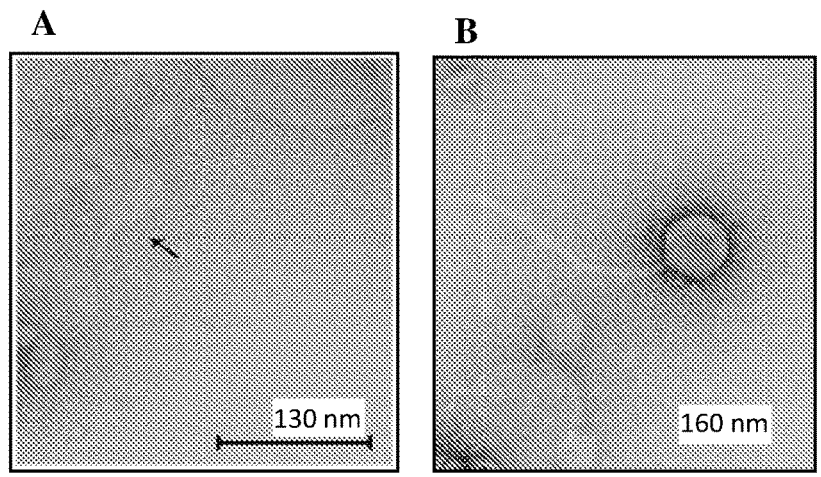
FIG. 4. Transmission electron microscopy (TEM) of phages FnpΦ11 and FnpΦ107. In a), an image of transmission electron microscopy of the phage FnpΦ11 is presented, differing by its binary symmetry, composed by icosahedral head and filamentous short tail. In b), the general structure of phage FnΦ107 is presented, composed by icosahedral head and filamentous long tail.

The results show that FnpΦ02 presents a binary symmetry, composed by an icosahedral head of 50-60 nm and a filamentous, non-contractile tail of 150 nm long, approximately (FIG. 3a). Electron microscopy of FnpΦ11 indicates that it presents a binary symmetry, composed by an icosahedral head of 77 nm and a non-contractile tail of 55 nm long (FIG. 4a). And FnpΦ107 also presents an icosahedral head of 90 nm and a non-contractile tail of 346 nm (FIG. 4b).

Genetic Characterization

Genetic characterization is carried out for every isolated bacteriophage. General procedure characterization consists of purifying the genome of the phage from 10 mL of lysate. To this volume, 10 μL de DNasa I (10 mg/mL) is added, and it is incubated for 30 minutes at 37° C. Then, 4 mL of precipitant solution are added (NaCl 3.3 M and PEG 6000 0.055 M) and it is incubated in ice for 1 hour. It is centrifuged at 10,000×g for 10 min. at 4° C., and the supernatant is discarded. The sediment is resuspended in 600 μL of a CSM solution (NaCl 0.1 M, MgSO$_4$ 7H$_2$O 8 mM, Tris 0.05 M pH 7.5 and 0.01% gelatin). Then, a volume of Phenyl Acid:Chloroform:Iso-amyl Alcohol (3:1:0.05) is added, and it is centrifuged at 16,000×g for 10 min. The DNA contained on the watery phase is precipitated with an isopropanol volume and incubated at −80° C. for 15 min. Then, it is centrifuged at 16,000×g for 10 min., and the supernatant is discarded. The precipitate is washed with 500 μL of cold ethanol 70%, centrifuged for 5 minutes at 16,000×g, the supernatant is eliminated and it is left to dry at room temperature. Finally, the bacteriophage genome is resuspended in 50 μL of distilled, sterile H$_2$O and kept at 4° C. until it is used. In the second place, the purified genome is treated with enzymes DNasaI or RNasaA, in order to determine if the genome of the phage corresponds to DNA or RNA. Afterwards, it is treated with restriction endonucleases of type II EcoRI, XbaI, PstI, KpnI, DraI, BamHI, HindIII and Sau3AI for 3 h at 37° C., visualizing the restriction pattern in agarose gel at 1.5% using the molecular mass marker 1 Kb DNA ladder and Lambda/HindIII marker. The used protocol is the following: 6.5 μL of nuclease-free water, 1.0 μL de Buffer enzyme 10×, 0.5 μL Enzyme (10 U/μL) and 2.0 μL of the phage's DNA (200 ng/μL approximately).

Genetic Characterization Phage FnpΦ02

Figure 5:
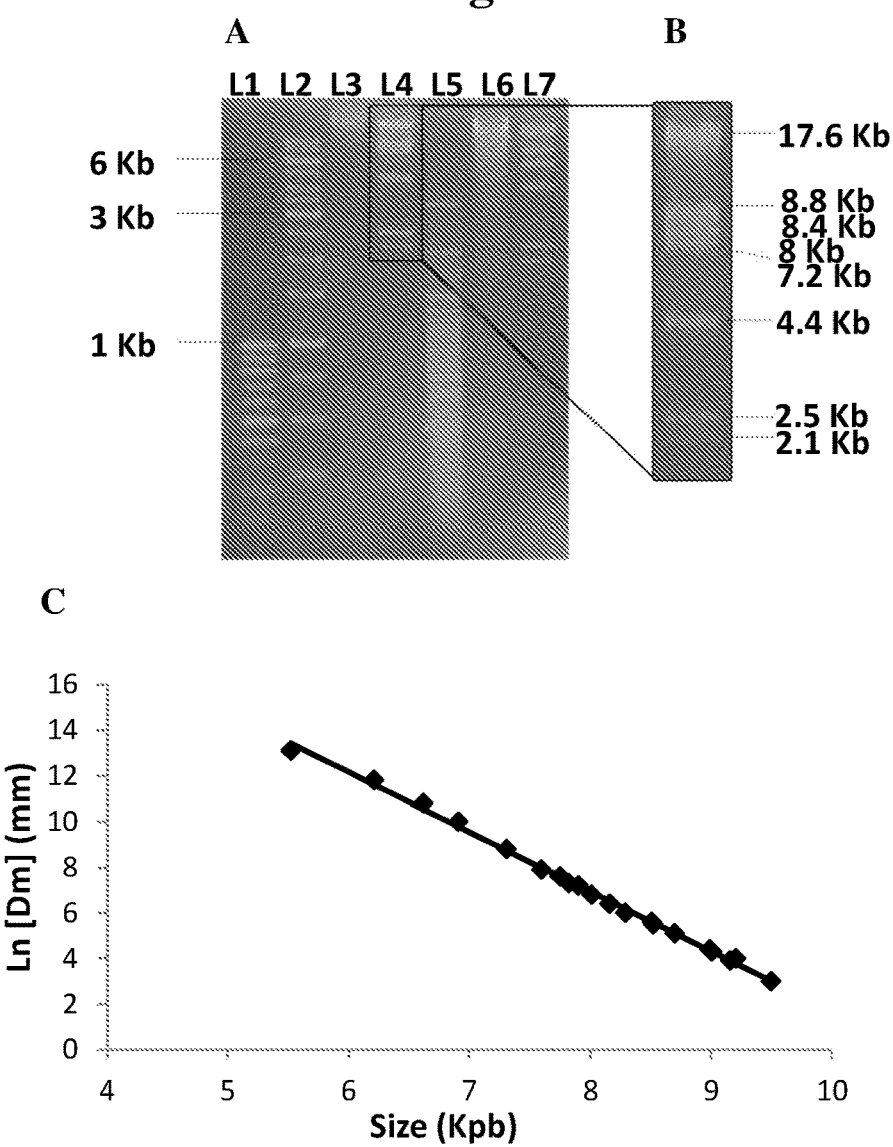
FIG. 5. Restriction test and determination of the molecular mass of the genome from FnpΦ02 by electrophoresis. In a), an electrophoresis gel is presented (agarose 0.8%) as a result of treating genomic DNA from phage FnpΦ02 with restriction enzymes (restriction test), where lanes correspond to L1: Molecular mass standard 100 pb; L2: Molecular mass standard 1 Kpb; L3: non-digested DNA; L4: DNA/HindIII; L5: DNA/Drat L6: DNA/XbaI and L7: lambda DNA/HindIII. In b), magnification of the bands obtained in the digestion of FnpΦ02/HindIII is presented, with the goal of determining the size of the genome. In c), the straight line is presented, as well as the equation of the straight line obtained from the pattern of migration of molecular mass standard 1 Kb and bands obtained from the restriction test.

The phage's genome is processed according to what has been previously described, establishing that the genome of the phage is only sensitive to the action of the enzyme DNasa I; therefore, genetic material is classified as DNA (FIG. 5a). When treating the different endonucleases of type II restriction, the genetic material of the phage is sensitive to cut with enzymes BamHI, PstI, XbaI, KpnI, DraI, HindIII, EcoRI and Sau3AI; therefore, it is classified as genetic material of double-stranded DNA (FIG. 5b). In order to determine the size of the genome, it is digested with enzyme HindIII, where migration of the bands obtained was interpolated with an equation got from the molecular mass standard 1 Kpb ADN ladder (FIG. 5c). The presence of 8 bands shows the existence of at least 7 cut places for the enzyme, which recognizes the sequence A↓AGCTT. With this information, the size of the genome is approximately estimated in 59 Kpb.

The sequence of the phage FnpΦ02 is determined by cutting with enzyme HindIII and the fragments were cloned in vector pSU19. Partial sequencing of a fragment of approximately 500 pb (access number HG014662) and the following bioinformatics analysis show a high identity correspondence (approximately 95%) with phage PA6 *Propionibacterium acnes*, a bacteriophage which is a member of the non-classified genus of the Siphoviridae family (FIG. 6a). No other identity or homology is found with other phage sequence, something that suggests that phage FnpΦ02 is a part of a non-classified group inside the Siphoviridae family. The fragment was analyzed and two small sections were found, which are aligned with ORFs that process a consecutive disposition in the genomic context of the phage PA6 (FIG. 6b). It was found out that both fragments showed an amino acid similarity to proteins from phage PA6. The first section ORF codifies for a small peptide of 54 amino acids that shares a 98% of identity with a segment from protein Gp3, a protein of 441 amino acids that has a putative structural function (FIG. 6c). The second section of ORF codifies for a peptide of 72 amino acids that shares an 84% of identity and 94% of similarity with protein Gp4, a protein of 251 amino acids with a putative function of terminase.

Genetic Characterization Phage FnpΦ11

Figure 7:
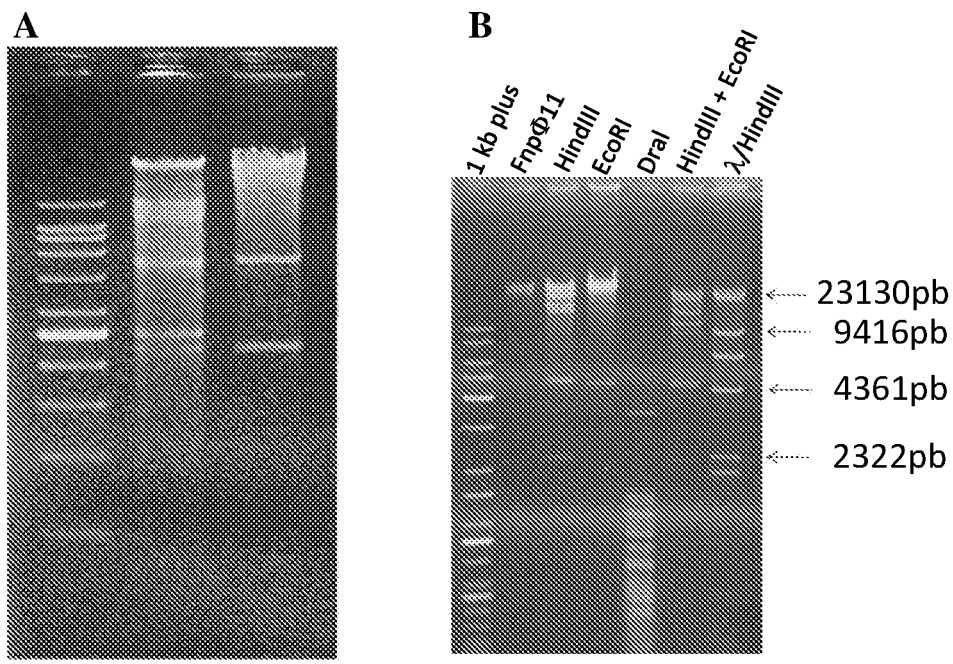
FIG. 7. Restriction test and determination of the molecular mass of the genome from FnpΦ11 by electrophoresis. Restriction test of genetic material. In a) and b), the cutting pattern with different restriction enzymes is observed. b) From the simultaneous cut with enzymes HindIII and EcoRI and subsequent comparison with the molecular mass standard, the size of the genome was calculated.

The phage's genome is purified and treated with enzymes DNasa I or RNasa A. After the incubation, the phage's genome is only sensible to the action of the enzyme DNasa I; therefore, the genetic material is classified as DNA. In order to determine if the genome corresponds to double-stranded DNA, it is treated with different endonucleases of type II restriction. The genome of this phage is not digested by enzymes PstI, XbaI y XhoI (FIG. 7a). On the contrary, genetic material of phage FnpΦ11 is sensitive to the cut with enzymes DraI, HindIII y EcoRI. From the cut with enzymes HindIII y EcoRI, the size of the phage's genome is calculated, which is estimated in 39 Kpb (FIG. 7b).

The complete sequencing of the genome of FnpΦ11 is done by pyrosequencing 454, which showed that the size of the genome is approximately 130 Kpb. This difference, regarding the size obtained with the migration pattern, can be explained by the presence of a band very close to the superior limit of the cut of the equation of the straight-line. FnpΦ11 is determined to have a G+C percentage of 24.93% and presents 178 possible open reading frames (ORF). The analysis of these ORF showed the presence of 31 genes with nucleotide identity, and among them, genes which are related to DNA protection systems stand out, as well as enzymes which are involved in the replication of the phage. In table 2, the main ORF with nucleotide identity of the phage FnpΦ11 are presented, according to bioinformatics analysis.

TABLE 2

Main ORF with nucleotide identity (BLAST) in phage FnpΦ11.

| ORF (BLAST) | Function |
| --- | --- |
| Phage repression protein | Non-essential protein involved in the development of lytic cycle |

TABLE 2-continued

Main ORF with nucleotide identity (BLAST) in phage FnpΦ11.

| ORF (BLAST) | Function |
|---|---|
| Specific adenine methyltransferase<br>DNA Methylase C-5 cytosine-specific<br>DNA Methylase N-4 cytosine-specific<br>and DNA methylase N-6 adenine-specific | Catalyzing the transfer of a methyl group to DNA. They are generally used as a way to protect DNA of the cut with restriction enzymes |
| DNA ligase<br>DNA polymerase I<br>RecD-typo DNA helicase YrrC (Helicase) | Enzymes involved in the replication of genetic material |
| dUTP pyrophosphatase | It is an enzyme that catalyzes the reaction: dUTP + H2O → dUMP + pyrophosphate |
| Ribonucleotide reductase, type III | Enzyme that catalyzes the reduction of ribonucleotides in the corresponding 2'-deoxyribonucleotides and play a crucial role in the synthesis of DNA |
| ATPase linker of AND of phage (terminase) | Protein involved in the translocation of DNA to the viral capsid |
| 7 tARN's | RNA involved in the transport of amino acids to the ribosomes |
| Linker protein of DNA Hbsu | DNA binding protein found both in bacteria and dsVirus |

Due to the fact that with most of the ORF nucleotide identity result was not obtained, the presence of possible domains at a protein level is sought, in order to find a possible function for said ORF. This analysis identified genes that were related to the synthesis of the structural components of the phage (capsid and tail) and the possibly involved genes with lysis of the bacteria (holine-endolysine system, Table 3). A total of 144 ORF do not present nucleotide identity nor functional domains; therefore, they encode for hypothetical proteins.

TABLE 3

Main domains found in ORF without nucleotide identity by BLAST in FnpΦ11.

| †Hypothetical Protein | Function |
|---|---|
| Protein related to the tail of the phage | Involved in the assembly of the initiating complex for polymerization of the tail |
| Predicted nucleotidyltransferase | They transfer a monophosphate nucleotide |
| N-acetilmuramoil-L-alanine amidase | It cuts the peptidoglycan between N-Acetylmuramic and residues of L-amino acids (possible endolysine) |
| Superfamily PD-(D/E)XK nuclease | Resolvase |
| Holin family of phage (Lysis S proteins) | Formation of a pore in the membrane |
| ARN ligase | Ligase. It has ssARN and ssADN as substrates |
| Internal head protein of the phage phiKZ | Proteins involved in the synthesis of the capsid |
| Capsid putative protein V20 | |

†The function was assigned according to the presence of possible domains conserved in the protein. Said domains were sought with programs Pfam and KEEG.

Genetic Characterization of the Phage FnnΦ107

Figure 8:
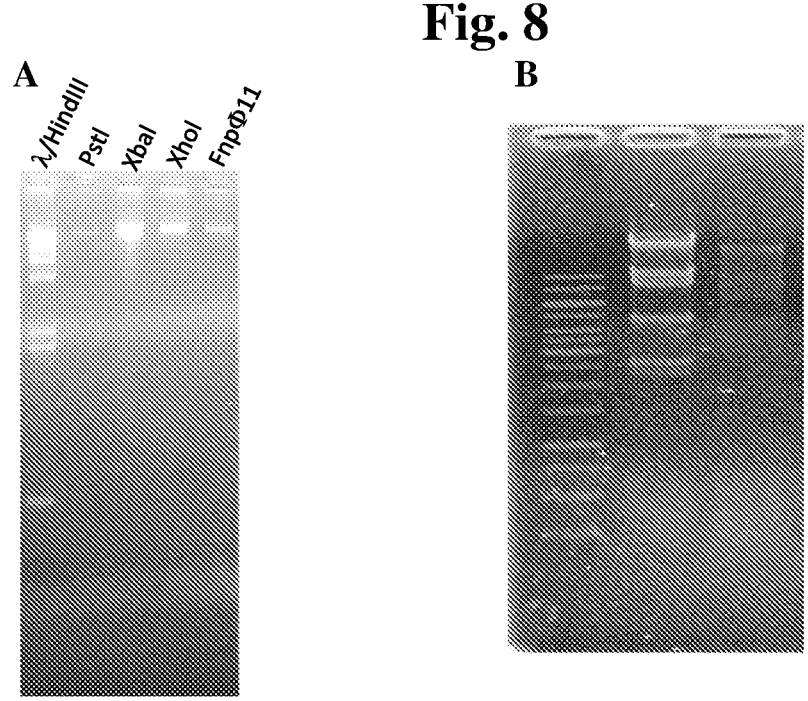
FIG. 8. Comparative restriction test of genome from FnpΦ02, FnpΦ11 and FnnΦ107 in 0.8% agarose gel electrophoresis. a) Digestion pattern of phages FnpΦ02 and FnpΦ11. L1, Molecular mass standard 1 Kpb; L2, FnpΦ02/HindIII; L3, FnpΦ11/HindIII. B) Digestion pattern of phages FnpΦ02 and FnpΦ107. L1, Molecular mass standard 1 Kpb; L2, FnpΦ02/HindIII; L3, FnpΦ107/HindIII.

The phage's genome is purified and treated with enzymes DNasa I or RNasa A. After the incubation, the phage's genome is only sensible to the action of the enzyme DNasa I; therefore, the genetic material is classified as DNA. In order to determine if the genome corresponds to double-stranded DNA, it is treated with different endonucleases of type II restriction, such as HindIII. This enzyme allows to interpolate the size of the bands obtained in front of the equation of the straight-line obtained by the molecular mass standard 1 Kpb DNA. In this way, the size of the genome is estimated to be approximately 42 Kpb (Table 4). In this way, it is possible to claim that this bacteriophage corresponds to a different phage of the ones analyzed previously (FnpΦ02-FnpΦ11), as a different digestion pattern in front of the same restriction enzyme was observed (FIGS. 8 a and b).

In table 4, the determined sizes for the genome of the isolated bacteriophages FnpΦ02, FnpΦ11 and FnnΦ107 are presented.

TABLE 4

Summary of the genome sizes of Fnpφ02, Fnpφ11 and Fnnφ107.

| | Fnpφ02 | Fnpφ11 | Fnpφ107 |
|---|---|---|---|
| Genome size | 59 Kpb | 130 Kpb | 42 Kpb |

Example 4: Growth Characterization of FnpΦ02 and FnpΦ11

In this example, the growth ability of the phages FnpΦ02 and FnpΦ11 is evaluated. In order to do this, adsorption tests are performed, which allows us to determine affinity between the phage and the bacteria, according to their ability of recognizing receptors of the target bacteria.

The adsorption test is performed according to the protocol described by Sillankorva and coll. (Genetics. Vol. 180(1), pages 471-482, 2008), with some modifications. A bacteria culture in early exponential phase ($OD_{600}$ 0.15-0.2) is infected with a suspension of phages in a relation of 1:100 (MOI de 0.01). The mixture is incubated at room temperature, and every 1 minute, a 100 μL sample is taken. The samples are treated with chloroform, centrifuged at 10,000×g for 3 min., and then diluted and plated on a soft agar lawn of the sensitive bacteria. After the incubation, a count of UFP/mL is performed.

The adsorption rate is calculated with the formula established by Barry and Goebel (1951)

$$k = (2.303 \log P_0/P)/t(B)$$

Where $P_0$=initial phages concentration; P=final phages concentration; t=time; B=bacteria concentration.

In the analysis of the infection phases of FnpΦ02, a quite fast phage-bacteria interaction was observed in the first stage, with an 87% of adsorption of the phage in 3 min. (FIG. 9a). The adsorption seems to happen in only one stage, while the viral particle quantity remains constant for 5 min. The adsorption rate represents the level of affinity between the phage and the bacteria, and it was determined, according to Barry and Goebel (1951), for a period of 3 minutes, resulting in a constant of adsorption of $7.5*10^{-10}$ mL min$^{-1}$.

In order to identify the different stages of the infection process of FnpΦ02, the test that was performed was the one called One Step Growth (OSG), which is a phage growth measure test in order to compare the total number of phages and the number of free phages. This test is performed according to the protocol described by Sillankorva and coll. (2008), with some modifications. In order to determine the latency period, eclipse period, peak period and burst size, where burst size corresponds to the average number of phages produced by a bacteria infected by a population of this phage.

A bacteria culture in early exponential phase was infected (OD$_{600}$ 0.15-0.2) with phage suspension in a relation of 1:100 (MOI of 0.01). This mixture is incubated for 5 minutes at room temperature in order to allow the pre-adsorption of the phage. Afterwards, every 1 hour of the incubation, two samples are taken. The first ones are immediately platen on a lawn of the sensible bacteria, while the second ones are previously treated with chloroform at 1% (vol/vol) in order to allow the release of the phages that are still in intracellular. The UFP/mL is determined by serial dilutions.

The burst size (b) was calculated as it follows:

b=Final phages concentration

Bacteria Concentration

The test showed that the latency time and eclipse period of FnpΦ02 R is 15 hours and 7 hours, respectively. The burst size is 100 phages per infected bacteria, measured for a 10 hours period of exponential propagation at 37° C. (FIG. 9b).

When performing this analysis on phage FnpΦ11, a quick phage-bacteria interaction is observed, since 1 min. after incubation, the percentage of free phages diminished in a 95.4%. After this time, fewer and fewer phages are found in the supernatant, even getting to be a 0.3% after 3 min. post-incubation (FIG. 10a). The adsorption rate for the period comprised between 0 to 1 min. was $3.1 \times 10^{-7}$ mL min$^{-1}$. In relation to the analysis of OSG, it was established that the latency period and the peak period were 6 hours and 16 hours, respectively. The eclipse period was indistinguishable from the latency period, showing that the lysis time is very brief. FnpΦ11 achieved a burst size of about 10 UFP per infected cell at 37° C. (FIG. 10B).

In table number 5, there is a summary of the information about the characterization of the growth of phages FnpΦ02 and FnpΦ11, according to adsorption tests and One Step Growth previously described.

TABLE 5

Comparison of information of the growth of phages FnpφO2 and Fnpφ11

| Parameter | FnpφO2 | Fnpφ11 |
|---|---|---|
| Adsorption rate | | |
| BHI | $5.6 \times 10^{-7}$ mL min$^{-1}$ | $3.1 \times 10^{-7}$ mL min$^{-1}$ |
| OSG | | |
| Latency period (L) | 4.5 h | 6 h |
| Peak period | 5 h | 16 h |

TABLE 5-continued

Comparison of information of the growth of phages FnpφO2 and Fnpφ11

| Parameter | FnpφO2 | Fnpφ11 |
|---|---|---|
| Eclipse period (e) | | 6 h |
| Burst size (b) | 400 UFP per cell | 10 UFP per cell |

Example 5: Determining the Infection Curve of the Phages FnpΦ02 y FnpΦ11

In this example, the infection curve of the isolated bacteriophages FnpΦ02 y FnpΦ11 is presented, in order to distinguish lytic phages and temperate phages.

Methodology consists in preparing initially a culture that was incubated all night to a dilution 1:200 of F. nucleatum. Afterwards, the bacteria growth is measured by spectrophotometry at optical density of 600 nm (DO$_{600}$) every 1 hour per 48 hours, approximately. When the culture is found in the early exponential phase (OD$_{600}$ 0.15-0.2), it is infected with the phages in a multiplicity of infection (MOI) of 0.01 (CFU:PFU).

The results show that the growth curve of F. nucleatum presents a lag phase that lasts for about 25 hours, approximately, an exponential phase that lasts for about 20 hours and a stationary phase that reaches a DO$_{600nm}$ of around 0.7. The infection with FnpΦ02 in early exponential phase of the culture (DO$_{600}$ 0.1-0.2) causes an interruption in this growth phase. At this point, bacteria lysis is higher than the generation rate; therefore, we can start to observe a continuous drop in the optical density until it reaches a DO$_{600nm}$ close to 0.2 (FIG. 11a).

The reached maximum lysis is when infecting with MOI 2, which corresponds to a DO$_{600nm}$ of approximately 0.1. The lytic effect is observed up to a MOI 0.1, being this one the minimum MOI for observing the lysis of the culture in these test conditions. The lowest used MOI (0.01 and 0.001) shows similar curves to the negative control of the test (culture without bacteriophage or with inactivated phage) (FIG. 11b).

Regarding the determination test of the infection curve of the phage FnpΦ11, the growth curve of R. nucleatum presents a lag phase that lasts for approximately 15 hours, an exponential phase that lasts around 15 hours and culminates in a stationary phase with a DO$_{600nm}$ of 0.8.

Figure 12:
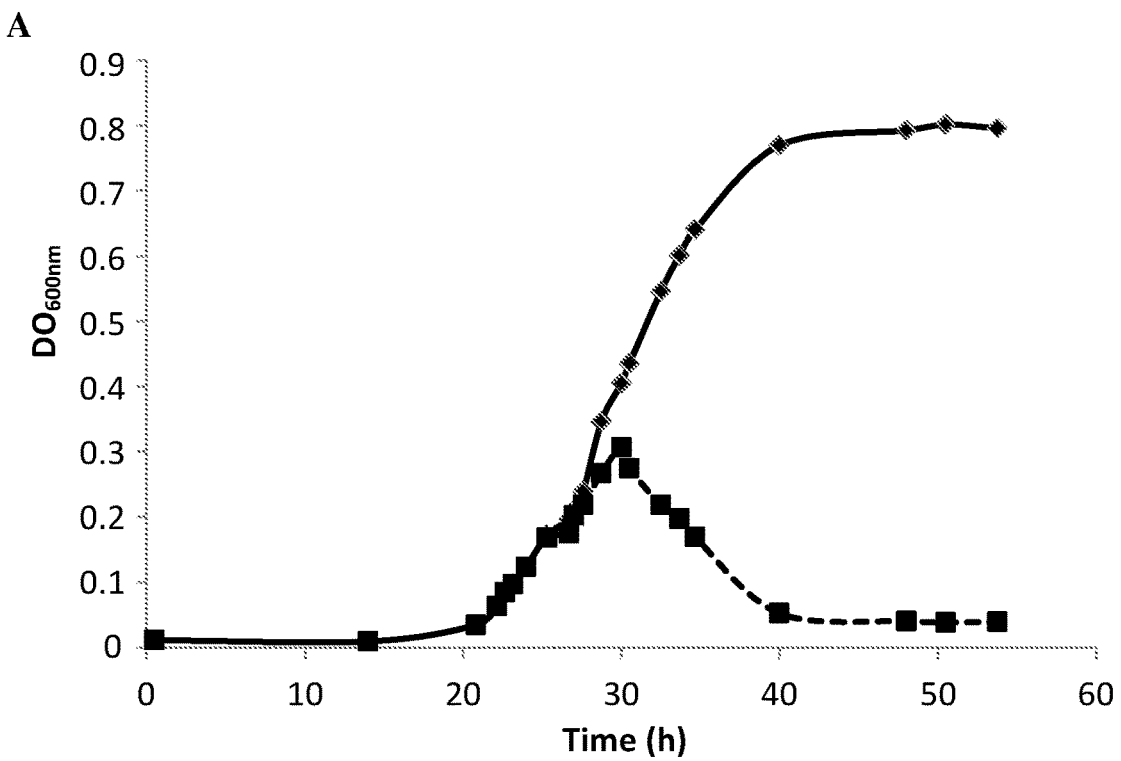
FIG. 12. Infection curve FnpΦ11. a) Growth curve of Fusobacterium nucleatum (D.O v/s time), where  corresponds to the curve resulting of the growth of a inoculum of Fusobacterium nucleatum, and  corresponds to the growth curve of Fusobacterium nucleatum in presence of phage FnpΦ11. The arrow indicates the moment of the infection with phage (MOI 1:1000). b) Image of the observation of bacteria culture at the end of the growth curve.

The infection with FnpΦ11 in early exponential phase of the culture (DO$_{600nm}$ 0.1-0.2) causes an interruption of exponential phase in DO$_{600nm}$. At this point, bacteria lysis is higher than the generation rate; therefore, we can observe a continuous drop in the optical density until it reaches a DO$_{600nm}$ which is less than 0.05 (FIG. 12a), observable in a very low final turbidity in the lysate (FIG. 12b). When performing the count of CFU, once the growth curves were finished, colonies were not obtained, showing that the phage able to lysate completely the bacteria culture. These features, added to the fact that a lawn of the sensible bacteria forms clean lysis plaques, suggests that FnpΦ11 has features of a lytic phage.

In table 6, the main features of the isolated phages for F. nucleatum are presented.

TABLE 6

Summary of the characterization of phages Fnpφ02, Fnpφ11 and Fnnφ107.

| Characterization | Fnpφ02 | Fnpφ11 | Fnnφ107 |
|---|---|---|---|
| Macroscopic | Turbid lysis plaques Diameter 0.5-1 mm | Clean lysis plaques Diameter 0.5-1 mm | Clean lysis plaques Diameter 1-1.5 mm |
| Microscopic | Icosahedral capsid 50 nm. Filamentous tail 150 nm | Icosahedral capsid 77 nm. Filamentous tail 55 nm | Icosahedral capsid 90 nm. Filamentous tail 346 nm |
| Host Range | *F. nucleatum* | *F. nucleatum* | *F. nuc.* subs. *Nucleatum* |
| Genetic material | Double-stranded DNA of 59 Kpb | Double-stranded DNA of 130 Kpb | Double-stranded DNA of 142 Kpb |
| Order | Caudovirales | Caudovirales | Caudovirales |
| Family | Siphoviridae | Podoviridae | Siphoviridae |
| Genus | Not subclassified yet | Not subclassified yet | Not subclassified yet |

Example 6: Procedure of Transformation of Lysogenic Bacteriophage FnpΦ02 to Lytic Bacteriophage FnpΦ02-14 and Determination of the Growth Curve Previous tests of determination of infection curve established that the bacteriophage FnpΦ02 corresponds to a temperate phage with low or nonexistent lytic ability (described in example 5), which means that the bacteriophage is unable to infect, lysate or eliminate the bacteria efficiently. With the aim of increasing its ability of infection and spreading, thus assuring the elimination of the pathogen, the process of transforming the lysogenic bacteriophage FnpΦ02 into a lytic bacteriophage started.

Figure 13:
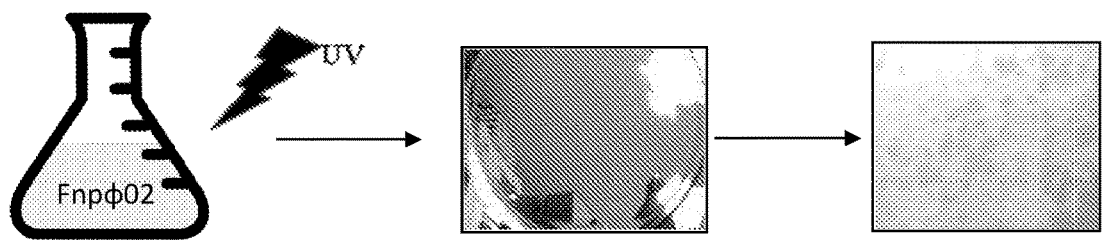
FIG. 13. Methodological diagram for recovering lytic phages FnpΦ02-14. A culture of lysogenic phages FnpΦ02 was exposed to UV light, plagued and recovered from corresponding lytic plaques.

In order to obtain mutant viral particles, random mutations are performed by exposing them to UV light (260 nm). Like this, new viral particles coming from phage FnpΦ02 are obtained, and they are selected by their ability of creating clean lysis plaques. Clean lysis plaques are isolated and spread. This new particles were tested in a growth curve of *F. nucleatum*. The mutant viral particle named FnpΦ02-14 is selected, because it has a better efficiency in the infection of the bacteria (FIG. 13).

After selecting the mutant viral particle FnpΦ02-14 an evaluation is performed, comparing the ability of lysating *F. nucleatum* by infecting the bacteria with FnpΦ02 and FnpΦ02-14 concurrently. When infecting both phages, the logarithmic phase of the curve stops and a reduction of the optical density is observed. When adding phage FnpΦ02-14, a better bacteria lysis efficiency is observed, being this one faster in reaching a final DO600 nm of less than 0.1, (FIGS. 14 *a* and *b*).

Example 7: In Vivo Evaluation of the Effectivity of Lytic Bacteriophages Versus Current Treatment (Local Cleaning and Antibiotics) on the Microbiologic Count Associated with Periodontal Destruction In this example, the effectiveness of the produced lytic bacteriophages regarding current treatments for treating periodontal disease (local cleaning and antibiotics) is established.

An evaluation is performed to determine the effect of these treatments on the microbiological count associated with periodontal destruction in Sprague Dawley rat models inoculated with *P. gingivalis* and *F. nucleatum*, the main pathogens of the etiology of periodontal disease.

Methodology consists in co-infecting rats with *P. gingivalis* and *F. nucleatum*, and treating or not treating them with the mixture of bacteriophages FnpΦ02-14, FnpΦ11 and FnnΦ107 at different MOI. The procedure for each stage is described below:

Coinfection

For coinfection, the protocol proposed by Kesavalu and coll. (J Clin Periodontol., Vol. 36(5, pages 406-410, 2009) is taken into account, where the subjects are separated in groups of 3 rats per cage for a week for adaptation period. Afterwards, an initial treatment is performed, based in administrating kanamycin 20 mg (Kan 20 mg) and ampicillin 20 mg (Amp 20 mg) for 4 days, to finally, in day 5, perform a local cleaning with Chlorhexidine at 0.12% (CHX 0.12%). In the Negative control group: the initial treatment is performed on week 0, and on week 10, the sacrifice of the rats is performed. In the Positive control group: the initial treatment is performed on week 0, and afterwards, on weeks 2, 4, 6 and 8, the inoculation of the bacteria mixture is done for 4 following days every week. Finally, on week 10, the sacrifice of the rats of the group is performed. The initial treatment of local cleaning with CHX 0.12% and the local administration of the bacteria mixture is performed under anesthesia for 5-10 sec. with isoflurane gas. The sacrifice of the rats was performed with an anesthesia overdose of Ketamine:Xylazine (2:1).

Composition of the Bacteriophages Mixture

The mixture of the three lytic bacteriophages FnpΦ02-14, FnpΦ11 and FnnΦ107, specific for *E nucleatum*, is performed, with a concentration of $10^8$, $10^{10}$ and $10^8$ UFP/mL, respectively. Afterwards, it was kept at 4° C. until it was used.

Treatment

Each research group is composed by 3 subjects per cage, and there ware a number of 6 subjects per group. The research groups are the following: Group 1 (Continuous treatment phage), in which the administration of the mixture of bacteriophages in a multiplicity of infection (MOI) of 0.01 (1 bacteria for 100 phages) is performed, in the same inoculation times as the bacteria mixture (week 2, 4, 6 and 8), for 4 days every time. Group 2 (Phage MOI 0.1), in which the administration of the blending of bacteriophages in a MOI of 0.1 is performed on weeks 6 and 8, for 4 following days every time. Group 3 (Phage MOI 1), in which the administration of the blending of bacteriophages in a MOI of 1 is performed on weeks 6 and 7, for 4 following days every time. Group 4 (local cleaning), which receives the treatment of local cleaning with a cotton swab with chlorhexidine 0.12% in weeks 6 and 8, for 4 following days every time. Group 5 (Antibiotics), which receives a treatment with amoxicillin added in water in weeks 6 and 7, in following days. Group 6 (Local cleaning-antibiotics), which receives a treatment with external tanning in the treatment with amoxicillin, doing the same periods and forms of administration previously described for Groups 4 and 5. Every administration of local treatment is performed after anesthetizing the rats with isoflurane gas for 5-10 sec.

Every rat used in this research was sacrificed with an overdose of Ketamine:Xylazine (2:1).

In order to evaluate the microbiological factor associated with periodontal destruction, two strategies are used: the first one is the quantification of de *P. gingivalis* and *F. nucleatum*, and the second strategy is the detection of *P. gingivalis* and *F. nucleatum* by PCR technique.

Determination by Bacteria Count

Bacteria count of *F. nucleatum* (Fn) is performed in a selective culture medium, called CVE. The *F. nucleatum* count performed in the research groups with different treatments shows a tendency to reducing bacteria count in the samples after the treatment with preventive phage, phage MOI 1, phage MOI 0.1, chlorhexidine 0.12% and chlorhexidine+antibiotics (sample 3 and post mortem sample), but this tendency does not get to be significant (FIGS. 15 *a, b, c, d* and *f*). In the group with antibiotics, this tendency is not seen, and only the count in the post mortem sample decreases (FIG. 15*e*).

The count of *P. gingivalis* is performed in a non-direct way by sowing in an enriched medium of blood with Hemin-menadione, which allows to observe the bacteria that are pigmented with black, from which *P. gingivalis* is the most important representative. The count of *P. gingivalis* in the different research groups shows a low recovery of these bacteria (less than 1000 bacteria) in the cases where it was obtained. In each research group that has been analyzed, there is no significant difference between the samples taken before and after the corresponding treatment (FIGS. 16 *a, b, c, d, e* and *f*). When considering the tendency in the analysis, is observed that in the groups Preventive phage, MOI 1 and MOI 0, they show a lower count of these bacteria pigmented with black after the treatment (sample 3 and post mortem sample) (FIGS. 16 *a, b* and *c*).

Additionally, the count of total anaerobic bacteria is done, a test that indicates that none of the research groups that have been analyzed present any significant decrease regarding the corresponding treatment for every case, showing concentrations of bacteria in balance throughout the coinfection test and treatment evaluation (FIGS. 17 *a, b, c, d, e* and *f*).

Bacterial Determination of E *Nucleatum* and *P. gingivalis* by PCR.

In order to determine *F. nucleatum* and *P. gingivalis* by PCR, the protocol mentioned in table 8 was used, in which volumes of each reactive presented in order to make the mixture of PCR. Specific primers used are presented in table 9. The program used for determining the species is: initial denaturation for 5 minutes at 94° C., 35 cycles of 94° C. for 30 sec., 55° C. for 30 sec. and 72° C. for 30 sec., and the final extension at 72° C. for 10 min. The PCR product was solved in an agarose gel at 1.5% in buffer TAE 1×.

TABLE 8

Protocol used for reaction of PCR in the detection of *Porphyromonas gingivalis* and *Fusobacterium nucleatum*.

| Reactive | Volume |
| --- | --- |
| Buffer of PCR 10X | 2.0 μL |
| MgCl$_2$ 25 mM | 1.2 μL |
| dNTP's 10 mM | 0.4 μL |
| Primer 1 (25 mM) | 0.2 μL |
| Primer 2 (25 mM) | 0.2 μL |
| Template | 1.0 μL |
| H$_2$Od | 14.9 μL |
| DNA polymerase Taq (5 U/μL) | 0.1 μL |

TABLE 9

Primers used in the detection of *Porphyromonas gingivalis* and *Fusobacterium nucleatum*.

| Name | Target | Sequence (5'-3') | Size (pb) |
| --- | --- | --- | --- |
| Pgin-1 | 16S rDNA | TGTAGATGACTGAAAACC | 197 |
| Pgin-2 | *Porphyromonas gingivalis* | ACGTCATCCCCACCTTCCTC | |
| Fspp-1 | 16S rDNA | GGATTTATTGGGCGTAAAGC | 167 |
| Fspp-2 | *Fusobacterium nucleatum* | GGCATTCCTACAAATATCTACGAA | |

In the detection of E *nucleatum* by PCR, when comparing previous samples to the corresponding treatment in each research group and the samples taken after the treatment, it is observed that in the samples of the group with phage MOI 1, group chlorhexidine, group antibiotics and group Chlorhexidine plus Antibiotics, a lower count of positive detections for *F. nucleatum* was obtained in the post-treatment samples when comparing them to the pre-treatment samples. On the contrary, samples from the group with preventive phage and MOI 0.1 allow the detection of the bacteria after the treatment with the phage (FIG. 18).

Detection of *P. gingivalis* does not present any difference in identification of the bacteria between controls.

Example 8: In Vivo Evaluation of Effectiveness of Lytic Bacteriophages Versus Current Treatment (Local Cleaning and Antibiotics) on the Periodontal Integrity Parameters The results of the evaluation of periodontal integrity parameters in rats treated with the same methodology described in example 7 are presented in this example.

Periodontal integrity is determined according to the observation of clinical signs in a periodontal tissue level associated with the first molar. The parameters considered in the evaluation are: adhesion level, periodontal pocket depth (mm), observation of alveolar crest and gum/tooth index.

Evaluation of Parameters of Periodontal Integrity:

Table 10 presents the information associated with the measure of periodontal destruction signs of the research groups with treatment with preventive phage, phage MOI 0.1 and phage MOI 1. In the case of preventive phage, we obtained subjects that presented certain features associated with positive control (no. 1, Table 10) with a lower adhesion level, a high periodontal pocket depth (1 mm) and a relatively low index gum/tooth, even though it does not present exposition of alveolar crest. Other subjects inside the group (no. 2 and no. 3) present parameters closer to the range of negative control in adhesion level and gum/tooth index, even though the depth of the periodontal pocket is still high. In the group with phage MOI 0.1, there are some subjects that do not present any sign of tissue destruction (no. 1 and no. 2), while others present non conclusive signs (no. 3) regarding adhesion and gum/tooth index. Finally, in the group of the phage MOI 1, the analyzed subjects do not present any signs of destruction regarding loss of adhesion, and do not present alveolar crest exposure, while subjects no. 1 and no. 2 show a high depth of periodontal pocket (1 mm-1.2 mm) and a gum/tooth index of (0.33-0.5) and subject no. 3 did not present a determining periodontal pocket and presented a gum/tooth index inside the range of negative control.

TABLE 10

Representative data of periodontal parameters in the groups with treatment for preventing phage (phage MOI 0.1 and phage MOI 1).

| | Control | Control | Preventive phage | | | Phage MOI 0.1 | | | Phage MOI 1 | | |
|---|---|---|---|---|---|---|---|---|---|---|---|
| | (−) | (+) | no 1 | no 2 | no 3 | no 1 | no 2 | no 3 | no 1 | no 2 | no 3 |
| Adhesion Level | ++ | − | + | ++ | ++ | +++ | ++ | + | ++ | ++ | ++ |
| Periodontal pocket depth(mm) | 0.7-08 | 0.7-1 | 1 | 0.8 | 0.9 | 0.5 | 0.6 | 0.8 | 1 | 1.2 | 0.8 |
| Obs. Alveolar crest | No | Yes | No | No | No | No | No | No | No | No | No |
| Gum/tooth index (2/1) | 0.5-0.8 | 0.1-0.43 | 0.5 | 0.6 | 0.5 | 0.5 | 0.6 | 0.4 | 0.33 | 0.5 | 0.66 |

(+++), high.
(**), average.
(+), low.
(−) absent.

Example 9: In Vivo Evaluation of Effectiveness of Lytic Bacteriophages Versus Current Treatment (Local Cleaning and Antibiotics) on the Inflammatory Response In order to evaluate a possible inflammatory response of the research groups, after performing the different treatments, the post mortem extraction of the left side of the inferior jaw hemi sectioned is performed in the research subjects.

In order to perform the analysis of gingival tissue associated with the first molar once the piece is worn out, this one is fixed in a solution of paraformaldehyde at 10% for 24 hours. Afterwards, the bone is decalcified in an nitrous oxide solution for 24 hours. The decalcified tissue was soaked in paraffin blocks, in order to be cut afterwards by a microtome in transversal sections for 4μ, in order to be finally stained with the hematoxylin-eosin staining. Cuts were observed with different magnifications (40×-100×-400×) and images were taken with the program Mshot Digital Imaging System. The presence or absence of inflammation in the tissue was examined by using the following parameters: Hematopoietic distribution, presence of vasodilation, thickness of keratinized epithelial tissue, presence of immune cells (lymphocytes, monocytes, polymorph nuclear, etc.), prisoners of inflammatory focus and cell infiltration in keratinized epithelium. In this way, the manifestations of acute or chronic inflammatory response and the normal, incipient, or established inflammatory response were determined.

In this way, it was observed in the cuts of the research group with preventive phage a normal cell distribution with homogeneous density of fibroblasts in gingival tissue and keratinized tissue of increased thickness but normal consistency, something that suggests that a previous inflammatory process existed (FIG. 19a). A low cell migration was observed, low concentration of immune cells and low basal vasodilation of the capillaries in gingival tissue (FIG. 19b). This indicates that an active inflammatory response was not found in the tissue.

In the analysis of histological sections obtained from the research group with phage MOI 0.1, a normal cell distribution (without the presence of cell focus), both in keratinized and gingival tissue was observed (FIG. 20a). Specifically, keratinized tissue had normal thickness, with less infiltration of immune cells (lymphocytes). In gingival tissue, the basal presence of lymphocytes and normal vasodilation was observed (FIG. 20b). These results indicated the absence of inflammatory response.

In the analysis of the research group with chlorhexidine 0.12% treatment, clear inflammatory focuses were observed, aiming towards the keratinized epithelium, distinguishing an infiltration of immune cells coming from gingival tissue. Even more, this epithelium presents an important thickness (FIG. 21a). In gingival tissue, a considerable amount of immune cells was observed, as well heterogeneous cell distribution, aiming towards the free end of the gum (FIGS. 21 b and c). As a result, we can distinguish the presence of an active acute inflammatory response.

In the analysis of the histological sections of the research group treated with amoxicillin, it was observed that the keratinized tissue presented increased thickness with limited cell infiltration, with a considerable amount of lymphocytes and plasmocytes and a lower quantity of neutrophils (FIG. 22a). In the gingival tissue, the presence of nascent inflammatory focuses was shown, with an initial cell distribution towards the free keratinized epithelium (FIG. 22b). Therefore, the presence of an acute incipient inflammatory response was indicated, as well as a possible previous inflammatory response.

In the histological sections analyzed from the research group treated with chlorhexidine and amoxicillin, a keratinized tissue with increased thickness with cell infiltration from the gingival tissue was observed (FIGS. 23 a and b). The gingival tissue presented small focuses of immune cells with an initial distribution towards the free keratinized epithelium, as well as an increase of vascularization and clear vasodilation (FIGS. 23 b and c). This signs indicate the presence of an acute incipient inflammatory response, preceded by a possible previous chronic response.

Example 10: In Vivo Evaluation of Effectiveness of Lytic Bacteriophages Versus Current Treatment (Local Cleaning and Antibiotics) about Reabsorption and Bone Loss This example presents methodology and results of the evaluation of effectiveness of isolated lytic bacteriophages regarding treatment with local cleaning and antibiotics about reabsorption and bone loss.

Bone Reabsorption

The determination of bone reabsorption of the different subjects of treatment is performed based on measuring the molecules associated with this type of physiological response. The levels of RANKL and OPG molecules are measured by Enzyme-Linked ImmunoSorbent Assay (ELISA), specifically the ELISA indirect type, performed from a plasma sample. The blood sample was extracted as follows: the rat is deeply anesthetized with ketamine:xylazine, via the intraperitoneal route. The rat is treated with heparin 2 minutes before surgery, also via the intraperitoneal route with 200-300 µL. Abdomen and thorax are sprayed with 70% ethanol, in order to perform an incision in the skin, cutting the musculature and separating the abdominal organs, in order to have better access to vena cava. Once the vena cava is located, approximately 5 mL of blood are extracted in a $K_2$ EDTA (BD Vacutainer) tube. The tube is centrifuged at 6000 g for 20 minutes (nonstop) and the plasma obtained in the separation stage is reheated and kept at −20° C. until it is used.

Prior to the use of plasma, a quantification of proteins (mg/mL) of each sample is performed by the concentrated Bradford protocol (5×). The analysis is performed in a multiwell plate with 96 flat-bottom wells (Cellstar® Greiner Bio One, Germany), where every well is constituted by 20 µL of sample, 140 µL of distilled water, 40 µL of Bradford 5× (0.5 mg/mL Coomassie blue G-250, 25% de absolute methanol, 42.5% $H_3PO_4$), with a final volume of 200 µL. Plate is shaked and incubated for 5 to 15 minutes at RT. Finally, the absorbance is measured at 595 nm in a plate reader (SQ-2800 model spectrophotometer, United Products & Instruments Inc., Dayton, USA). This way, dilution range of the plasma sample needed for the indirect ELISA analysis is obtained.

The ELISA indirect protocol that has been used for measuring RANKL and OPG is described in the manufacturer's instructions (Santa Cruz Biotechnology, USA) of the antibodies anti-RANKL and anti-OPG, with the following specifications: the sample (antigen) is diluted in a final concentration of approximately 20 µg/mL in phosphate buffered saline (PBS) (137 mM NaCl, 2.7 mM KCl, 8 mM $Na_2HPO_4$, 1.46 mM $KH_2PO_4$, pH 7.4). The wells of a multiwell plate with 96 wells (Elisa plate) are covered with the antigen adding 50 µL to each well (tripled). The plate is covered with adhesive plastic and incubated for 2 hours at room temperature or at 4° C. overnight. Afterwards, the antigen solution is stirred and the plate is washed 3 times with 200 µL of PBS per well. Afterwards, the remaining protein binding sites are blocked by adding 200 µL of 5% fat-free powder milk. The plate is covered with adhesive plastic and incubated for at least 2 hours at room temperature. Afterwards, the plate is washed twice with PBS in every well. After this period, 100 µL of the diluted primary antibody (1:300) are added to each well. The plate is covered with adhesive plastic and incubated for 2 hours at room temperature. Finally, plates are washed 4 times with 200 µL of PBS. 100 µL of the secondary conjugate antibody (anti-Ig rabbits) are added, diluted in a blocking solution (1:5000), immediately right before using. The plate is covered with adhesive plastic and incubated for 1-2 h. at room temperature. Afterwards, the plate is washed 4 times with PBS.

For reaction revealing, the alkaline phosphatase method is performed, because the secondary antibody used for both detections (RANKL and OPG) is conjugated with this enzyme The used substrate is pNPP (p-Nitrophenyl-phosphate) in a concentration of 1 mg/mL, prepared by adding 10 mg of pNPP in 10 mL of glycine buffer (glycine 0.1M, $MgCl_2$ 1 mM, $ZnCl$ 1 mM, pH 10.4). It is mixed and protected from the light. Dissolution of the substratum can be used up to 10 hours after performing the mixture. The substratum is used as it follows: 100 of the solution of the substratum are distributed in each well, it is incubated for 15 to 30 minutes at room temperature. Afterwards, in order to stop the reaction, 100 µL of NaOH 3N, in order to finally read the absorbency of each well at 405 nm in an ELISA reader.

In order to obtain the values of concentration for each sample, the Lambert-Beer formula was used:

$Abs405=\varepsilon*d*[mM]$;

where £: extinction coefficient $18.5*10^3$ $M^{-1}$ $cm^{-1}$ and d: length of the well 1 cm.

$[mM_{diluted}]=Abs_{405}/(18.5*1)$ and $[mM]=mM_{diluted}*$Dilution factor.

From the ELISA methodology to measure bone reabsorption indicators RANKL and OPG, it was determined that in the research groups with analyzed treatments, significant differences did not exist between each of them (FIGS. 24 a and b).

When analyzing the ratio RANKL/OPG, the results show that the groups with treatment with phages, preventive, MOI 1 and MOI 0.1, together with the group with amoxicillin treatment, present significant differences with the ratio obtained from the control group without treatment. The research groups with treatments with chlorhexidine and chlorhexidine plus amoxicillin do not present significant differences regarding the control group without treatment, which means they present higher bone reabsorption than the rest of the analyzed groups (FIG. 24c).

Bone Loss

In order to determine bone loss, we measured directly the alveolar bone of the first molar in the hemi sectioned right jaw of each subject. In order to obtain the alveolar bone, the jaw extraction is performed and autoclaved for 20 min. The first cleaning is performed, removing the associated tissue. Afterwards, the bones are soaked in hydrogen peroxide at 3% for all night at room temperature. After this time, the pieces were washed with distilled water in order to eliminate any remainder of adhered tissue; the bone is brushed with toothpaste and finally washed with distilled water. Clean jaws are stained with methylene blue at 1% for 15 seconds, and then washed with distilled water to remove the excess of stain. The pieces are left to dry by air, and it is in this moment when the limit cement-enamel appears in the associated dental piece. The measure is obtained by measuring from the exposed base of the root of the tooth to the cement-enamel limit.

The quantifying of bone loss is determined according to the comparison between the different treatment groups regarding control group without treatment or infection. A significant difference is observed between the infected control without any treatment, showing that this group presents less bone loss compared to the research group treated with chlorhexidine 0.12%, with the group treated with amoxicillin and the group treated with chlorhexidine and amoxicillin. Therefore, these treatments do not avoid bone loss of the alveolar bone. On the other hand research groups with preventive phage, phage MOI 1 and phage MOI 0.1 present a significant difference with control group, presenting less bone loss (FIG. 25). The results that have been previously establish that the group treated with chlorhexidine presents a higher bone loss than the groups treated with preventive phage (*p<0.05), phage MOI 1 (*p<0.001) and phage MOI 0.1 (p<0.005), while the group treated with chlorhexidine plus amoxicillin presents higher bone loss than the groups with phage MOI 1 (***p<0.001) and phage MOI 0.1 (*p<0.05).

Example 11: Composition of a Mouthwash Based in Isolated Bacteriophages

This example describes the composition of the different components of the mouthwash generated from isolated bacteriophages.

The mouthwash presents inside its composition antioxidants, preservatives, artificial flavors, sweeteners, carrier, coloring and bacteriophages. Table 11 is a summary of quantities and types of compounds included in the mouthwash.

TABLE 11

Composition of mouthwash based in bacteriophages against *Fusobacterium nucleatum*.

| Type of compound | Compound | Final % | Proven range | Range | Others |
|---|---|---|---|---|---|
| Antioxidant | Sodium metabisulfite (Heyn) | 0.10% | | | |
| Preservative | Paragon III (Lipo, MCT-201030203) | 0.40% | 0.4%-0.8% | ≤0.6% | |
| Flavoring | Menthol Crystal (Montero, Batch 7494409) | 0.04% | | | |
| Sweetener | *Stevia* (NatFood) | 0.01% | | | |
| Carrier | Sterile water (Licrosolv water, Merck, neutral pH) | | | | pH > 5.5* |
| Bacteriophages | | $10^8$ ufp/mL | | $10^6$ a $10^{10}$ ufp/mL | |
| Flavoring | *Eucalyptus* Essence | 0.02% | 0.04%-0.02% | ≤0.02% | |
| Coloring | Shining Blue F&D A88200-AH CRAMEL | 0.001% | 0.001%-0.008% | ≤0.002% | |

Example 12: Research on Toxicity and Biochemical Parameters in Rats Treated with the Mouthwash-Type Composition Based in a Composition of Bacteriophages In one of the forms on the invention, the proposed pharmaceutical composition can be presented as a mouthwash, as it is exposed in example 11.

The evaluation of toxicity of mouthwash based in the disclosed pharmaceutical composition is presented below. In order to do this, the following toxicity parameters were evaluated in Sprague-Dawley rats after 2 months of treatment with the mouthwash: monitoring weekly weight of the animals, detection of bacteriophages accumulated in feces and urine, monitoring biochemical parameters associated with liver and renal damage and determination of other biochemical parameters as an indicator of the general physiological status of the rats.

a) Weekly Weight Monitoring

Considering the frequency and form of gathering the blood, urine and feces samples, the weight of each subject was monitored weekly, in order to associate it eventually to alterations in the biochemical analysis as a result of stress. At the end of the treatment, 4 of the subjects of the control group increased their weight in a range of 52 grams, while one of them (rat 1) kept its weight after suffering several oscillations during the process. In the experimental group, 4 rats increased approximately 120 g, and one of them decrease its weight in 33 g (rat 8) (FIG. 26).

b) Detection of Bacteriophages in Urine and Feces.

In order to evaluate the resistance of the bacteriophages in the gastrointestinal tract, the accumulation of bacteriophages was measured in 2 forms of excretion (urine and feces) by titration assays. Measuring of the control group was performed in order to discard any extra viral particle present in the research. According to this, during the 2 months of evaluation, no lysis plaques where observed in the samples collected from any of the subjects of the 4 performed counts (Table 12).

TABLE 12

Average count of bacteriophages in urine and feces of the research groups during the treatment period.

| | Control Group | | | Experimental Group | | |
|---|---|---|---|---|---|---|
| Week | Daily bacteriophage dose | UFP/mL Count in Feces | UFP/mL Count in Urine | Daily bacteriophage dose | UFP/mL Count in Feces | UFP/mL Count in Urine |
| 2 | 0 | 0 | 0 | $5 \times 10^6$ UFP/mL | 0 | 0 |
| 4 | 0 | 0 | 0 | $5 \times 10^6$ UFP/mL | 0 | 0 |
| 6 | 0 | 0 | 0 | $5 \times 10^6$ UFP/mL | 0 | 0 |
| 8 | 0 | 0 | 0 | $5 \times 10^6$ UFP/mL | 0 | 0 | c) Monitoring of Biochemical Parameters Associated with Liver and Renal Damage.

Liver Damage Monitoring

In order to monitor the liver function of the rats treated with the mouthwash, several biochemical parameters were analyzed from the blood samples of the rats. According to this, the moderate hemolysis production during samples gathering has to be considered, because it may alter the levels of certain enzymes and markers, such as alkaline phosphatase (ALP), alanine aminotransferase (ALT), aspartate aminotransferase (AST), gamma-glutamyl-transpeptidase (GGT), calcium and phosphorus.

The analysis of markers of liver damage revealed that the comparison of the experimental group with control group did not present significant variations during the whole treatment in the concentrations of bilirubin, ALP, ALT, AST and GGT (FIG. 27). The highest standard deviations in the values of ALP, ALT, AST and GGT during weeks 2, 4 and/or 6 happened due to moderate or acute hemolysis that affected at least 4 samples. At the end of the treatment, no subject presented enzyme levels or from the liver function markers outside the ones obtained by Leon et al. (2011), revealing that a damage or alteration of the liver function due to daily use of bacteriophages would not exist. This last point was particularly determined by the normal levels of bilirubin.

Renal Damage Monitoring

Renal damage monitoring consisted in determining the levels of creatinine and ureic nitrogen. Regarding the levels of creatinine, lower levels of creatinine were observed in the control and experimental group regarding reported values for comparison, and did not present significant differences between them (FIG. 28A), proving that a noticeable damage in the nephrons would not exist.

Regarding the blood urea nitrogen (BUN) levels, the volumes of the experimental group turned out to be slightly higher in weeks 2 and 4, and then remained like the control group in the final weeks of treatment (FIG. 18B), confirming the absence of moderate or acute damage of the renal function after daily use of mouthwash with bacteriophages. The statistical analyses of BUN did not show significant differences between the groups of the research during the 8 weeks of treatment.

Other Biochemical Parameters

Other biochemical parameters were evaluated, such as bone and/or muscular markers (calcium, phosphorus and alkaline phosphatase levels), protein profile (total concentrations of proteins, albumin and hemoglobin), glucose levels and cholesterol levels, with the aim of visualizing the physiological general status of the rats treated with the mouthwash.

Table 13 presents the levels of the evaluated biochemical parameters, comparing control group (C), experimental group (E) and referential values for male Sprague Dawley rats from CENPALAB (Leon and coll., 2011) (L).

In general, bone and/or muscular markers did not present significant differences between control and experimental group, discarding initially any alteration in bones, heart, blood coagulation, metabolic functioning and exocrine glandules, among others (Table 13). For its part, the concentration of total proteins, albumin and hemoglobin did not reveal either any significant difference between the research groups, suggesting the absence of nutritional problems or a lack of protein reabsorption in the subjects. Finally, general data as glucose and cholesterol concentration in blood were practically the same in both groups. When comparing this information with the previous reference, only phosphorus turned out to be slightly higher during the whole test (Table 13).

TABLE 13

Other biochemical parameters of rats that have been treated or non-treated with the mouthwash.

| Week | Referential value 0-6 | Referential value 8 | Obtained values 0 C | Obtained values 0 E | Obtained values 2 C | Obtained values 2 E | Obtained values 4 C |
|---|---|---|---|---|---|---|---|
| | L | L | C | E | C | E | C |
| Total Protein (g/dL) | 5.96-7.34 | 5.94-7.97 | 7.56 ± 0.503 | 7.9 ± 0.265 | 7.88 ± 0.576 | 7.98 ± 0.549 | 7.95 ± 5.452 |
| Albumin (g/dL) | 2.94-4.29 | 2.94-4.65 | 3.04 ± 0.230 | 3.24 ± 0.358 | 2.92 ± 0.110 | 3.02 ± 0.179 | 4.4 ± 1.968 |
| Globulin (g/dL) | 2.18-9.10 | 1.26-11.21 | 4.52 ± 0.390 | 4.66 ± 0.167 | 4.96 ± 0.498 | 4.96 ± 0.434 | 7.4 ± 3.309 |
| Calcium (mg/dL) | 8.86-11.26 | 8.78-13.11 | 9.7 ± 1.3 | 9.8 ± 0.604 | 9.12 ± 0.593 | 10.26 ± 0.904 | 12.8 ± 5.724 |
| Phosphorus (mg/dL) | 6.01-8.68 | 5.26-8.44 | 9.36 ± 0.956 | 10.22 ± 1.083 | 9.96 ± 0.865 | 10.22 ± 1.083 | 14.5 ± 8.072 |
| Glucose (mg/dL) | 58.0-160.2 | 48.4-91.2 | 105.40 ± 15.645 | 119.76 ± 37.339 | 74.912 ± 22.604 | 84.936 ± 31.48 | 78.4 ± 44.469 |
| Cholesterol (mg/dL) | 40.3-84.7 | 52.2-95.7 | 70.18 ± 9.154 | 78.72 ± 10.105 | 77.4 ± 8.351 | 78.66 ± 11.072 | 97 ± 43.38 |

| Week | Obtained values 4 E | Obtained values 6 C | Obtained values 6 E | Obtained values 8 C | Obtained values 8 E |
|---|---|---|---|---|---|
| Total Protein (g/dL) | 9.55 ± 4.369 | 4.92 ± 4.109 | 5.88 ± 3.790 | 7.5 ± 0.158 | 7.42 ± 0.507 |
| Albumin (g/dL) | 3.35 ± 1.559 | 1.929 ± 1.555 | 2.29 ± 1.633 | 2.72 ± 0.311 | 2.84 ± 0.219 |
| Globulin (g/dL) | 6.2 ± 2.868 | 3.049 ± 2.485 | 4.042 ± 2.778 | 4.78 ± 0.438 | 4.580 ± 0.311 |
| Calcium (mg/dL) | 12.1 ± 6.069 | 6.075 ± 5.016 | 7.52 ± 4.948 | 10.26 ± 0.865 | 9.48 ± 0.192 |
| Phosphorus (mg/dL) | 13.920 ± 2.781 | 6.584 ± 4.995 | 8.071 ± 6.172 | 11.82 ± 1.59 | 11.48 ± 1.937 |
| Glucose (mg/dL) | 90.350 ± 51.662 | 67.91 ± 38.777 | 59.22 ± 24.339 | 90.46 ± 51.705 | 65.762 ± 17.267 |
| Cholesterol (mg/dL) | 92.25 ± 43.849 | 50.647 ± 37.819 | 57.51 ± 36.432 | 60.3 ± 10.51 | 59.4 ± 6.985 |

The invention claimed is:

1. A method for preventing and/or treating diseases associated with *Fusobacterium nucleatum* in a subject in need thereof, comprising administering to the subject a pharmaceutical composition comprising:
   a) a therapeutically effective amount of bacteriophage FnpΦ11; and
   b) one or more pharmaceutically acceptable carrier and/or excipients;
   wherein the bacteriophage FnpΦ11 is a lytic bacteriophage specific for *Fusobacterium nucleatum*.

2. The method according to claim 1, wherein the composition further comprises one or more additional lytic bacteriophages specific for *Fusobacterium nucleatum*.

3. The method according to claim 2, wherein the one or more additional lytic bacteriophages specific for *Fusobacterium nucleatum* comprise bacteriophage FnpΦ02-14 and/or bacteriophage FnnΦ107.

4. A method for preventing and/or treating diseases associated with *Fusobacterium nucleatum* in a subject in need thereof, comprising administering to the subject a pharmaceutical composition comprising:
   a) a therapeutically effective amount of three bacteriophages, wherein the three bacteriophages are FnpΦ02-14, FnpΦ11, and FnnΦ107; and
   b) one or more pharmaceutically acceptable carrier and/or excipients;
   wherein the three bacteriophages are lytic bacteriophages specific for *Fusobacterium nucleatum*.

5. The method according to claim 4, wherein said lytic bacteriophages specific for *Fusobacterium nucleatum* are present in equal or different concentrations, in the range of $10^4$ to $10^{12}$ UFP/mL.

6. The method according to claim 4, wherein said lytic bacteriophages specific for *Fusobacterium nucleatum* correspond to lytic bacteriophages that have been deposited in the International Depositary Authority of Canada (IDAC) under deposit numbers IDAC 300115-01, IDAC 300115-02 and IDAC 300115-03, respectively.

7. The method according to claim 4, wherein the disease associated with *Fusobacterium nucleatum* is periodontal disease.

8. The method according to claim 4, wherein the disease associated with *Fusobacterium nucleatum* is an extra oral disease produced by systemic dissemination of *Fusobacterium nucleatum*.

9. The method according to claim 4, wherein the disease associated with *Fusobacterium nucleatum* is colorectal cancer.

10. The method according to claim 4, wherein the disease associated with *Fusobacterium nucleatum* comprises Abnormal Pregnancy Outcomes, premature labor or complications during pregnancy.

11. A pharmaceutical composition comprising:
   a) a therapeutically effective amount of bacteriophage FnpΦ11;
   b) one or more pharmaceutically acceptable excipients; and
   c) an antioxidant;
   wherein the antioxidant is sodium metabisulphite, and
   wherein the bacteriophage FnpΦ11 is a lytic bacteriophage specific for *Fusobacterium nucleatum*.

12. The pharmaceutical composition according to claim 11, wherein the composition further comprises one or more additional lytic bacteriophages specific for *Fusobacterium nucleatum*.

13. The pharmaceutical composition according to claim 12, wherein the one or more additional lytic bacteriophages specific for *Fusobacterium nucleatum* comprise bacteriophage FnpΦ02-14 and/or bacteriophage FnnΦ107.

14. A pharmaceutical composition comprising:
   a) a therapeutically effective amount of three bacteriophages, wherein the three bacteriophages are FnpΦ02-14, FnpΦ11, and FnnΦ107; and
   b) one or more pharmaceutically acceptable carriers and/or excipients;
   wherein the three bacteriophages are lytic bacteriophages specific for *Fusobacterium nucleatum*.

15. The pharmaceutical composition according to claim 14, wherein said lytic bacteriophages specific for *Fusobacterium nucleatum* are present in equal or different concentrations, in the range of $10^4$ to $10^{12}$ UFP/mL.

16. The pharmaceutical composition according to claim 14, wherein said lytic bacteriophages specific for *Fusobacterium nucleatum* are present in equal or different concentrations, in the range of $10^6$ to $10^{10}$ CFU/mL.

17. The pharmaceutical composition according to claim 14, comprising a mixture of the three lytic bacteriophages, FnpΦ02-14, FnpΦ11 and FnnΦ107, at a concentration of $10^8$, $10^{10}$ and $10^8$ CFU/mL, respectively.

18. The pharmaceutical composition according to claim 14, wherein said lytic bacteriophages specific for *Fusobacterium nucleatum*, comprise FnpΦ02-14, FnpΦ11, and FnnΦ107 and correspond to lytic bacteriophages that have been deposited in the International Depositary Authority of Canada (IDAC) under deposit numbers IDAC 300115-01, IDAC 300115-02 and IDAC 300115-03, respectively.

19. The pharmaceutical composition according to claim 14, wherein said lytic bacteriophages have a Multiplicity of Infection (MOI) of 0.01 to 1.

20. The pharmaceutical composition according to claim 14, wherein the composition is formulated as an oral dosage form selected from mouthwash, toothpaste, dissolving films, spray, dental floss, gels, varnish, micro and nanoparticles, pills, capsules, suspensions, composites, composed resins, capping, meshes, freeze-dried, powder, coated metal implants, coated porcelain crowns, silicone, sealants, cementation elements, and adhesion elements.

21. The pharmaceutical composition according to claim 20, wherein the composition is formulated as a mouthwash further comprising one or more antioxidants, preservatives, artificial flavoring, sweeteners, carriers and artificial coloring inside the composition.

22. The pharmaceutical composition according to claim 20, wherein the composition is formulated as a mouthwash further comprising an antioxidant, a preservative, a flavoring, a sweetener, a carrier, and bacteriophages specific for *Fusobacterium nucleatum* comprising FnpΦ02-14, FnpΦ11 and FnnΦ107, wherein the bacteriophages are present in equal or different concentrations, in the range from $10^6$ to $10^{10}$ CFU/mL.

23. The method according to claim 1, wherein the one or more bacteriophages are present in a concentration of $10^4$ to $10^{12}$ UFP/mL.

24. The method according to claim 1, wherein the disease associated with *Fusobacterium nucleatum* comprises a disease of the oral cavity.

25. The method according to claim 4, wherein the disease associated with *Fusobacterium nucleatum* comprises a disease of the oral cavity.

26. The pharmaceutical composition according to claim 11, wherein the one or more bacteriophages are present in a concentration of $10^4$ to $10^{12}$ UFP/mL.

27. The pharmaceutical composition according to claim 11, wherein the composition is formulated as an oral formulation.

28. The pharmaceutical composition according to claim 14, wherein the composition is formulated as an oral formulation.

29. The pharmaceutical composition according to claim 11, wherein the composition is formulated as a mouthwash.

30. The pharmaceutical composition according to claim 14, wherein the composition is formulated as a mouthwash.

31. A pharmaceutical composition comprising:
   a) a therapeutically effective amount of bacteriophage FnpΦ11;
   b) one or more pharmaceutically acceptable excipients;
   c) one or more additional lytic bacteriophages specific for *Fusobacterium nucleatum*; and
   d) an antioxidant;
   wherein the antioxidant is sodium metabisulphite.

32. The pharmaceutical composition according to claim 11, wherein the composition is formulated as an oral dosage form selected from the group consisting of mouthwash, toothpaste, dissolving film, spray, dental floss, gel, varnish, micro and nanoparticle, pill, capsule, suspension, composite, composed resin, capping, meshes, freeze-dried, powder, coated metal implant, coated porcelain crown, silicone, sealant, cementation element, and adhesion element.

33. The pharmaceutical composition according to claim 31, wherein the composition is formulated as an oral dosage form selected from the group consisting of mouthwash, toothpaste, dissolving film, spray, dental floss, gel, varnish, micro and nanoparticle, pill, capsule, suspension, composite, composed resin, capping, meshes, freeze-dried, powder, coated metal implant, coated porcelain crown, silicone, sealant, cementation element, and adhesion element.

34. The pharmaceutical composition according to claim 11, wherein the one or more pharmaceutically acceptable excipients is selected from the group consisting of an artificial flavor, a sweetener, a colorant, and any combination thereof.

35. The pharmaceutical composition according to claim 11, wherein the pharmaceutical composition further comprises a preservative, an antimicrobial agent, or any combination thereof.

36. The pharmaceutical composition according to claim 31, wherein the pharmaceutical composition comprises the one or more pharmaceutically acceptable excipients selected from the group consisting of an artificial flavor, a sweetener, a colorant, and any combination thereof.

37. The pharmaceutical composition according to claim 31, wherein the pharmaceutical composition further comprises a preservative, an antimicrobial agent, or any combination thereof.

* * * * *

SEQUENCE LISTING

<160> NUMBER OF SEQ ID NOS: 12

<210> SEQ ID NO 1
<211> LENGTH: 18
<212> TYPE: DNA
<213> ORGANISM: Porphyromonas gingivalis
<220> FEATURE:
<221> NAME/KEY: primer_bind
<222> LOCATION: (1)..(18)
<223> OTHER INFORMATION: 16S rDNA, Pgin-1/primer_bind

<400> SEQUENCE: 1
tgtagatgac tgaaaacc                                                    18

<210> SEQ ID NO 2
<211> LENGTH: 20
<212> TYPE: DNA
<213> ORGANISM: Porphyromonas gingivalis
<220> FEATURE:
<221> NAME/KEY: primer_bind
<222> LOCATION: (1)..(20)
<223> OTHER INFORMATION: 16S rDNA, Pgin-2/primer_bind

<400> SEQUENCE: 2
acgtcatccc caccttcctc                                                  20

<210> SEQ ID NO 3
<211> LENGTH: 20
<212> TYPE: DNA
<213> ORGANISM: Porphyromonas gingivalis
<220> FEATURE:
<221> NAME/KEY: primer_bind
<222> LOCATION: (1)..(20)
<223> OTHER INFORMATION: 16S rDNA, Fspp-1/primer_bind

<400> SEQUENCE: 3
ggatttattg ggcgtaaagc                                                  20

<210> SEQ ID NO 4
<211> LENGTH: 24
<212> TYPE: DNA
<213> ORGANISM: Porphyromonas gingivalis
<220> FEATURE:
<221> NAME/KEY: primer_bind
<222> LOCATION: (1)..(24)
<223> OTHER INFORMATION: 16S rDNA, Fspp-2/primer_bind

<400> SEQUENCE: 4
ggcattccta caaatatcta cgaa                                             24

<210> SEQ ID NO 5
<211> LENGTH: 389
<212> TYPE: DNA
<213> ORGANISM: Fusobacterium nucleatum
<220> FEATURE:
<221> NAME/KEY: CDS
<222> LOCATION: (1)..(387)
<223> OTHER INFORMATION: Phague Fnp(phi)02
<300> PUBLICATION INFORMATION:
<313> RELEVANT RESIDUES IN SEQ ID NO: (1)..(389)

<400> SEQUENCE: 5 aag ctt gtt ggt gcc ggt att ttg cct gct gat tct cgt acg gtg ttg      48
Lys Leu Val Gly Ala Gly Ile Leu Pro Ala Asp Ser Arg Thr Val Leu
1               5                   10                  15 gag atg ttg ggg ctt gat gat gtg cag gtt gag gct gtg atg cgt cat      96
Glu Met Leu Gly Leu Asp Asp Val Gln Val Glu Ala Val Met Arg His
            20                  25                  30

```
cgt gct gag tcg tct gac ccg ttg gcg gca ctg gct ggg gct ata tcg    144
Arg Ala Glu Ser Ser Asp Pro Leu Ala Ala Leu Ala Gly Ala Ile Ser
         35                  40                  45 cgt caa act aac gag gtt tga tag gcg atg gct tcg ggt gct atg tcg    192
Arg Gln Thr Asn Glu Val         Ala Met Ala Ser Gly Ala Met Ser
 50                                  55                  60 agg ctt gcg gtg act gag tat cag cgg cag gcg att cgt ttt gcc ggg    240
Arg Leu Ala Val Thr Glu Tyr Gln Arg Gln Ala Ile Arg Phe Ala Gly
             65                  70                  75 aaa tac gct ggg tat tat tct gag ctt ggt cgt ttg tgg cgt gcc ggg    288
Lys Tyr Ala Gly Tyr Tyr Ser Glu Leu Gly Arg Leu Trp Arg Ala Gly
 80                  85                  90 aag atg agt gac acg cag tat gtg cgt ttg tgt gtg gag ttg gag cgt    336
Lys Met Ser Asp Thr Gln Tyr Val Arg Leu Cys Val Glu Leu Glu Arg
 95                 100                 105                 110 gcc ggc cat gat ggt tcc gcg act atg gcg gcc aaa ttc gtt tca aaa    384
Ala Gly His Asp Gly Ser Ala Thr Met Ala Ala Lys Phe Val Ser Lys
             115                 120                 125 ttt cg                                                             389
Phe

<210> SEQ ID NO 6
<211> LENGTH: 54
<212> TYPE: PRT
<213> ORGANISM: Fusobacterium nucleatum

<400> SEQUENCE: 6

Lys Leu Val Gly Ala Gly Ile Leu Pro Ala Asp Ser Arg Thr Val Leu
 1               5                  10                  15

Glu Met Leu Gly Leu Asp Asp Val Gln Val Glu Ala Val Met Arg His
             20                  25                  30

Arg Ala Glu Ser Ser Asp Pro Leu Ala Ala Leu Ala Gly Ala Ile Ser
         35                  40                  45

Arg Gln Thr Asn Glu Val
     50

<210> SEQ ID NO 7
<211> LENGTH: 73
<212> TYPE: PRT
<213> ORGANISM: Fusobacterium nucleatum

<400> SEQUENCE: 7

Ala Met Ala Ser Gly Ala Met Ser Arg Leu Ala Val Thr Glu Tyr Gln
 1               5                  10                  15

Arg Gln Ala Ile Arg Phe Ala Gly Lys Tyr Ala Gly Tyr Tyr Ser Glu
             20                  25                  30

Leu Gly Arg Leu Trp Arg Ala Gly Lys Met Ser Asp Thr Gln Tyr Val
         35                  40                  45

Arg Leu Cys Val Glu Leu Glu Arg Ala Gly His Asp Gly Ser Ala Thr
     50                  55                  60

Met Ala Ala Lys Phe Val Ser Lys Phe
 65                  70

<210> SEQ ID NO 8
<211> LENGTH: 118
<212> TYPE: PRT
<213> ORGANISM: Fusobacterium nucleatum

<400> SEQUENCE: 8
```

```
Lys Leu Val Gly Ala Gly Ile Leu Pro Ala Asp Ser Arg Thr Val Leu
1               5                   10                  15

Glu Met Leu Gly Leu Asp Asp Val Gln Val Glu Ala Val Met Arg His
            20                  25                  30

Arg Ala Glu Ser Ser Asp Pro Leu Ala Ala Leu Ala Gly Ala Ile Ser
        35                  40                  45

Arg Gln Thr Asn Glu Val Ala Met Ala Ser Gly Ala Met Ser Arg Leu
    50                  55                  60

Ala Val Thr Glu Tyr Gln Arg Gln Ala Ile Arg Phe Ala Gly Lys Tyr
65              70                  75                  80

Ala Gly Tyr Tyr Ser Glu Leu Gly Arg Leu Trp Arg Ala Gly Lys Met
                85                  90                  95

Ser Asp Thr Gln Tyr Val Arg Leu Cys Val Glu Leu Glu Arg Ala Gly
            100                 105                 110

His Asp Gly Ser Ala Thr
        115
```

<210> SEQ ID NO 9
<211> LENGTH: 389
<212> TYPE: DNA
<213> ORGANISM: Propionibacterium acnes
<220> FEATURE:
<221> NAME/KEY: CDS
<222> LOCATION: (1)..(387)
<223> OTHER INFORMATION: PA6 sequence

<400> SEQUENCE: 9

```
aag ctt gtt ggt gcc ggt att ttg cct gct gat tct cgt acg gtg ttg      48
Lys Leu Val Gly Ala Gly Ile Leu Pro Ala Asp Ser Arg Thr Val Leu
1               5                   10                  15 gag atg ttg ggg ctt gat gat gtg cag gtt gag gct gtg atg cgt cat      96
Glu Met Leu Gly Leu Asp Asp Val Gln Val Glu Ala Val Met Arg His
            20                  25                  30 cgt gct gag tcg tct gac ccg ttg gcg gtg ctt gct ggg gct ata tcg     144
Arg Ala Glu Ser Ser Asp Pro Leu Ala Val Leu Ala Gly Ala Ile Ser
        35                  40                  45 cgt caa act aac gag gta tga tag gcg atg gct tcg ggg gtt gag gcg     192
Arg Gln Thr Asn Glu Val         Ala Met Ala Ser Gly Val Glu Ala
    50                              55                  60 agg ctt gcg gcg act gag tat cag cgt gag gcg gtc agg ttt gct ggg     240
Arg Leu Ala Ala Thr Glu Tyr Gln Arg Glu Ala Val Arg Phe Ala Gly
            65                  70                  75 aag tat gcg ggc tat tat tct gag ctt ggt cgt ttg tgg cgt gcc ggc     288
Lys Tyr Ala Gly Tyr Tyr Ser Glu Leu Gly Arg Leu Trp Arg Ala Gly
80                  85                  90 agg atg agt gac acg cag tat gtg cgt ttg tgt gtg gag ttg gag cgt     336
Arg Met Ser Asp Thr Gln Tyr Val Arg Leu Cys Val Glu Leu Glu Arg
95              100                 105                 110 gcc ggc cat gat ggt tcg gca tcg ttg gct gcc agg ttt gtg tcg gat     384
Ala Gly His Asp Gly Ser Ala Ser Leu Ala Ala Arg Phe Val Ser Asp
            115                 120                 125 ttt cg                                                              389
Phe
```

<210> SEQ ID NO 10
<211> LENGTH: 54
<212> TYPE: PRT
<213> ORGANISM: Propionibacterium acnes

<400> SEQUENCE: 10

```
Lys Leu Val Gly Ala Gly Ile Leu Pro Ala Asp Ser Arg Thr Val Leu
1               5                   10                  15

Glu Met Leu Gly Leu Asp Asp Val Gln Val Glu Ala Val Met Arg His
            20                  25                  30

Arg Ala Glu Ser Ser Asp Pro Leu Ala Val Leu Ala Gly Ala Ile Ser
        35                  40                  45

Arg Gln Thr Asn Glu Val
        50
```

<210> SEQ ID NO 11
<211> LENGTH: 73
<212> TYPE: PRT
<213> ORGANISM: Propionibacterium acnes

<400> SEQUENCE: 11

```
Ala Met Ala Ser Gly Val Glu Ala Arg Leu Ala Ala Thr Glu Tyr Gln
1               5                   10                  15

Arg Glu Ala Val Arg Phe Ala Gly Lys Tyr Ala Gly Tyr Tyr Ser Glu
            20                  25                  30

Leu Gly Arg Leu Trp Arg Ala Gly Arg Met Ser Asp Thr Gln Tyr Val
        35                  40                  45

Arg Leu Cys Val Glu Leu Glu Arg Ala Gly His Asp Gly Ser Ala Ser
    50                  55                  60

Leu Ala Ala Arg Phe Val Ser Asp Phe
65                  70
```

<210> SEQ ID NO 12
<211> LENGTH: 127
<212> TYPE: PRT
<213> ORGANISM: Propionibacterium acnes

<400> SEQUENCE: 12

```
Lys Leu Val Gly Ala Gly Ile Leu Pro Ala Asp Ser Arg Thr Val Leu
1               5                   10                  15

Glu Met Leu Gly Leu Asp Asp Val Gln Val Glu Ala Val Met Arg His
            20                  25                  30

Arg Ala Glu Ser Ser Asp Pro Leu Ala Val Leu Ala Gly Ala Ile Ser
        35                  40                  45

Arg Gln Thr Asn Glu Val Ala Met Ala Ser Gly Val Glu Ala Arg Leu
    50                  55                  60

Ala Ala Thr Glu Tyr Gln Arg Glu Ala Val Arg Phe Ala Gly Lys Tyr
65                  70                  75                  80

Ala Gly Tyr Tyr Ser Glu Leu Gly Arg Leu Trp Arg Ala Gly Arg Met
                85                  90                  95

Ser Asp Thr Gln Tyr Val Arg Leu Cys Val Glu Leu Glu Arg Ala Gly
            100                 105                 110

His Asp Gly Ser Ala Ser Leu Ala Ala Arg Phe Val Ser Asp Phe
        115                 120                 125
```